(12) United States Patent
Choi et al.

(10) Patent No.: US 11,856,853 B2
(45) Date of Patent: Dec. 26, 2023

(54) ORGANIC COMPOUND, ORGANIC LIGHT EMITTING DIODE AND ORGANIC LIGHT EMITTING DEVICE INCLUDING THE COMPOUND

(71) Applicants: LG DISPLAY CO., LTD., Seoul (KR); LG CHEM, LTD., Seoul (KR)

(72) Inventors: Hyong-Jong Choi, Paju-si (KR); Bo-Min Seo, Paju-si (KR); Ik-Rang Choe, Paju-si (KR); Hye-Gun Ryu, Paju-si (KR); Jin-Joo Kim, Paju-si (KR)

(73) Assignees: LG DISPLAY CO., LTD., Seoul (KR); LG CHEM, LTD., Seoul (KR)

( * ) Notice: Subject to any disclaimer, the term of this patent is extended or adjusted under 35 U.S.C. 154(b) by 593 days.

(21) Appl. No.: 17/105,096

(22) Filed: Nov. 25, 2020

(65) Prior Publication Data

US 2021/0167300 A1  Jun. 3, 2021

(30) Foreign Application Priority Data

Dec. 3, 2019  (KR) .......................... 10-2019-0158925
Oct. 30, 2020  (KR) .......................... 10-2020-0142736

(51) Int. Cl.
   *H10K 85/60*  (2023.01)
   *C09K 11/06*  (2006.01)
   (Continued)

(52) U.S. Cl.
   CPC ....... *H10K 85/6574* (2023.02); *C07D 493/04* (2013.01); *C09K 11/06* (2013.01);
   (Continued)

(58) Field of Classification Search
   CPC ........... H10K 10/6574; H10K 10/6572; H10K 10/6576; H10K 50/11; H10K 50/15;
   (Continued)

(56) References Cited

U.S. PATENT DOCUMENTS

2018/0069182 A1* 3/2018 Hatakeyama ......... C07F 7/0816
2018/0094000 A1* 4/2018 Hatakeyama ........ H10K 85/631
(Continued)

FOREIGN PATENT DOCUMENTS

CN      102056899 A    5/2011
JP      2010-45281 A   2/2010
(Continued)

*Primary Examiner* — Michael M. Bernshteyn
(74) *Attorney, Agent, or Firm* — Birch, Stewart, Kolasch & Birch, LLP

(57) ABSTRACT

The present disclosure relates to an organic compound having the following structure of Chemical Formula 1, and an organic light emitting diode (OLED) and an organic light emitting device including the organic compound. The organic compound is a bipolar organic compound having a p-type moiety and an n-type moiety. The organic compound has a high excited triplet energy level, a wide energy bandgap and excellent thermal stability. When the organic compound is introduced into an emitting material layer (EML) of the OLED, holes and electrons are recombined in the whole area of the EML, thus the OLED can improve its luminous efficiency and luminous lifetime.

Chemical Formula 1

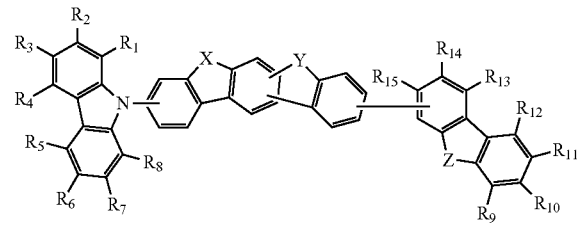

23 Claims, 16 Drawing Sheets

(51) Int. Cl.
*C07D 493/04* (2006.01)
*H10K 50/11* (2023.01)
*H10K 50/15* (2023.01)
*H10K 50/16* (2023.01)
*H10K 50/17* (2023.01)
*H10K 50/18* (2023.01)
*H10K 59/12* (2023.01)
*H10K 101/10* (2023.01)
*H10K 101/30* (2023.01)
*H10K 101/40* (2023.01)

(52) U.S. Cl.
CPC ..... *H10K 85/6572* (2023.02); *H10K 85/6576* (2023.02); *C09K 2211/1018* (2013.01); *H10K 50/11* (2023.02); *H10K 50/15* (2023.02); *H10K 50/16* (2023.02); *H10K 50/17* (2023.02); *H10K 50/171* (2023.02); *H10K 50/18* (2023.02); *H10K 59/12* (2023.02); *H10K 2101/10* (2023.02); *H10K 2101/30* (2023.02); *H10K 2101/40* (2023.02)

(58) Field of Classification Search
CPC ........ H10K 50/16; H10K 50/17; H10K 50/18; H10K 50/171; H10K 59/12; H10K 2101/10; H10K 2101/30; H10K 2101/40; C09K 11/06; C09K 2211/1018; C07D 493/04
USPC .......................................................... 428/690
See application file for complete search history.

(56) References Cited

U.S. PATENT DOCUMENTS

| | | | |
|---|---|---|---|
| 2018/0182981 A1* | 6/2018 | Chen | C09K 11/025 |
| 2018/0337350 A1* | 11/2018 | Li | C07F 15/006 |
| 2019/0036042 A1* | 1/2019 | Kim | H10K 85/346 |
| 2019/0074455 A1* | 3/2019 | Chen | C07F 15/0086 |
| 2019/0115538 A1* | 4/2019 | Lim | H10K 85/6572 |
| 2019/0207112 A1* | 7/2019 | Hatakeyama | C09K 11/02 |
| 2019/0319196 A1* | 10/2019 | Sim | C07D 403/10 |
| 2020/0058885 A1* | 2/2020 | Hong | H10K 85/322 |
| 2020/0185626 A1* | 6/2020 | Yuuki | C07F 9/6596 |
| 2021/0020847 A1* | 1/2021 | Yoon | C07D 491/20 |
| 2021/0163427 A1* | 6/2021 | Kim | H10K 85/657 |

FOREIGN PATENT DOCUMENTS

| | | |
|---|---|---|
| KR | 10-2019-0064009 A | 6/2019 |
| KR | 10-2020-0073602 A | 6/2020 |

* cited by examiner

ORGANIC COMPOUND, ORGANIC LIGHT EMITTING DIODE AND ORGANIC LIGHT EMITTING DEVICE INCLUDING THE COMPOUND

CROSS-REFERENCE TO RELATED APPLICATIONS

This application claims the priority benefit under 35 U.S.C. § 119(a) of Korean Patent Application No. 10-2019-0158925, filed in the Republic of Korea on Dec. 3, 2019, and Korean Patent No. 10-2020-0142736, filed in the Republic of Korea on Oct. 30, 2020, the entire contents of all these applications are incorporated herein by reference in its entirety into the present application.

BACKGROUND

Technical Field

The present disclosure relates to an organic compound, and more specifically, to an organic compound having excellent luminous properties, an organic light emitting diode and an organic light emitting device including the compound.

Discussion of the Related Art

As display devices have become larger, there exists a need for a flat display device with a lower space requirement. Among the flat display devices used widely at present, organic light emitting diodes (OLEDs) are rapidly replacing liquid crystal display devices (LCDs).

The OLED can be formed as a thin film having a thickness less than 2000 Å and can implement unidirectional or bidirectional images as electrode configurations. In addition, OLEDs can be formed on a flexible transparent substrate such as a plastic substrate so that the OLED can be implemented in a flexible or foldable display with ease. Moreover, the OLED can be driven at a lower voltage of 10 V or less. Besides, the OLED has relatively lower power consumption for driving compared to plasma display panels and inorganic electroluminescent devices, and the color purity of the OLED is very high. Particularly, the OLED can implement red, green and blue colors, and thus it has attracted a lot of attention as a light emitting device.

In the OLED, when electrical charges are injected into an emitting material layer between an electron injection electrode (i.e., cathode) and a hole injection electrode (i.e., anode), electrical charges are recombined to form excitons, and then emit light as the recombined excitons are shifted to a stable ground state. Conventional fluorescent materials have low luminous efficiency because only singlet exciton is involved in the luminescence process. On the other hand, conventional phosphorescent materials in which triplet exciton as well as singlet exciton can be involved in the luminescence process have exhibited high luminous efficiency compared to the fluorescent materials.

However, the metal complex as the representative phosphorescent material has too short luminous lifetime to be applicable into commercial devices. Particularly, the phosphorescent host should have triplet energy higher than the phosphorescent dopant in order to prevent the triplet energy of the phosphorescent dopant from transferring to the host. However, as the organic aromatic compound has increased conjugated structure or has much fused rings, its triplet energy level is rapidly decreased, thus the organic compounds that can be used as the phosphorescent host are very limited.

SUMMARY

Accordingly, embodiments of the present disclosure are directed to an organic compound and an OLED and an organic light emitting device including the organic compound that substantially obviates one or more of the problems due to the limitations and disadvantages of the related art.

An object of the present disclosure is to provide an organic compound that has high a high excited triplet energy level and a bipolar property, an OLED and an organic light emitting device into which the organic compound is applied.

Another object of the present disclosure is to provide an organic compound that has excellent thermal stability and that can prevent non-radiative recombination, an OLED and an organic light emitting device into which the organic compound is applied.

Additional features and aspects will be set forth in the description that follows, and in part will be apparent from the description, or can be learned by practice of the inventive concepts provided herein. Other features and aspects of the inventive concept can be realized and attained by the structure particularly pointed out in the written description, or derivable therefrom, and the claims hereof as well as the appended drawings.

To achieve these and other aspects of the inventive concepts, as embodied and broadly described, the present disclosure provides an organic compound having the following structure of Chemical Formula 1:

Chemical Formula 1

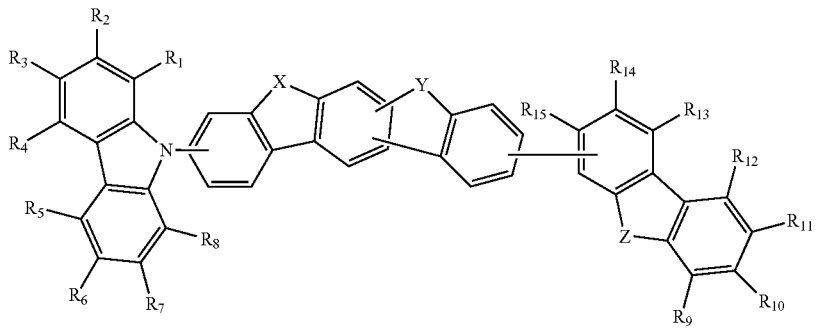

wherein each of $R_1$ to $R_{15}$ is independently selected from the group consisting of hydrogen, an unsubstituted or substituted silyl group, an unsubstituted or substituted $C_1$-$C_{20}$ alkyl group, an unsubstituted or substituted $C_1$-$C_{20}$ alkoxy group, an unsubstituted or substituted $C_1$-$C_{20}$ alkyl amino group, an unsubstituted or substituted $C_6$-$C_{30}$ aromatic group and an unsubstituted or substituted $C_3$-$C_{30}$ hetero aromatic group, or two adjacent groups among $R_1$ to $R_{15}$ form an unsubstituted or substituted $C_6$-$C_{20}$ aromatic ring or an unsubstituted or substituted $C_3$-$C_{20}$ hetero aromatic ring; each of X, Y and Z is independently oxygen (O) or sulfur (S).

In another aspect, the present disclosure provides an OLED that comprises a first electrode; a second electrode facing the first electrode; and an emitting material layer disposed between the first and second electrodes, wherein the first emitting material layer comprises the organic compound.

In still another aspect, the present disclosure provides an organic light emitting device that comprises a substrate and an OLED disposed over the substrate, as described above.

It is to be understood that both the foregoing general description and the following detailed description are exemplary and explanatory and are intended to provide further explanation of the inventive concepts as claimed.

BRIEF DESCRIPTION OF THE DRAWINGS

The accompanying drawings, which are included to provide a further understanding of the disclosure, are incorporated in and constitute a part of this application, illustrate embodiments of the disclosure and together with the description serve to explain principles of the disclosure.

DETAILED DESCRIPTION OF THE EMBODIMENTS

Figure 1:
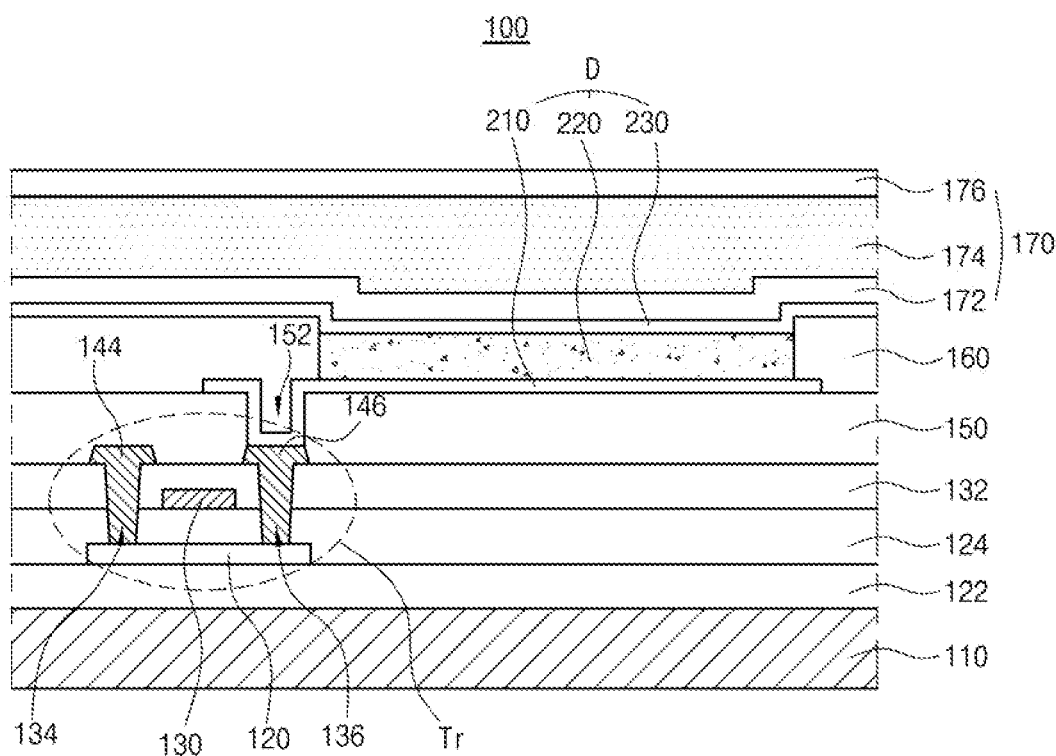
FIG. 1 is a schematic cross-sectional view illustrating an organic light emitting display device in accordance with one exemplary aspect of the present disclosure.

Reference will now be made in detail to aspects of the disclosure, examples of which are illustrated in the accompanying drawings.

[Organic Compound]

An organic compound applied to an organic light emitting diode (OLED) should have excellent charge affinities and maintain stable properties during driving the OLED. Particularly, the luminous material is the most important factor in determining the luminous efficiency of the OLED. The luminous material should have high luminous efficiency and high charge mobility, and have proper energy levels with regard to other materials applied into the same emissive layer and adjacently disposed emissive layers. An organic compound of the present disclosure includes a carbazole moiety and a dibenzofuran or dibenzothiophene moiety each of which is linked to a central five-member fused hetero aromatic linker moiety so that it can have excellent thermal property and luminous property. The organic compound of the present disclosure can have the following structure of Chemical Formula 1:

[Chemical Formula 1]

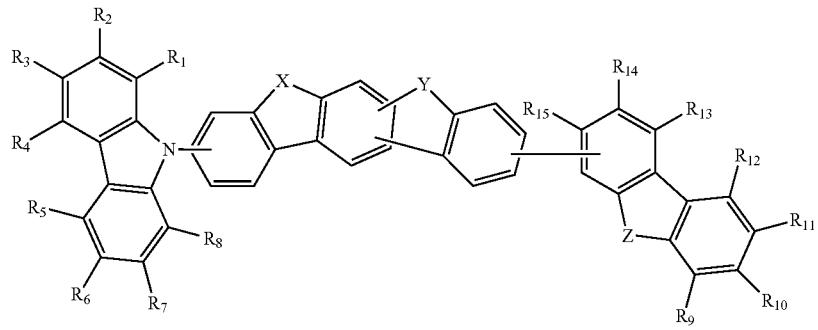

In Chemical Formula 1, each of $R_1$ to $R_{15}$ is independently selected from the group consisting of hydrogen, an unsubstituted or substituted silyl group, an unsubstituted or substituted $C_1$-$C_{20}$ alkyl group, an unsubstituted or substituted $C_1$-$C_{20}$ alkoxy group, an unsubstituted or substituted $C_1$-$C_{20}$ alkyl amino group, an unsubstituted or substituted $C_6$-$C_{30}$ aromatic group and an unsubstituted or substituted $C_3$-$C_{30}$ hetero aromatic group, or two adjacent groups among $R_1$ to $R_{15}$ form an unsubstituted or substituted $C_6$-$C_{20}$ aromatic ring or an unsubstituted or substituted $C_3$-$C_{20}$ hetero aromatic ring; each of X, Y and Z is independently oxygen (O) or sulfur (S).

As used herein, the term "unsubstituted" means that hydrogen is linked, and in this case, hydrogen comprises protium, deuterium and tritium.

As used the term "substituted" herein, the substitution group comprises, but is not limited to, unsubstituted or halogen-substituted $C_1$-$C_{20}$ alkyl, unsubstituted or halogen-substituted $C_1$-$C_{20}$ alkoxy, halogen, cyano, —$CF_3$, a hydroxyl group, a carboxylic group, a carbonyl group, an amino group, a $C_1$-$C_{10}$ alkyl amino group, a $C_6$-$C_{30}$ aryl amino group, a $C_3$-$C_{30}$ hetero aryl amino group, a $C_6$-$C_{30}$ aryl group, a $C_3$-$C_{30}$ hetero aryl group, a nitro group, a hydrazyl group, a sulfonate group, a $C_1$-$C_{20}$ alkyl silyl group, a $C_6$-$C_{30}$ aryl silyl group and a $C_3$-$C_{30}$ hetero aryl silyl group.

As used herein, the term "hetero" in such as "a hetero aromatic ring", "a hetero cycloalkyene group", "a hetero arylene group", "a hetero aryl alkylene group", "a hetero aryl oxylene group", "a hetero cycloalkyl group", "a hetero aryl group", "a hetero aryl alkyl group", "a hetero aryloxyl group", "a hetero aryl amino group" means that at least one carbon atom, for example 1-5 carbons atoms, constituting an aromatic ring or an alicyclic ring is substituted by at least one hetero atom selected from the group consisting of N, O, S, P and combination thereof.

As indicated in Chemical Formula 1, the organic compound includes a carbazole moiety and a dibenzofuran or dibenzothiophene moiety (including Z) each of which linked to a central fused dibenzofuran or dibenzothiophene moiety (including X and Y). The carbazole moiety has high affinity to holes so that it has a p-type property. On the other hand, both the dibenzofuran/dibenzothiophene moiety and the central fused dibenzofuran/dibenzothiophene moiety have high affinity to electron so that they have an n-type property. The dibenzofuran/dibenzothiophene moiety allows a LUMO (Lowest Unoccupied Molecular Orbital) energy level of the molecule to be adjusted, thus the organic compound having the structure of Chemical Formula 1 can have a bipolar property. The central fused hetero aromatic moiety allows a HOMO (Highest Occupied Molecular Orbital) state of the molecule to be separated from a LUMO state, thus the organic compound has high excited triplet energy level, and thereby improving its exciton confinement efficiency.

In one exemplary aspect, the $C_6$-$C_{30}$ aromatic group in each of $R_1$ to $R_{15}$ can comprise a $C_6$-$C_{30}$ aryl group, a $C_7$-$C_{30}$ aryl alkyl group, a $C_6$-$C_{30}$ aryloxyl group and a $C_6$-$C_{30}$ aryl amino group. In another exemplary aspect, the $C_3$-$C_{30}$ hetero aromatic group in each of $R_1$ to $R_{15}$ can comprise a $C_3$-$C_{30}$ hetero aryl group, a $C_4$-$C_{30}$ hetero aryl alkyl group, a $C_3$-$C_{30}$ hetero aryloxyl group and a $C_3$-$C_{30}$ hetero aryl amino group.

As an example, the $C_6$-$C_{30}$ aryl group in each of $R_1$ to $R_{15}$ can comprise independently, but is not limited to, an unfused or fused aryl group such as phenyl, biphenyl, terphenyl, naphthyl, anthracenyl, pentalenyl, indenyl, indeno-indenyl, heptalenyl, biphenylenyl, indacenyl, phenalenyl, phenanthrenyl, benzophenanthrenyl, dibenzophenanthrenyl, azulenyl, pyrenyl, fluoranthenyl, triphenylenyl, chrysenyl, tetraphenylenyl, tetracenyl, pleiadenyl, picenyl, pentaphenylenyl, pentacenyl, fluorenyl, indeno-fluorenyl and spirofluorenyl.

In another exemplary aspect, the $C_3$-$C_{30}$ hetero aryl group in each of $R_1$ to $R_{15}$ can comprise independently, but is not limited to, an unfused or fused hetero aryl group such as pyrrolyl, pyridyl, pyridinyl, pyrimidinyl, pyrazinyl, pyridazinyl, triazinyl, tetrazinyl, imidazolyl, pyrazolyl, indolyl, iso-indolyl, indazolyl, indolizinyl, pyrrolizinyl, carbazolyl, benzocarbazolyl, dibenzocarbazolyl, indolo-carbazolyl, indeno-carbazolyl, benzofuro-carbazolyl, benzothieno-carbazolyl, carbolinyl, quinolinyl, iso-quinolinyl, phthlazinyl, quinoxalinyl, cinnolinyl, quinazolinyl, quinolizinyl, purinyl, benzoquinolinyl, benzoiso-quinolinyl, benzoquinazolinyl, benzoquinoxalinyl, acridinyl, phenazinyl, phenoxazinyl, phenothiazinyl, phenanthrolinyl, perimidinyl, phenanthridinyl, pteridinyl, naphthyridinyl, furanyl, pyranyl, oxazinyl, oxazolyl, oxadiazolyl, triazolyl, dioxinyl, benzofuranyl, dibenzofuranyl, thiopyranyl, xanthenyl, chromenyl, iso-chromenyl, thioazinyl, thiophenyl, benzothiophenyl, dibenzothiophenyl, difuro-pyrazinyl, benzofuro-dibenzofuranyl, benzothieno-benzothiophenyl, benzothieno-dibenzothiophenyl, benzothieno-benzofuranyl, benzothieno-dibenzofuranyl, xanthene-linked spiro acridinyl, dihydroacridinyl substituted with at least one $C_1$-$C_{10}$ alkyl and N-substituted spiro fluorenyl.

In one exemplary aspect, when each of $R_1$ to $R_{15}$ is the aromatic group or the hetero aromatic group, the aromatic group or the hetero aromatic group can consist of 1 to three aromatic rings or hetero aromatic rings. When the number of the aromatic or hetero aromatic ring becomes increase, the whole organic compound has too long conjugated structure so that its bandgap can be excessively reduced. As an example, when each of $R_1$ to $_{15}$ is the aromatic or the hetero aromatic group, each of $R_1$ to $_{15}$ can be independently, but is not limited to, phenyl, biphenyl, pyrrolyl, triazinyl, imidazolyl, pyrazolyl, pyridyl, pyridinyl, pyrazinyl, pyrimidinyl, pyridazinyl, furanyl, benzofuranyl, dibenzofuranyl, thiophenyl, benzothiophenyl, dibenzothiophenyl or carbazolyl.

In another alternative aspect, two adjacent groups among $R_1$ to $R_{15}$ can from a $C_6$-$C_{20}$ aromatic ring or a $C_3$-$C_{20}$ hetero aromatic ring. As an example, when each of two adjacent groups among $R_1$ to $R_{15}$ forms independently the fused aromatic ring or the fused hetero aromatic ring, the newly formed fused aromatic ring or the hetero aromatic ring can comprise, but is not limited to, an aryl ring such as a benzene ring and/or a naphthalene ring, or a hetero aryl ring such as a pyridine ring, a pyrimidine ring and/or a carbazole ring.

As an example, when two adjacent groups among $R_1$ to $R_8$ form the aromatic or hetero aromatic ring, the carbazole moiety in Chemical Formula 1 can form, but is not limited to, a benzocarbazole moiety, a dibenzocarbazole moiety, a benzofuro-carbazole moiety, a benzothieno-carbazole moiety, an indeno-carbazole moiety (e.g. dihydro-dimethyl-indeno-carbazole moiety) and an indolo-carbazole moiety.

Also, when two adjacent groups among $R_9$ to $R_{15}$ form the aromatic or hetero aromatic ring, the dibenzofuran/dibenzothiophene moiety in Chemical Formula 1 can form, but is not limited to, a pyrido-dibenzofuran moiety, a pyrido-dibenzothiophene moiety, an indeno-dibenzofuran moiety, an indeno-dibenzothiophene moiety, an indolo-dibenzofuran moiety and an indolo-dibenzothiophene moiety.

The organic compound having the structure of Chemical Formulae 1 and 2 includes a carbazole moiety having a p-type property and at least one dibenzofuran and/or dibenzothiophene moiety having an n-type property, thus the organic compound has a bipolar property that has high affinity to holes and electrons. When the organic compound is applied into an emissive layer of the OLED, the recombination zone among holes and electrons are formed in the center region of the EML, not an interface between the EML and the ETL or HBL.

Also, each of the carbazole moiety and the dibenzofuran/dibenzothiophene moiety includes a center five-member ring which is fused with a six-member ring at both sides. Both the carbazole moiety and the dibenzofuran/dibenzothiophene moiety has a rigid chemical conformation, thus the organic compound having the structure of Chemical Formula 1 has excellent thermal resistance. Particularly, the p-type group and the n-type group are bonded asymmetrically to the center core in the organic compound so as to maximize amorphous property, thus the organic compound has very excellent thermal resistance. The organic compound rarely deteriorated by Joule's heat that is generated in driving the OLED. Accordingly, the OLED including the organic compound can implement excellent luminous efficiency and lengthen its luminous lifetime due to preventing the destruction thereof.

The organic compound includes plural dibenzofuran/dibenzothiophene moieties which includes the central 5-member ring which is fused with a six-member ring at both sides. Particularly, the central linker of the molecule is designed to have at least five aromatic or hetero aromatic rings, thus the organic compound can have high excited triplet energy level and can improve its exciton confinement efficiency.

As an example, the organic compound having the structure of Chemical Formula 1 has an excited triplet energy level higher than an excited triplet energy level of fluorescent or phosphorescent material, for example, delayed fluorescent material, and an energy level bandgap between HOMO energy level and LUMO energy level wider than the energy level of fluorescent or phosphorescent material, for example, delayed fluorescent material. When the organic compound is applied into an EML as a host, the exciton energy of the host can be efficiently transferred to the fluorescent or phosphorescent material as a dopant due to efficient exciton confinement, and exciton quenching due to an interaction between singlet and/or triplet excitons of the host or the dopant and hole (or electro)-polarons can be minimized. As an example, when the organic compound and the delayed fluorescent material are included in the EML, the OLED can lower its driving voltage and power consumption. In this case, the stress due to the driving voltage raise applied into the OLED is decreased, thus the OLED can increase its luminous lifetime.

As a result, since the lifetime of the OLED can be prevented from being reduced by electro-oxidation and photo-oxidation, the OLED can implement long lifetime. Since the organic compound can transfer efficiently the exciton energy to other luminous materials without losing the exciton energy in the luminescence process, high luminous efficiency can be realized. If necessary, the color purity of the emission wavelength can be improved by using a fluorescent or phosphorescent material with narrow FWHM (full-width at half maximum).

In one exemplary aspect, the organic compound can have, but is not limited to, an excited singlet energy level $S_1^H$ of about 2.9 eV or more and an excited triplet energy level $T_1^H$ of about 2.8 eV or more. Also, the organic compound can have, but is not limited to, a HOMO energy level between about −5.0 eV and about −6.5 eV, preferably between about −5.5 eV and about −6.2 eV. The organic compound can have, but is not limited to, a LUMO energy level between about −1.8 eV and about −3.0 eV, preferably about −2.0 eV and about −2.8 eV. In this case, the energy level bandgap $E_g$ between the HOMO energy level and the LUMO energy level of the organic compound can be between about 3.0 eV and about 4.0 eV, preferably between about 3.0 eV and 3.7 eV.

In one exemplary aspect, the five-member ring including X and the five-member ring including Y in the central fused hetero aromatic ring can be linked symmetrically to the benzene ring therebetween. For example, such an organic compound can have the following structure of Chemical Formula 2:

[Chemical Formula 2]
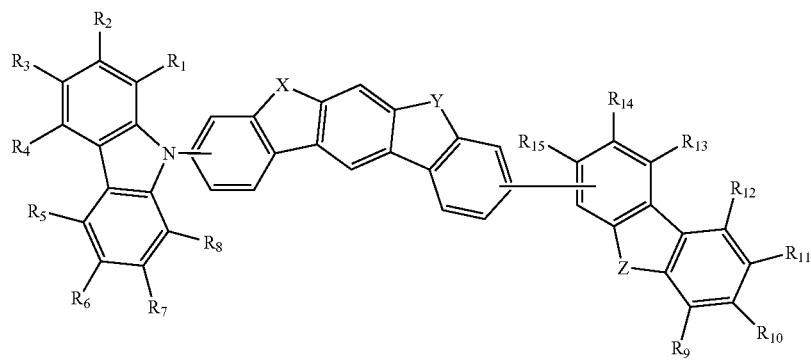
In Chemical Formula 2, each of $R_1$ to $R_{15}$, X, Y and Z is identical as defined in Chemical Formula 1.
As an example, the organic compound having the structure of Chemical Formula 2 can comprise, but is not limited to, any organic compound having the following structure of Chemical Formula 3:
[Chemical Formula 3]
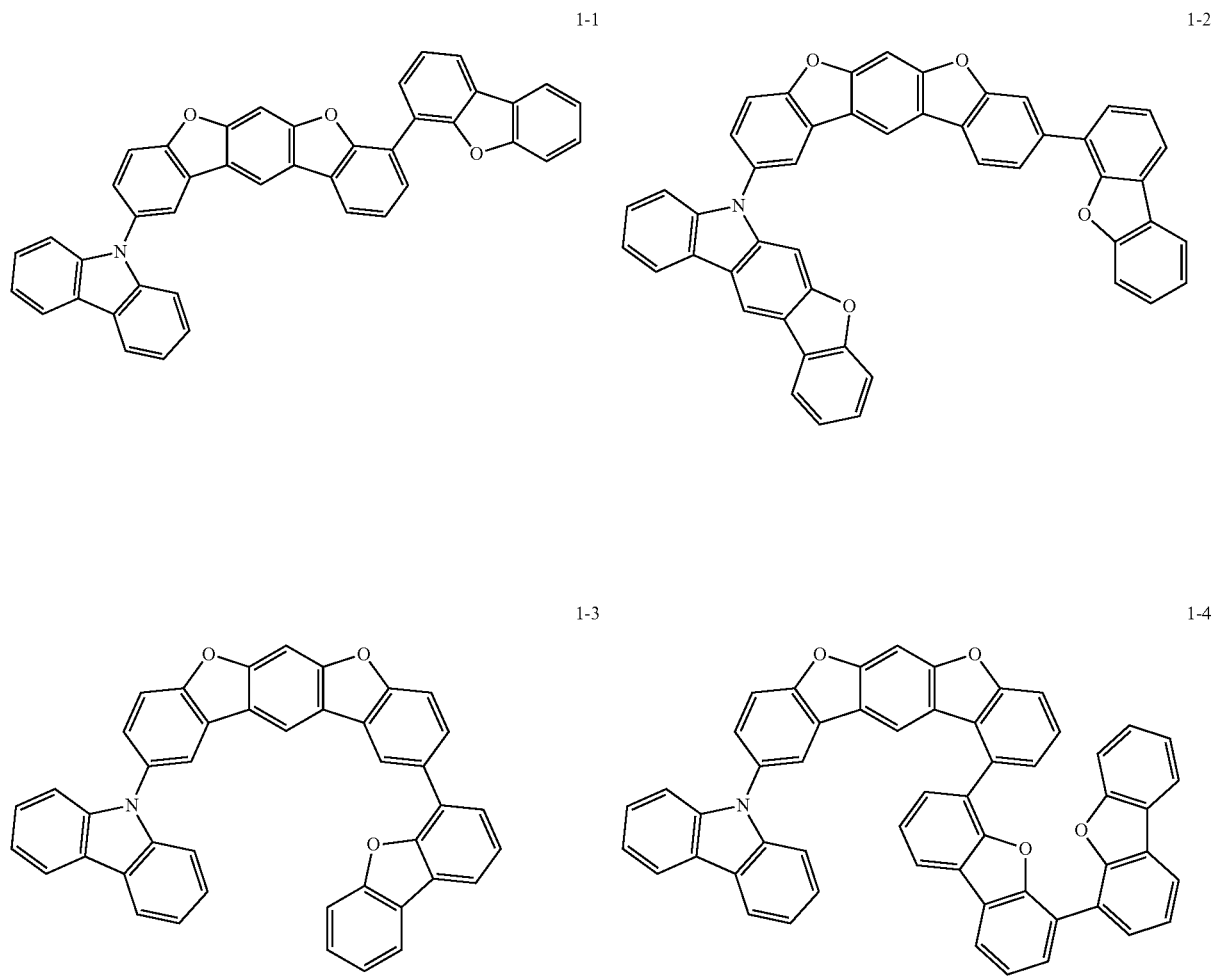

1-5
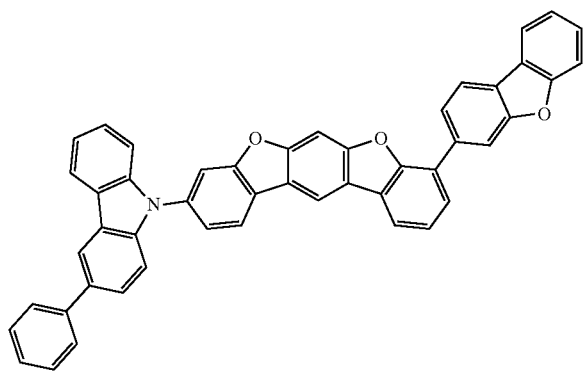
1-6
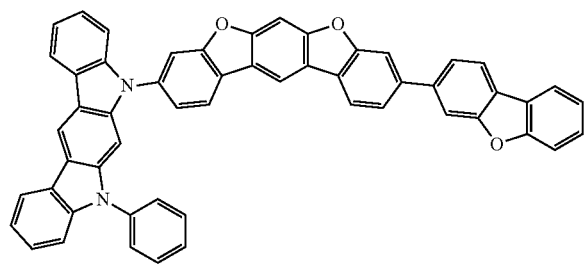
1-7
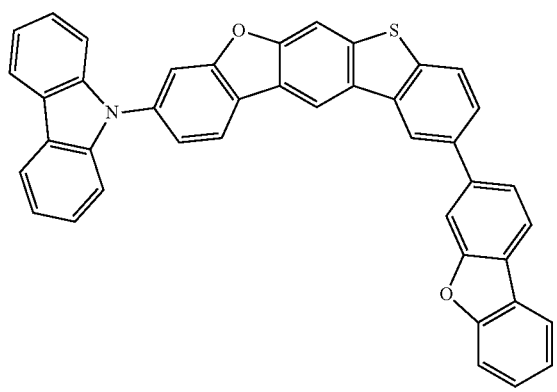
1-8
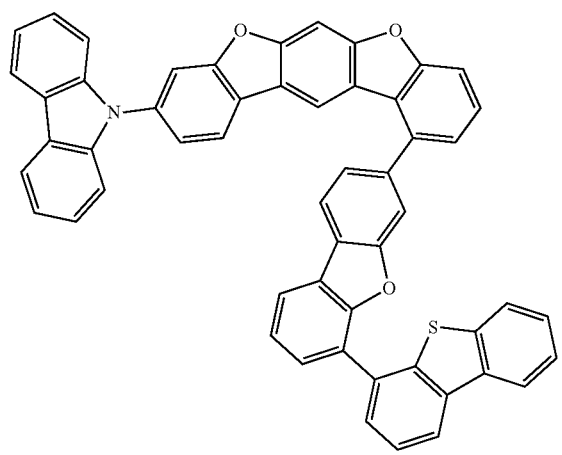
1-9
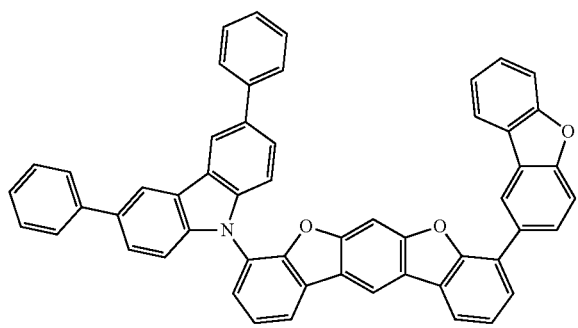
1-10
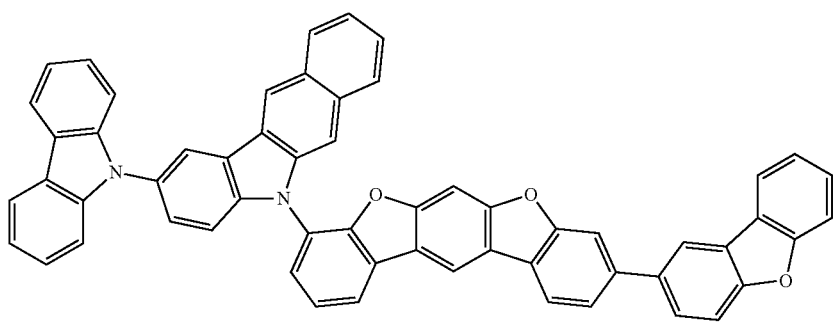

-continued
1-11
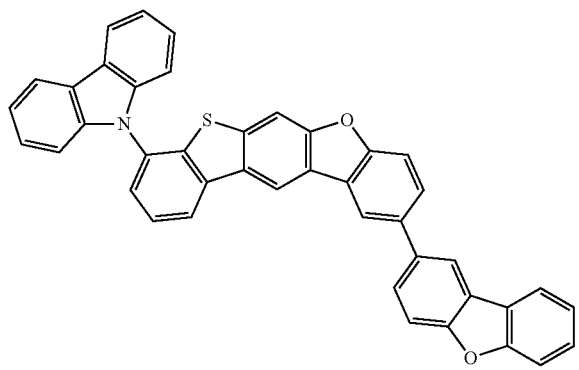
1-12
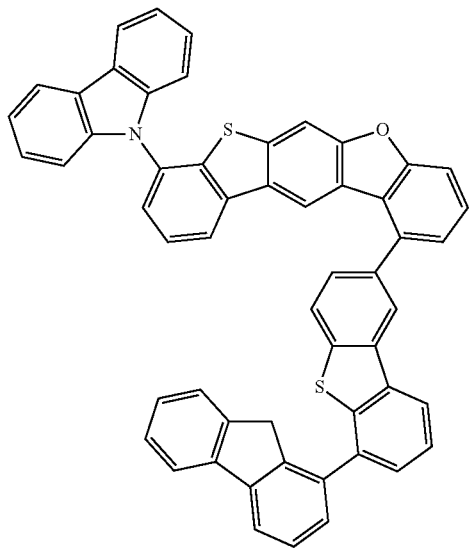
1-13
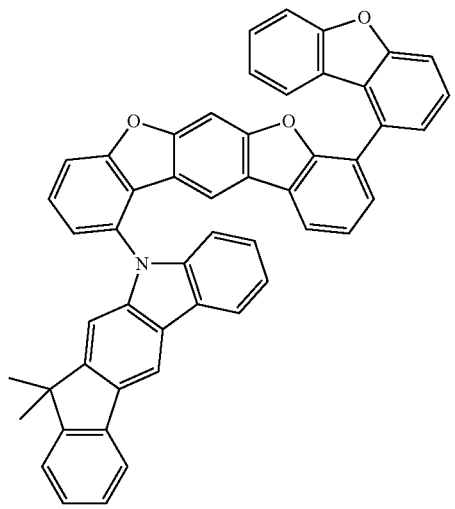
1-14
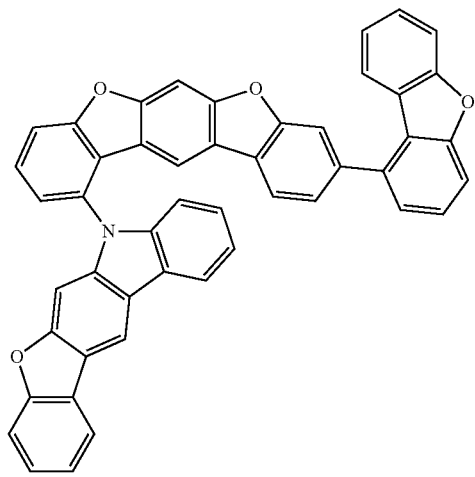
1-15
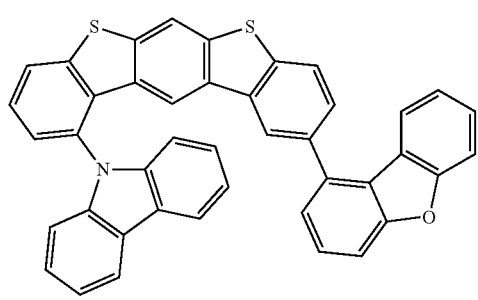
1-16
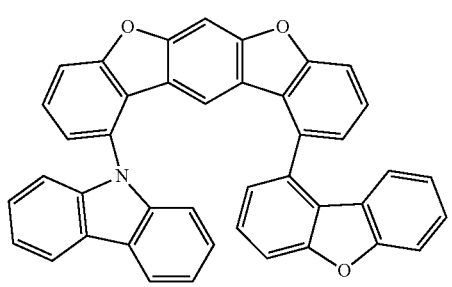

-continued 1-17

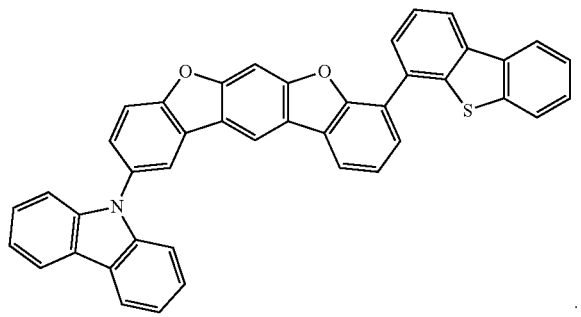

In another exemplary aspect, the five-member ring including X and the five-member ring including Y in the central fused hetero aromatic ring can be linked asymmetrically to the benzene ring therebetween. For example, such an organic compound can have the following structure of Chemical Formula 4:

[Chemical Formula 4]

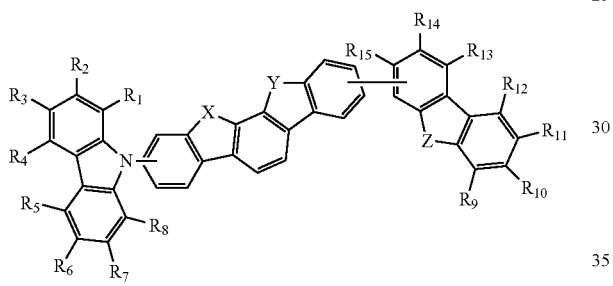

In Chemical Formula 4, each of $R_1$ to $R_{15}$, X, Y and Z is identical as defined in Chemical Formula 1.

As an example, the organic compound having the structure of Chemical Formula 4 can comprise, but is not limited to, any organic compound having the following structure of Chemical Formula 5:

[Chemical Formula 5]

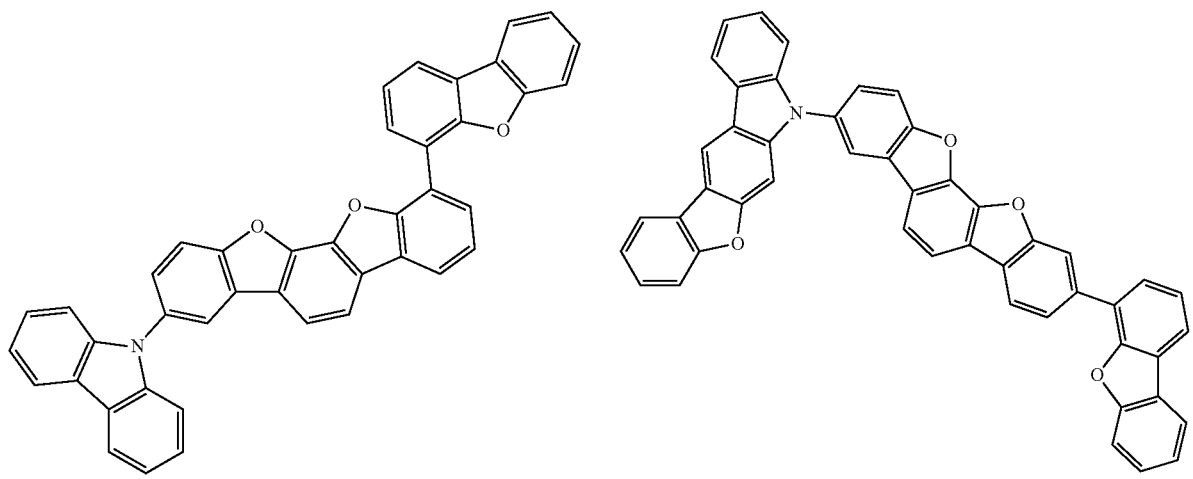

2-1  2-2

-continued
2-3
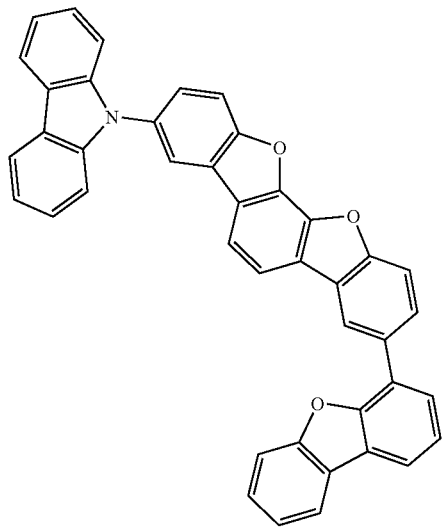
2-4
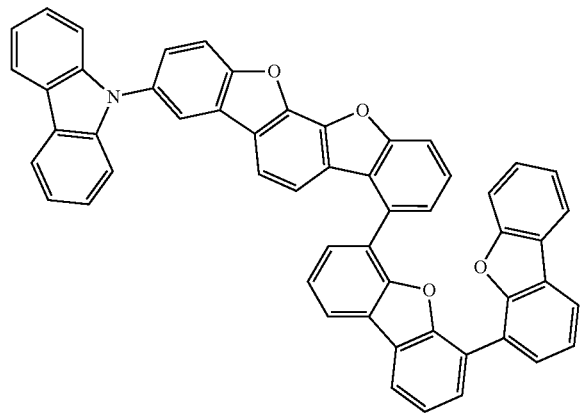
2-5
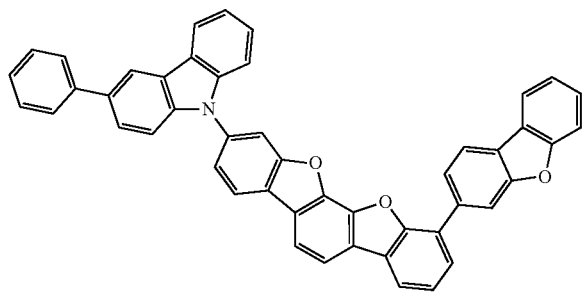
2-6
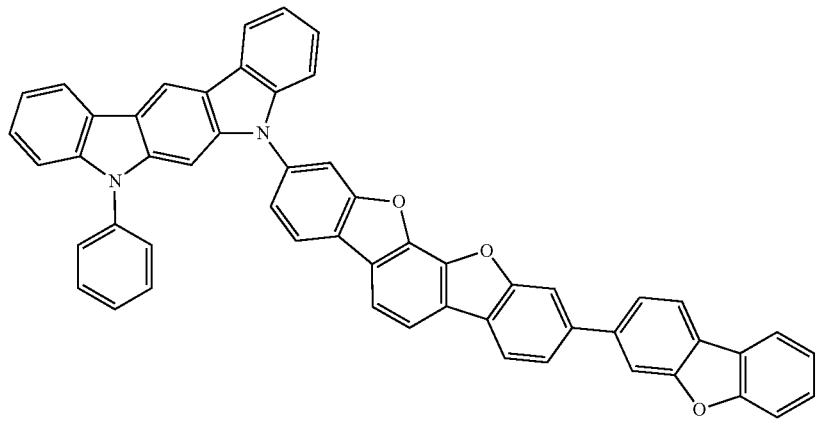
2-7
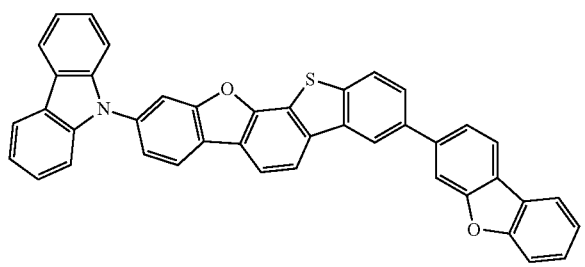
2-8
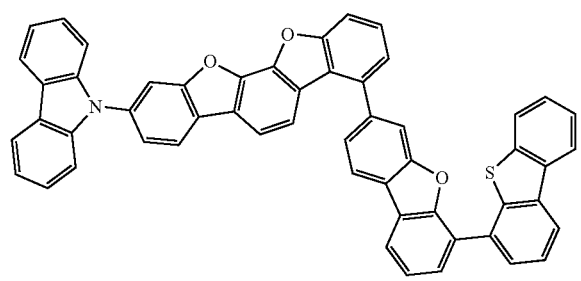

-continued
2-9
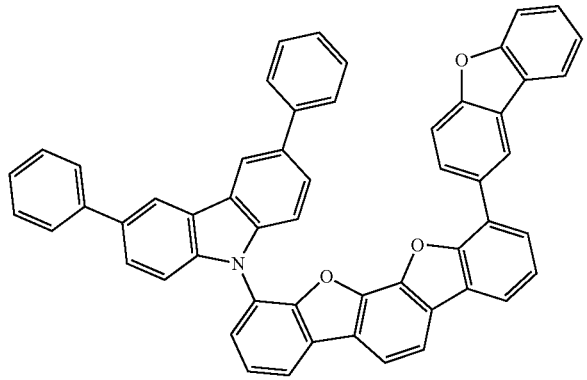
2-10
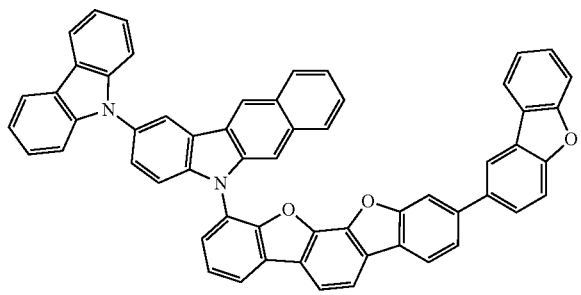
2-11
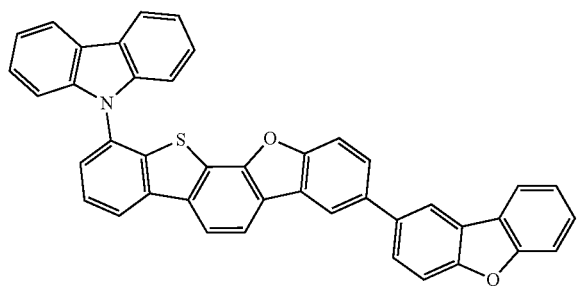
2-12
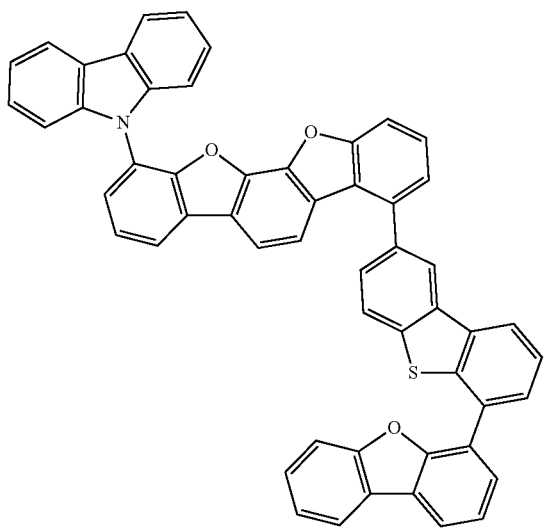
2-13
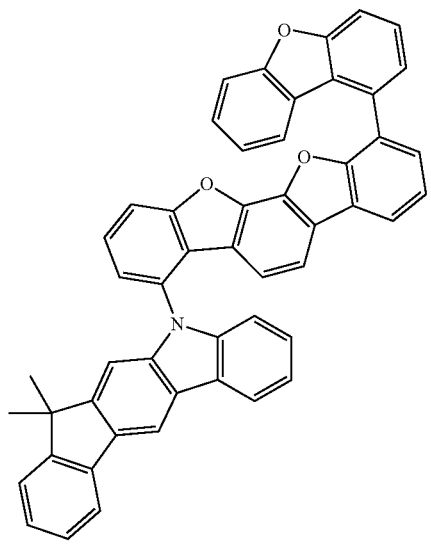
2-14
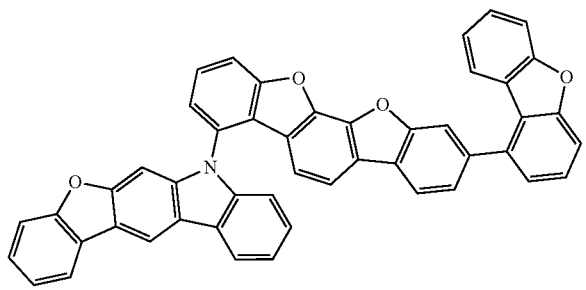

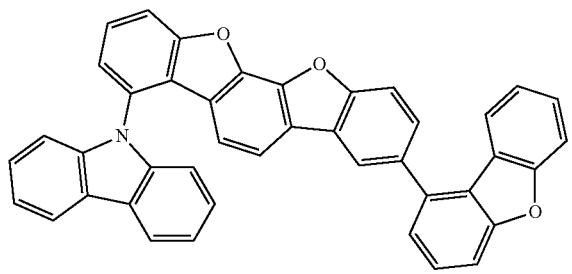

2-15

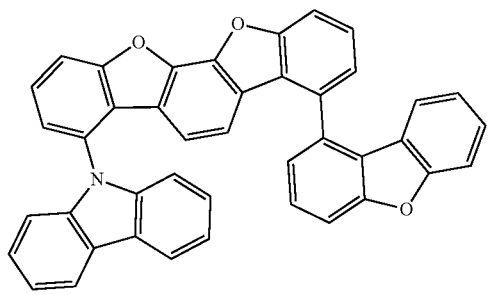

2-16

Another organic compound in which the five-member ring including X and the five-member ring including Y in the central fused hetero aromatic ring are linked asymmetrically to the benzene ring therebetween can have the following structure of Chemical Formula 6:

[Chemical Formula 6]

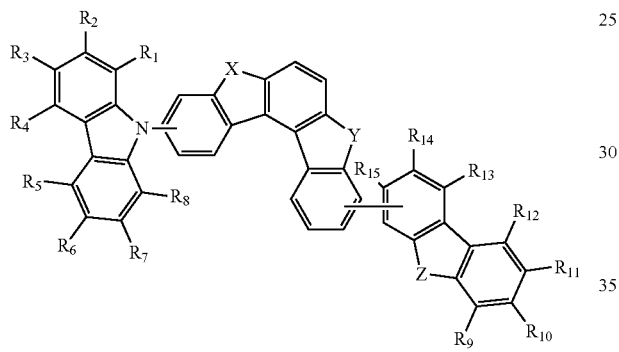

In Chemical Formula 6, each of $R_1$ to $R_{15}$, X, Y and Z is identical as defined in Chemical Formula 1.

As an example, the organic compound having the structure of Chemical Formula 6 can comprise, but is not limited to, any organic compound having the following structure of Chemical Formula 7:

[Chemical Formula 7]

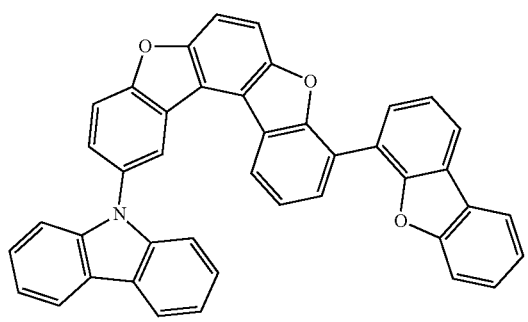

3-1

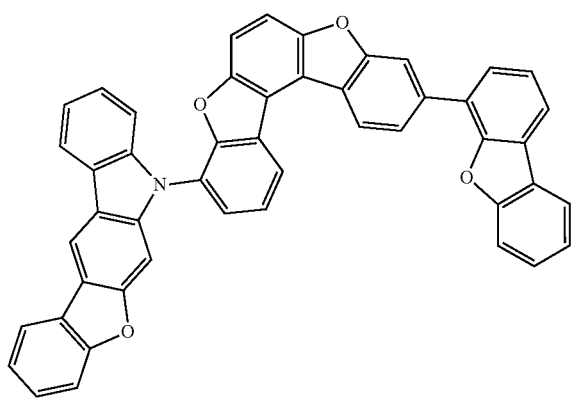

3-2

-continued
3-3
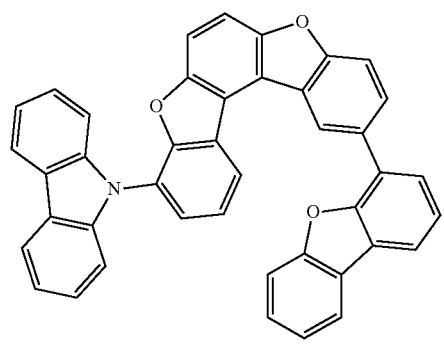
3-4
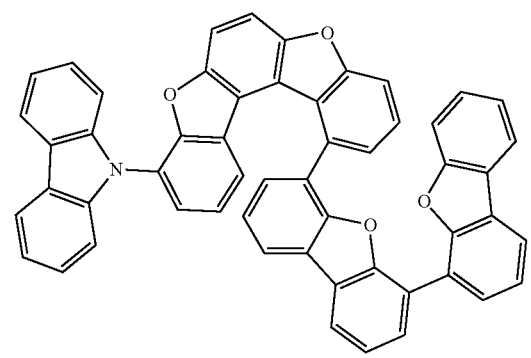
3-5
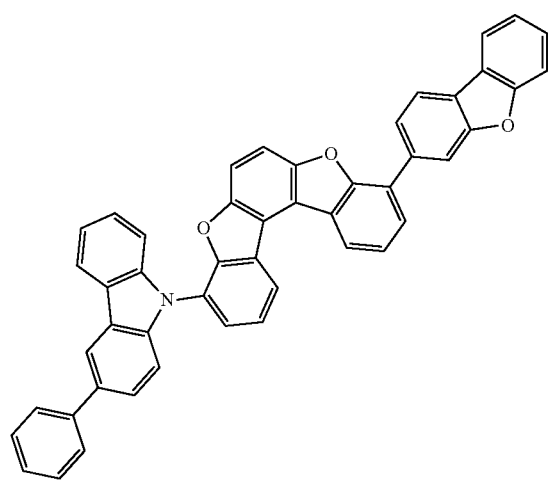
3-6
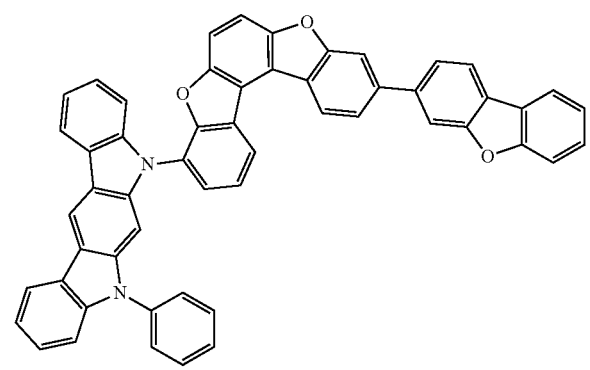
3-7
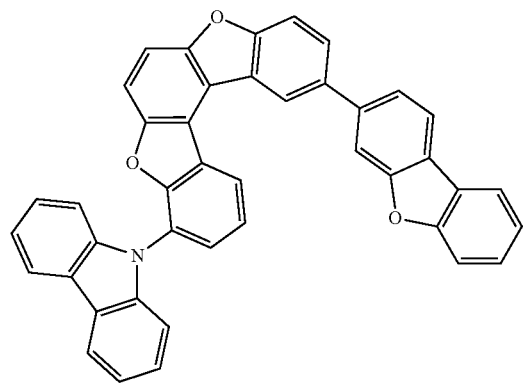
3-8
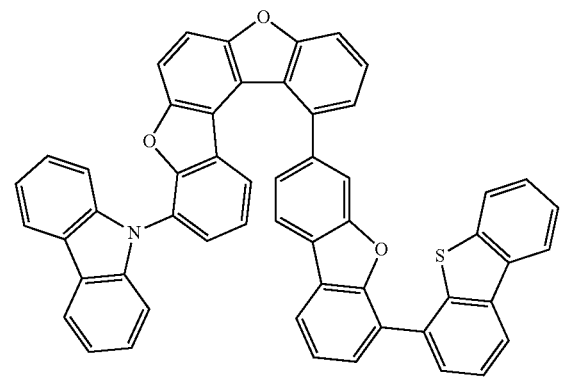
3-9
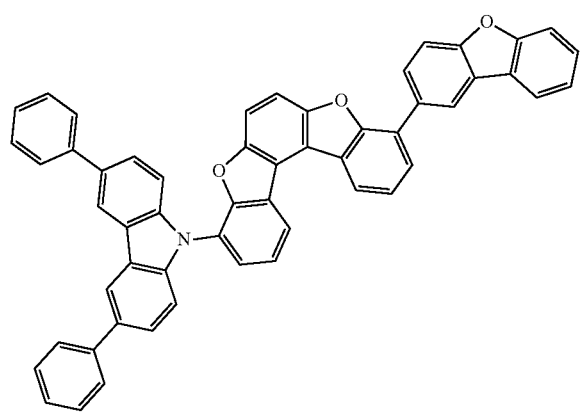

-continued
3-10
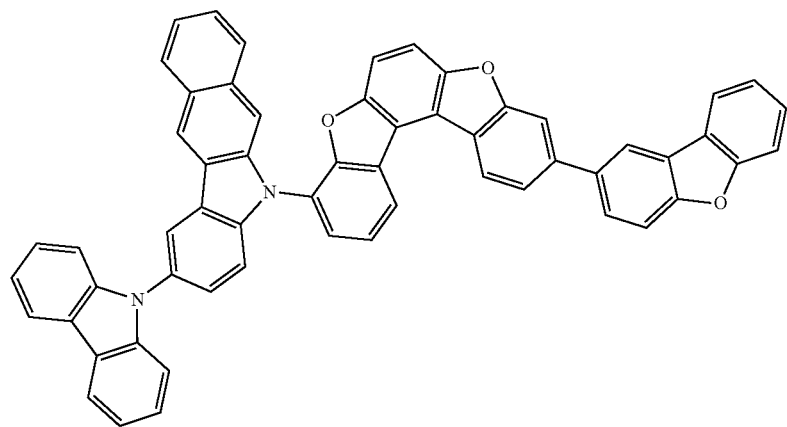
3-11
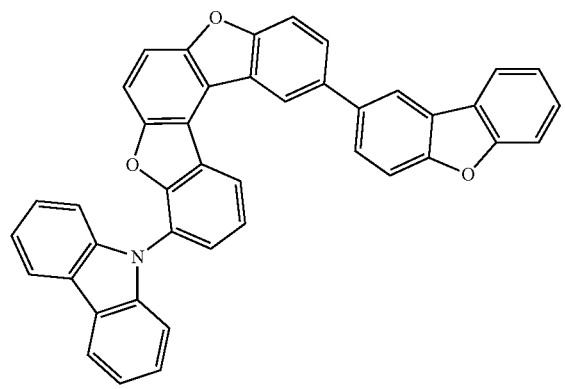
3-12
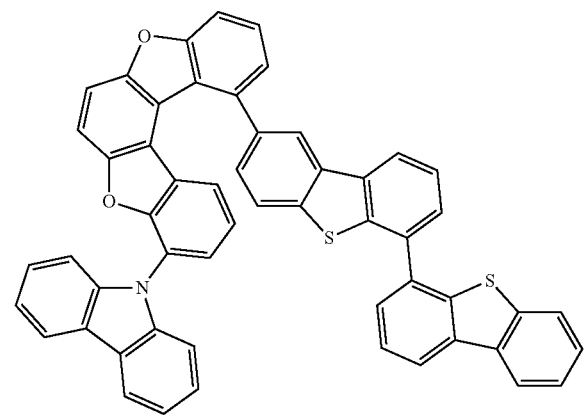
3-13
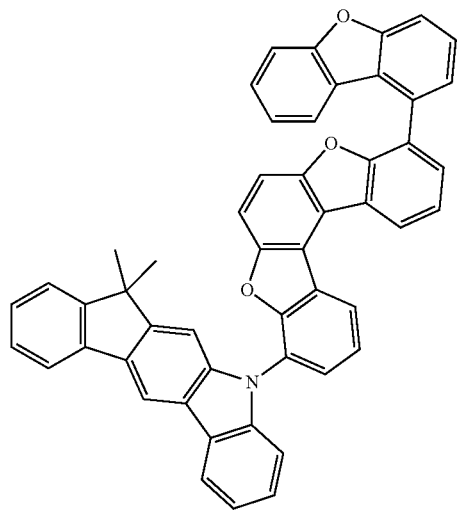
3-14
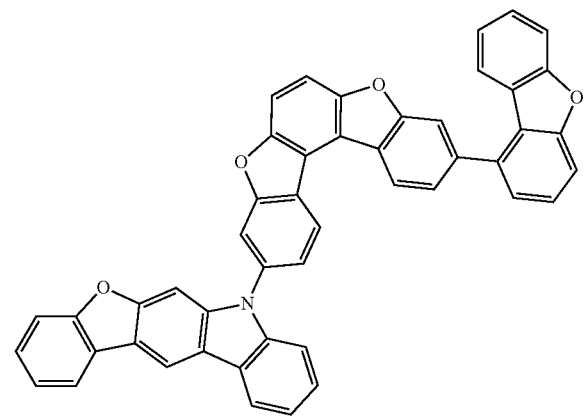

3-15

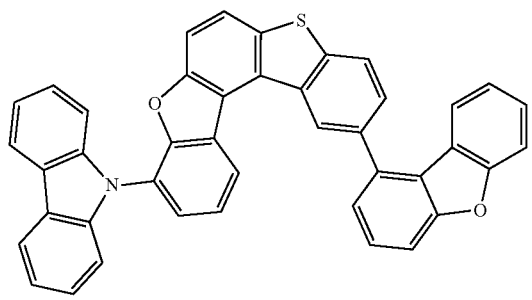

3-16

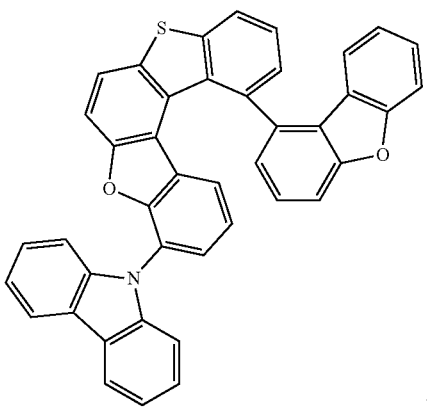

In still another exemplary aspect, the positions of the X and the Y in the central fused hetero aromatic ring can be linked to the benzene ring therebetween in opposite direction. For example, such an organic compound can have the following structure of Chemical Formula 8:

[Chemical Formula 8]

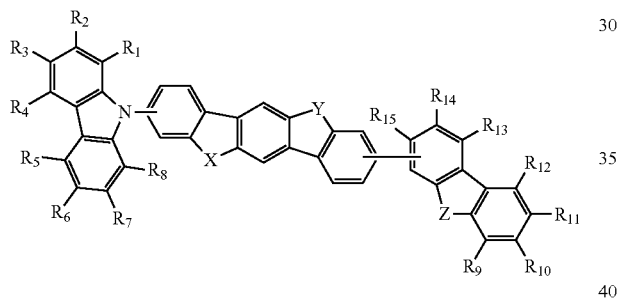

In Chemical Formula 8, each of $R_1$ to $R_{15}$, X, Y and Z is identical as defined in Chemical Formula 1.

As an example, the organic compound having the structure of Chemical Formula 8 can comprise, but is not limited to, any organic compound having the following structure of Chemical Formula 9:

[Chemical Formula 9]

4-1

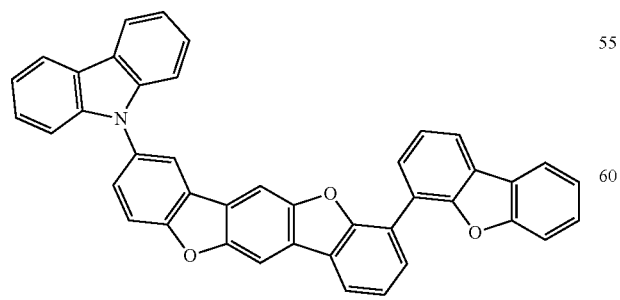

-continued 4-2

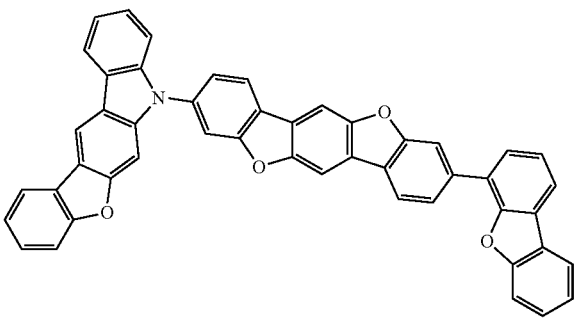

4-3

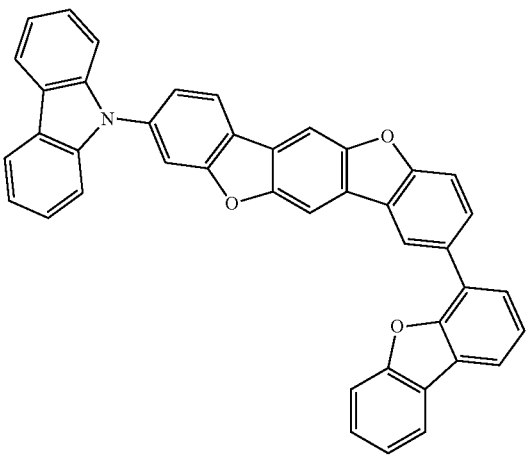

4-4
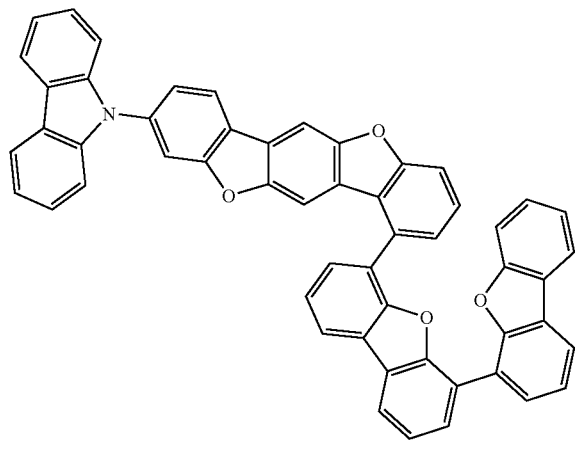
4-5
4-6
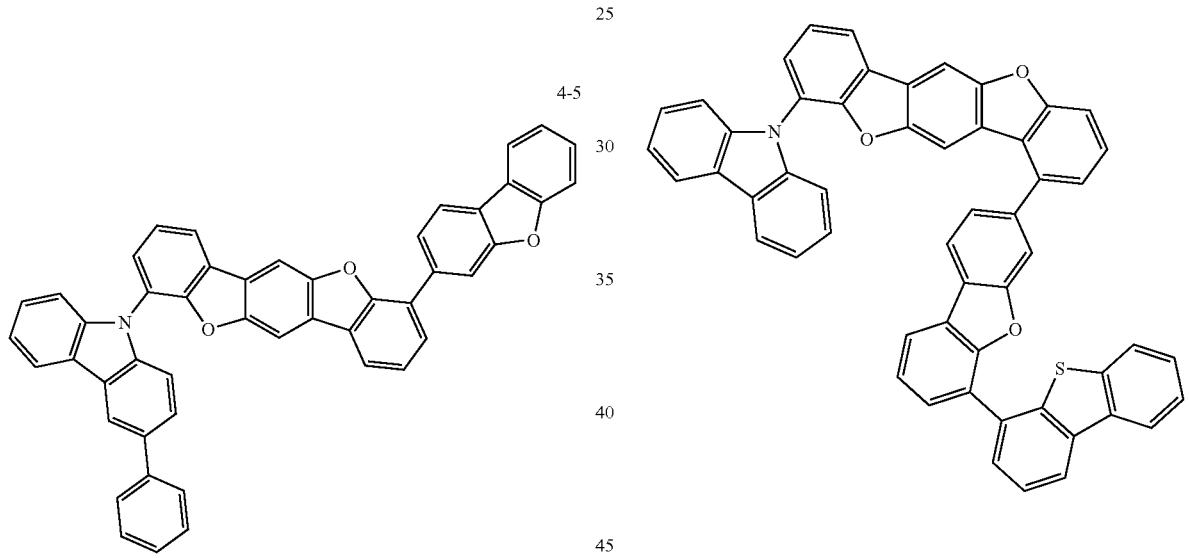
4-7
4-8
4-9
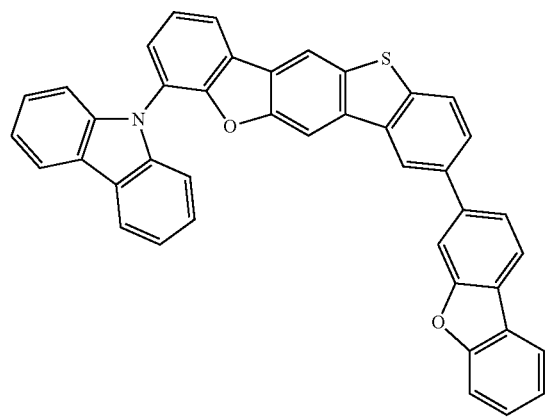
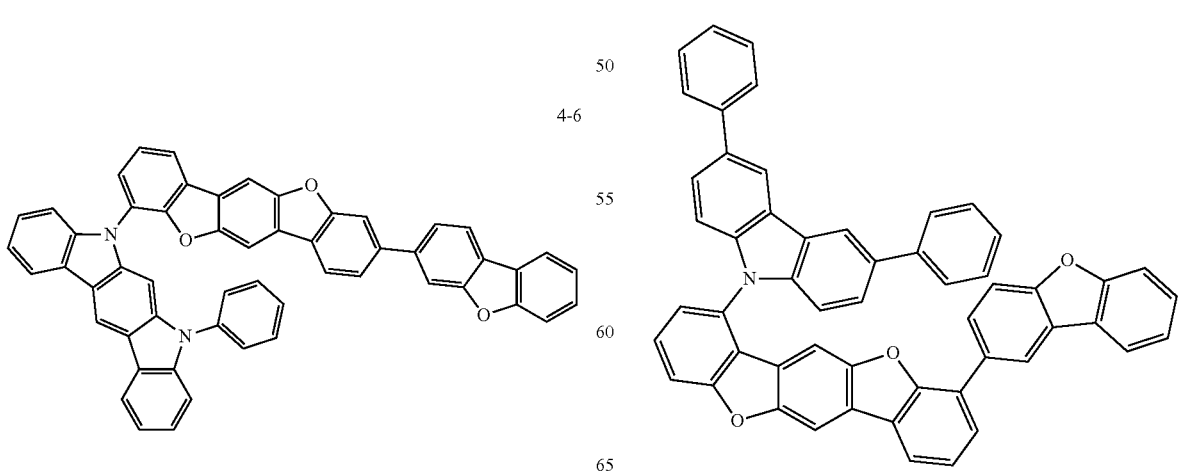

4-10

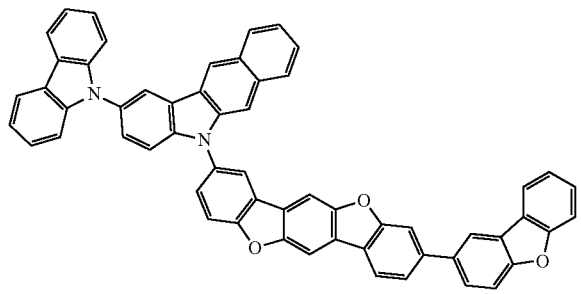

4-11

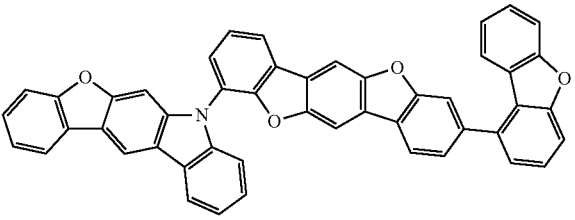

4-14

4-15

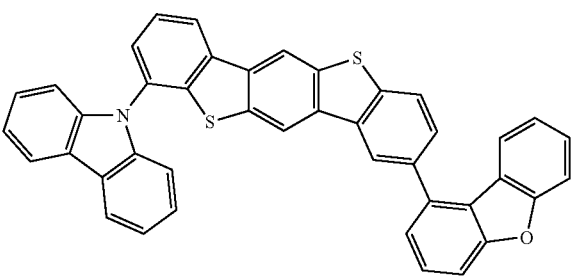

4-16

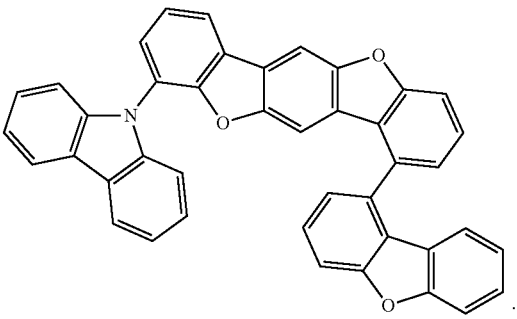

4-12

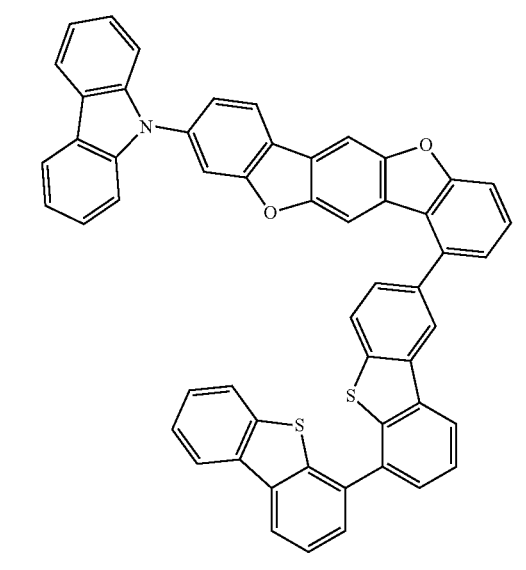

4-13

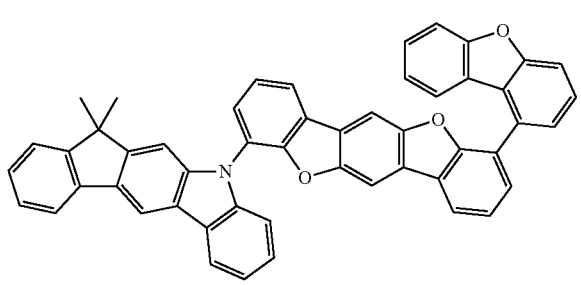

[Organic Light Emitting Device and OLED]

The organic compound having the structure of Chemical Formulae 1 to 9 has excellent thermal property and luminous property. The organic compound can be applied into an emissive layer of the OLED, so that it can lower the driving voltage, enhance the luminous efficiency and improve luminous lifetime of the OLED. The OLED of the present disclosure can be applied to an organic light emitting device such as an organic light emitting display device or an organic light emitting illumination device. An organic light emitting display device including the OLED will be explained. FIG. 1 is a schematic cross-sectional view of an organic light emitting display device in accordance with one exemplary aspect of the present disclosure. All the components of the organic light emitting display device according to all embodiments of the present disclosure are operatively coupled and configured.

As illustrated in FIG. 1, an organic light emitting display device 100 includes a substrate 110, a thin-film transistor Tr on the substrate 110, and an organic light emitting diode (OLED) D connected to the thin film transistor Tr. For example, the organic light emitting display device 100 preferably can include a plurality of pixels each having the configuration shown in FIG. 1.

The substrate 110 can include, but is not limited to, glass, thin flexible material and/or polymer plastics. For example, the flexible material can be selected from the group, but is not limited to, polyimide (PI), polyethersulfone (PES), polyethylenenaphthalate (PEN), polyethylene terephthalate (PET), polycarbonate (PC) and combination thereof. The substrate 110, over which the thin film transistor Tr and the OLED D are arranged, form an array substrate.

A buffer layer 122 can be disposed over the substrate 110, and the thin film transistor Tr is disposed over the buffer layer 120. The buffer layer 122 can be omitted.

A semiconductor layer 120 is disposed over the buffer layer 122. In one exemplary aspect, the semiconductor layer 120 can include, but is not limited to, oxide semiconductor materials. In this case, a light-shield pattern can be disposed under the semiconductor layer 120, and the light-shield pattern can prevent light from being incident toward the semiconductor layer 120, and thereby, preventing the semiconductor layer 120 from being deteriorated by the light. Alternatively, the semiconductor layer 120 can include, but is not limited to, polycrystalline silicon. In this case, opposite edges of the semiconductor layer 120 can be doped with impurities.

A gate insulating layer 124 formed of an insulating material is disposed on the semiconductor layer 120. The gate insulating layer 124 can include, but is not limited to, an inorganic insulating material such as silicon oxide ($SiO_x$) or silicon nitride ($SiN_x$).

A gate electrode 130 made of a conductive material such as a metal is disposed over the gate insulating layer 124 so as to correspond to a center of the semiconductor layer 120. While the gate insulating layer 124 is disposed over a whole area of the substrate 110 in FIG. 1, the gate insulating layer 124 can be patterned identically as the gate electrode 130.

An interlayer insulating layer 132 formed of an insulating material is disposed on the gate electrode 130 with covering over an entire surface of the substrate 110. The interlayer insulating layer 132 can include, but is not limited to, an inorganic insulating material such as silicon oxide ($SiO_x$) or silicon nitride ($SiN_x$), or an organic insulating material such as benzocyclobutene or photo-acryl.

The interlayer insulating layer 132 has first and second semiconductor layer contact holes 134 and 136 that expose both sides of the semiconductor layer 120. The first and second semiconductor layer contact holes 134 and 136 are disposed over opposite sides of the gate electrode 130 with spacing apart from the gate electrode 130. The first and second semiconductor layer contact holes 134 and 136 are formed within the gate insulating layer 124 in FIG. 1. Alternatively, the first and second semiconductor layer contact holes 134 and 136 are formed only within the interlayer insulating layer 132 when the gate insulating layer 124 is patterned identically as the gate electrode 130.

A source electrode 144 and a drain electrode 146, which are formed of conductive material such as a metal, are disposed on the interlayer insulating layer 132. The source electrode 144 and the drain electrode 146 are spaced apart from each other with respect to the gate electrode 130, and contact both sides of the semiconductor layer 120 through the first and second semiconductor layer contact holes 134 and 136, respectively.

The semiconductor layer 120, the gate electrode 130, the source electrode 144 and the drain electrode 146 constitute the thin film transistor Tr, which acts as a driving element. The thin film transistor Tr in FIG. 1 has a coplanar structure in which the gate electrode 130, the source electrode 144 and the drain electrode 146 are disposed over the semiconductor layer 120. Alternatively, the thin film transistor Tr can have an inverted staggered structure in which a gate electrode is disposed under a semiconductor layer and a source and drain electrodes are disposed over the semiconductor layer. In this case, the semiconductor layer can comprise amorphous silicon.

A gate line and a data line, which cross each other to define a pixel region, and a switching element, which is connected to the gate line and the data line is, can be further formed in the pixel region of FIG. 1. The switching element is connected to the thin film transistor Tr, which is a driving element. Besides, a power line is spaced apart in parallel from the gate line or the data line, and the thin film transistor Tr can further include a storage capacitor configured to constantly keep a voltage of the gate electrode for one frame.

In addition, the organic light emitting display device 100 can include a color filter that comprises dyes or pigments for transmitting specific wavelength light of light emitted from the OLED D. For example, the color filter can transmit light of specific wavelength such as red (R), green (G) and/or blue (B). Each of red, green, and blue color filter can be formed separately in each pixel region. In this case, the organic light emitting display device 100 can implement full-color through the color filter.

For example, when the organic light emitting display device 100 is a bottom-emission type, the color filter can be disposed on the interlayer insulating layer 132 with corresponding to the OLED D. Alternatively, when the organic light emitting display device 100 is a top-emission type, the color filter can be disposed over the OLED D, that is, a second electrode 230.

In addition, the organic light emitting device 100 can comprise a color conversion layer (not shown) converting a specific wavelength light among the light emitted from the OLED D to a long wavelength range light. The color conversion layer can comprise inorganic luminescent particles such as quantum dots or quantum rods. For example, the color conversion layer can be disposed over or below the OLED D.

A passivation layer 150 is disposed on the source and drain electrodes 144 and 146 over the whole substrate 110. The passivation layer 150 has a flat top surface and a drain contact hole 152 that exposes the drain electrode 146 of the thin film transistor Tr. While the drain contact hole 152 is disposed on the second semiconductor layer contact hole 136, it can be spaced apart from the second semiconductor layer contact hole 136.

The OLED D includes a first electrode 210 that is disposed on the passivation layer 150 and connected to the drain electrode 146 of the thin film transistor Tr. The OLED D further includes an emissive layer 220 and a second electrode 230 each of which is disposed sequentially on the first electrode 210.

The first electrode 210 is disposed in each pixel region. The first electrode 210 can be an anode and include a conductive material having a relatively high work function value. For example, the first electrode 210 can include, but is not limited to, a transparent conductive material such as indium tin oxide (ITO), indium zinc oxide (IZO), indium tin zinc oxide (ITZO), tin oxide (SnO), zinc oxide (ZnO), indium cerium oxide (ICO), aluminum doped zinc oxide (AZO), and the like.

In one exemplary aspect, when the organic light emitting display device 100 is a bottom-emission type, the first electrode may have a single-layered structure of transparent conductive oxide. Alternatively, when the organic light emitting display device 100 is a top-emission type, a reflective electrode or a reflective layer can be disposed under the first electrode 210. For example, the reflective electrode or the reflective layer can include, but are not limited to, silver (Ag) or aluminum-palladium-copper (APC) alloy. In addition, a bank layer 160 is disposed on the passivation layer 150 in order to cover edges of the first electrode 210. The bank layer 160 exposes a center of the first electrode 210. In the OLED D of a top-emission type, the first electrode 210 may have a triple-layered structure of ITO/Ag/ITO or ITO/APC/ITO.

An emissive layer 220 is disposed on the first electrode 210. In one exemplary aspect, the emissive layer 220 can have a single-layered structure of an emitting material layer (EML). Alternatively, the emissive layer 220 can further include a plural charge transfer layers. As an example, the emissive layer 220 can have a multiple-layered structure of a hole injection layer (HIL), a hole transport layer (HTL), an electron blocking layer (EBL), an EML, a hole blocking layer (HBL), an electron transport layer (ETL) and/or an electron injection layer (EIL) (see, FIGS. 2, 5, 7, 9 and 11). In one aspect, the emissive layer 220 can have one emitting part. Alternatively, the emissive layer 220 can have multiple emitting parts to form a tandem structure.

The emissive layer 220 comprises anyone having the structure of Chemical Formulae 1 to 9. As an example, the organic compound having the structure of Chemical Formulae 1 to 9 can be applied into a host in the EML, the ETL, the HBL and/or an N-type charge generation layer. In this case, the EML can further comprise at least one dopant as another luminous materials The second electrode 230 is disposed over the substrate 110 above which the emissive layer 220 is disposed. The second electrode 230 can be disposed over a whole display area and can include a conductive material with a relatively low work function value compared to the first electrode 210. The second electrode 230 can be a cathode. For example, the second electrode 230 can include, but is not limited to, aluminum (Al), magnesium (Mg), calcium (Ca), silver (Ag), alloy thereof or combination thereof such as aluminum-magnesium alloy (Al—Mg). When the organic light emitting display device 100 is a top-emission type, the second electrode 230 is this so as to have light-transmissive (semi-transmissive) property.

In addition, an encapsulation film 170 can be disposed over the second electrode 230 in order to prevent outer moisture from penetrating into the OLED D. The encapsulation film 170 can have, but is not limited to, a laminated structure of a first inorganic insulating film 172, an organic insulating film 174 and a second inorganic insulating film 176.

Moreover, the organic light emitting display device 100 may further comprise a polarizer in order to decrease external light reflection. For example, the polarizer can be a circular polarizer. When the organic light emitting display device 100 is a bottom-emission type, the polarizer may be disposed under the substrate 110. Alternatively, when the organic light emitting display device 100 is a top-emission type, the polarizer may be disposed over the encapsulation film 170. In addition, a cover window can be attached to the encapsulation film 170 or the polarizer in the organic light emitting display device 100 of the top-emission type. In this case, the substrate 110 and the cover window can have a flexible property, thus the organic light emitting display device 100 can be a flexible display device.

As described above, the emissive layer 220 of the OLED includes any organic compound having the structure of Chemical Formulae 1 to 9. The organic compound has excellent thermal and luminous properties, thus the OLED D can improve its luminous efficiency, lower its driving voltage and power consumption and implement long luminous lifetime by applying the organic compound.

Figure 2:
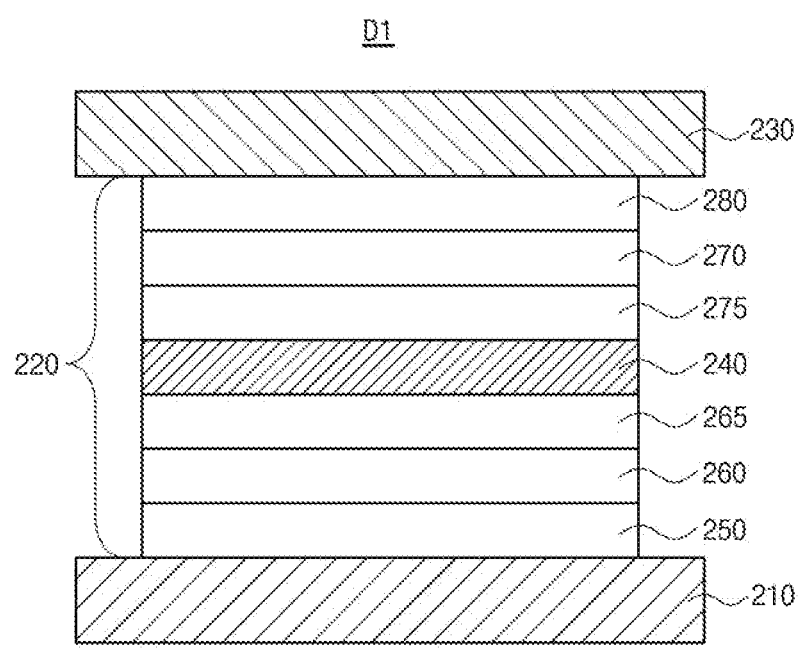
FIG. 2 is a schematic cross-sectional view illustrating an OLED in accordance with an exemplary aspect of the present disclosure.

Now, we will describe the OLED in more detail. FIG. 2 is a schematic cross-sectional view illustrating an OLED in accordance with an exemplary aspect of the present disclosure. As illustrated in FIG. 2, the OLED D1 includes first and second electrodes 210 and 230 facing each other and an emissive layer 220 having single emitting part disposed between the first and second electrodes 210 and 230. The organic light emitting display device 100 (FIG. 1) may include a red pixel region, a green pixel region and a blue pixel region, and the OLED D1 may be located in any one of the red green pixel region, the green pixel region and the blue pixel region.

In one exemplary aspect, the emissive layer 220 comprises an EML 240 disposed between the first and second electrodes 210 and 230. Also, the emissive layer 220 may comprise at least one of a HTL 260 disposed between the first electrode 210 and the EML 240 and an ETL 270 disposed between the second electrode 230 and the EML 240. Also, the emissive layer 220 may further comprise at least one of a HIL 250 disposed between the first electrode 210 and the HTL 260 and an EIL 280 disposed between the second electrode 230 and the ETL 270. Alternatively, the emissive layer 220 can further comprise a first exciton blocking layer, i.e. an EBL 265 disposed between the HTL 260 and the EML 240 and/or a second exciton blocking layer, i.e. a HBL 275 disposed between the EML 240 and the ETL 270.

The first electrode 210 can be an anode that provides a hole into the EML 240. The first electrode 210 can include, but is not limited to, a conductive material having a relatively high work function value, for example, a transparent conductive oxide (TCO). In an exemplary aspect, the first electrode 210 can include, but is not limited to, ITO, IZO, ITZO, SnO, ZnO, ICO, AZO, and the like.

The second electrode 230 can be a cathode that provides an electron into the EML 240. The second electrode 230 can include, but is not limited to, a conductive material having a relatively low work function values, i.e., a highly reflective material such as Al, Mg, Ca, Ag, alloy thereof, combination thereof, and the like.

The EML 240 can comprise a first compound H and a second compound TD. The first compound H can be a host and the second compound TD can be a dopant. As an example, the second compound TD can be fluorescent material, phosphorescent material or delayed fluorescent material. Hereinafter, we will describe the second compound TD as the delayed fluorescent material. For example, the organic compound having the structure of Chemical Formulae 1 to 8 can be used the first compound H in the EML 240. As an example, the EML 240 can emit red (R), green (G) or blue (B) light. We will describe the first compound and energy level relationships between the first and second compounds later.

The HIL 250 and the HTL 260 can be disposed sequentially between the first electrode 210 and the EML 240. The HIL 250 is disposed between the first electrode 210 and the HTL 260 and improves an interface property between the inorganic first electrode 210 and the organic HTL 260. In one exemplary aspect, the HIL 250 can include, but is not limited to, 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino)triphenylamine (2T-NATA), Copper phthalocyanine (CuPc), Tris(4-carbazoyl- 9-yl-phenyl)amine (TCTA), N,N'-Diphenyl-N,N'-bis(1-naphthyl)-1,1'-biphenyl-4,4"-diamine (NPB; NPD), 1,4,5,8,9,11-Hexaazatriphenylenehexacarbonitrile (Dipyrazino[2,3-f:2'3'-h]quinoxaline-2,3,6,7,10,11-hexacarbonitrile; HAT-CN), 1,3,5-tris[4-(diphenylamino)phenyl]benzene (TDAPB), poly(3,4-ethylenedioxythiophene)polystyrene sulfonate (PEDOT/PSS) and/or N-(biphenyl-4-yl)-9,9-dimethyl-N-(4-(9-phenyl-9H-carbazol-3-yl)phenyl)-9H-fluoren-2-amine. The HIL 250 can be omitted in compliance with a structure of the OLED D1.

The HTL 260 is disposed adjacently to the EML 240 between the first electrode 210 and the EML 240. In one exemplary aspect, the HTL 260 can include, but is not limited to, N,N'-Diphenyl-N,N'-bis(3-methylphenyl)-1,1'-biphenyl-4,4'-diamine (TPD), NPB, 4,4'-bis(N-carbazolyl)-1,1'-biphenyl (CBP), Poly[N,N'-bis(4-butylphenyl)-N,N'-bis(phenyl)-benzidine] (Poly-TPD), Poly[(9,9-dioctylfluorenyl-2,7-diyl)-co-(4,4'-(N-(4-sec-butylphenyl)diphenylamine))] (TFB), Di[4-(N,N-di-p-tolyl-amino)-phenyl]cyclohexane (TAPC), 3,5-Di(9H-carbazol-9-yl)-N,N-diphenylaniline (DCDPA), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The ETL 270 and the EIL 280 can be disposed sequentially between the EML 240 and the second electrode 230. The ETL 270 includes a material having high electron mobility so as to provide the EML 240 with electrons stably by fast electron transportation. In one exemplary aspect, the ETL 270 can comprise, but is not limited to, any one of oxadiazole-based compounds, triazole-based compounds, phenanthroline-based compounds, benzoxazole-based compounds, benzothiazole-based compounds, benzimidazole-based compounds, triazine-based compounds, and the like.

As an example, the ETL 270 can comprise, but is not limited to, tris-(8-hydroxyquinoline aluminum (Alq$_3$), 2-biphenyl-4-yl-5-(4-t-butylphenyl)-1,3,4-oxadiazole (PBD), spiro-PBD, lithium quinolate (Liq), 1,3,5-Tris(N-phenyl-benzimidazol-2-yl)benzene (TPBi), Bis(2-methyl-8-quinolinato-N1,O8)-(1,1'-biphenyl-4-olato)aluminum (BAlq), 4,7-diphenyl-1,10-phenanthroline (Bphen), 2,9-Bis(naphthalene-2-yl)4,7-diphenyl-1,10-phenanthroline (NBphen), 2,9-Dimethyl-4,7-diphenyl-1,10-phenaathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl)1,3,5-triazine (TmPPPyTz), Poly[9,9-bis(3'-(N,N-dimethyl)-N-ethylammonium)-propyl)-2,7-fluorene]-alt-2,7-(9,9-dioctylfluorene)] (PFNBr), tris(phenylquinoxaline) (TPQ) and/or diphenyl-4-triphenylsilyl-phenylphosphine oxide (TSPO1).

In another exemplar aspect, The ETL 270 can comprise any organic compound having the structure of Chemical Formulae 1 to 9. The organic compound has high affinity to electrons. In this case, the ETL 270 can comprise only the organic compound or can comprise the organic compound mixed or doped with the above electron transporting material.

The EIL 280 is disposed between the second electrode 230 and the ETL 270, and can improve physical properties of the second electrode 230 and therefore, can enhance the lifetime of the OLED D1. In one exemplary aspect, the EIL 280 can comprise, but is not limited to, an alkali metal halide and/or an alkaline earth metal halide such as LiF, CsF, NaF, BaF$_2$ and the like, and/or an organic metal compound such as lithium quinolate, lithium benzoate, sodium stearate, and the like.

When holes are transferred to the second electrode 230 via the EML 240 and/or electrons are transferred to the first electrode 210 via the EML 240, the OLED D1 can have short lifetime and reduced luminous efficiency. In order to prevent these phenomena, the OLED D1 in accordance with this aspect of the present disclosure can have at least one exciton blocking layer adjacent to the EML 240.

For example, the OLED D1 of the exemplary aspect includes the EBL 265 between the HTL 260 and the EML 240 so as to control and prevent electron transfers. In one exemplary aspect, the EBL 265 can comprise, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, 1,3-Bis(carbazolyl-9-yl)benzene (mCP), 3,3'-bis(N-carbazolyl)-1,1-biphenyl (mCBP), CuPc, N,N'-bis[4-(bis(3-methylphenyl)amino)phenyl]-N,N'-diphenyl-[1,1'-biphenyl]-4,4'-diamine (DNTPD), TDAPB, DCDPA and/or 2,8-bis(9-phenyl-9H-carbazol-3-yl)dibenzo[b,d]thiophene.

In addition, the OLED D1 can further include the HBL 275 as a second exciton blocking layer between the EML 240 and the ETL 270 so that holes cannot be transferred from the EML 240 to the ETL 270. In one exemplary aspect, the HBL 275 can comprise, but is not limited to, any one of oxadiazole-based compounds, triazole-based compounds, phenanthroline-based compounds, benzoxazole-based compounds, benzothiazole-based compounds, benzimidazole-based compounds, and triazine-based compounds each of which can be used in the ETL 270.

For example, the HBL 275 can comprise a compound having a relatively low HOMO energy level compared to the luminescent materials in EML 240. The HBL 275 can comprise, but is not limited to, BCP, BAlq, Alq$_3$, PBD, spiro-PBD, Liq, Bis-4,5-(3,5-di-3-pyridylphenyl)-2-methylpyrimidine (B3PYMPM), Bis[2-(diphenylphosphino)phenyl] ether oxide (DPEPO), 9-(6-(9H-carbazol-9-yl)pyridine-3-yl)-9H-3,9'-bicarbazole and combination thereof.

In another exemplary aspect, the HBL 275 can comprise any organic compound having the structure of Chemical Formulae 1 to 9. The organic compound has relatively low HOMO energy level to have hole blocking property. In this case, the HBL 275 can comprise only the organic compound or can comprise the organic compound mixed or doped with the above hole blocking material.

As described above, the EML 240 includes the first compound H of the organic compound having the structure of Chemical Formulae 1 to 3, and the second compound TD which can be the delayed fluorescent material. In the prior art, the EML 240 has used a p-type host that has excellent affinity to holes. When the p-type host is applied into the EML 240, the recombination zone among holes and electrons is formed at an interface between the EML 240 and the HBL 275 because the p-type host prefers holes to electrons. In this case, some of charges injected into the EML 240 cannot recombine with opposite charges to be quenched, and the luminous efficiency is deteriorated.

On the contrary, the organic compound having the structure of Chemical Formulae 1 to 9 is the bipolar compound that comprises the pyridine moiety having the n-type property and the fused aromatic or hetero aromatic moiety having the p-type property. When the organic compound is applied into the host in the EML 240, the recombination zone among the holes and electrons are distributed uniformly in the whole area of the EML 240 including an interface between the EML 240 and the EBL 265. In addition, when the organic compound having the structure of Chemical Formulae 1 to 9 is introduced into the EML 240, exciton confinement efficiency is increased. Therefore, charges injected into the EML 240 are rarely quenched without recombining with opposite charges, thus the OLED D1 can maximize its luminous efficiency.

As the holes injected from the anode and the electrons injected from the cathode are recombined to form excitons as an excited state, and the OLED emits light as the unstable excitons shifted to the stable ground state. External quantum efficiency (EQE) of the luminous material in an EML can be determined by four factors, a singlet and triplet ratio, a charge balance factor, a radiative efficiency and an out-coupling efficiency.

When holes and electrons meet to form exciton, singlet exciton with a paired spin state and triplet exciton with an unpaired spin state is generated in a ratio of 1:3 in theory. Only the singlet exciton participates in luminescence and the remaining 75% triplet excitons cannot participate in luminescence in the fluorescent material. When taking all four factors defined into account, the maximum luminous efficiency of the OLED using the conventional fluorescent material is only about 5%.

On the other hand, phosphorescent materials have a luminescent mechanism that converts both the singlet and triplet excitons to light. Phosphorescent materials convert singlet exciton into triplet exciton through intersystem crossing (ISC). Therefore, when using phosphorescent materials using both singlet exciton and triplet exciton, it is possible to improve the low luminous efficiency of the fluorescent materials. But, particularly, the blue phosphorescent material shows too bad color purity and too short luminous lifetime to be applicable to a commercial device.

Figure 3:
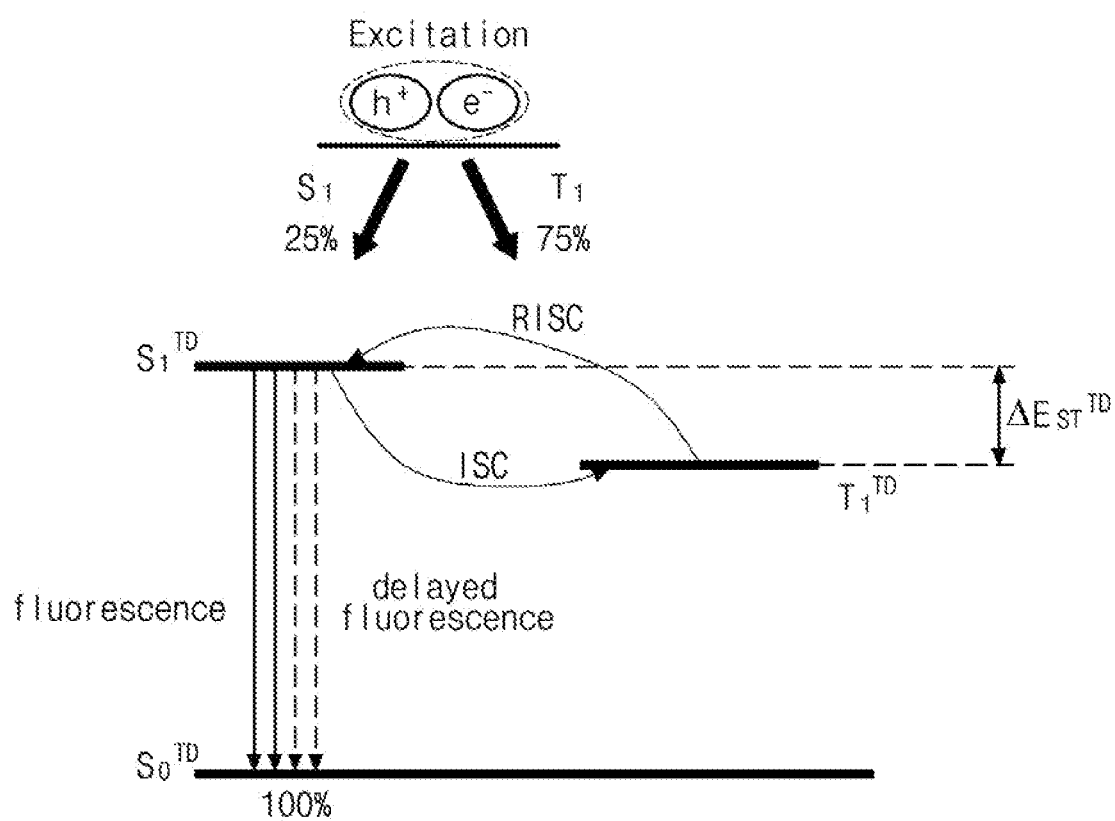
FIG. 3 is a schematic diagram illustrating a luminous mechanism of delayed fluorescent material that can be included in an EML in accordance with the present disclosure.

Delayed fluorescent material, which can solve the problems accompanied by the conventional art fluorescent and/or phosphorescent materials, has been developed. Representative delayed fluorescent material is a thermally-activated delayed fluorescent (TADF) material. The luminous mechanism of the delayed fluorescent material will be explained with referring to FIG. 3, which is a schematic diagram illustrating a luminous mechanism of the delayed fluorescent material that can be included in the EML 240. As illustrated in FIG. 3, the excitons of singlet energy level $S_1^{TD}$ as well as the excitons of triplet energy level $T_1^{TD}$ in the delayed fluorescent material TD can be transferred to an intermediate energy level state, i.e. ICT (intramolecular charge transfer) state, and then the intermediate stated excitons can be shifted to a ground state ($S_0^{TD}$; $S_1^{TD} \rightarrow ICT \leftarrow T_1^{TD}$).

Since the compound that can be ICT state has little orbital overlaps between HOMO and LUMO states, there is little interaction between the HOMO state and the LUMO state. As a result, the changes of spin states of electrons do not have an influence on other electrons, and a new charge transfer band (CT band) that does not follow the selection rule is formed within the delayed fluorescent material. In case of driving an OLED that includes the delayed fluorescent material TD, both 25% singlet excitons and 75% triplet excitons are converted to ICT state by heat or electrical field, and then the converted excitons drops to the ground state $S_0^{TD}$ with luminescence. Therefore, the delayed fluorescent material TD can have 100% internal quantum efficiency in theory.

Figure 4:
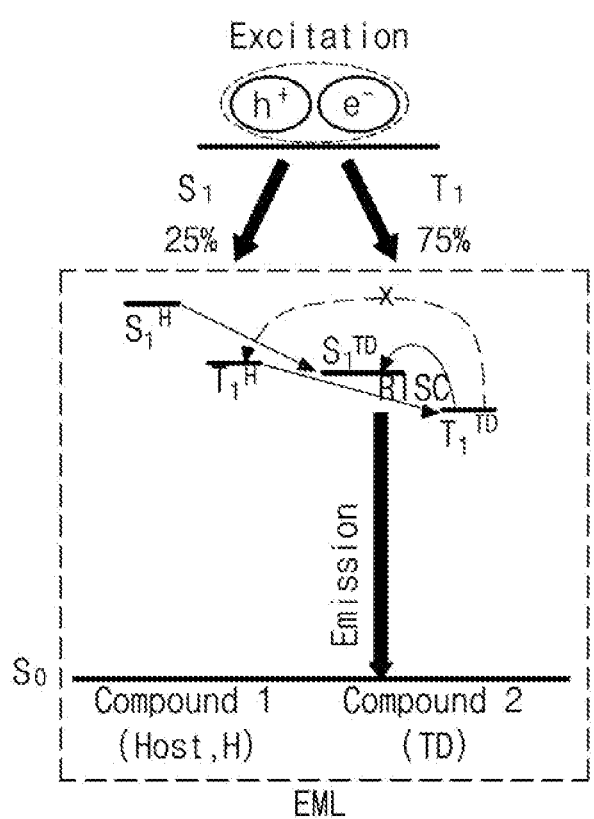
FIG. 4 is a schematic diagram illustrating luminous mechanism by energy level bandgap among luminous materials in accordance with an exemplary aspect of the present disclosure.

The delayed fluorescent material TD must has an energy level bandgap $\Delta E_{ST}^{TD}$ equal to or less than about 0.3 eV, for example, from about 0.05 to about 0.3 eV, between the excited singlet energy level $S_1^{TD}$ and the excited triplet energy level $T_1^{TD}$. The material having little energy bandgap $\Delta E_{ST}^{TD}$ between the singlet energy level $S_1^{TD}$ and the triplet energy level $T_1^{TD}$ can exhibit common fluorescence with Inter system Crossing (ISC) in which the excitons of singlet energy level $S_1^{TD}$ can be shifted to the ground state, as well as delayed fluorescence with Reverser Inter System Crossing (RISC) in which the excitons of triplet energy level $T_1^{TD}$ can be transferred upwardly to the excitons of singlet energy level $S_1^{TD}$, and then the exciton of singlet energy level $S_1^{TD}$ transferred from the triplet energy level $T_1^{TD}$ can be shifted to the ground state $S_0^{TD}$. The host for implementing delayed fluorescence must induce the triplet exciton at the delayed fluorescent material to be involved in the luminescence process without quenching as a non-radiative recombination. To this end, the energy levels among the host and the delayed fluorescent material as the dopant should be adjusted. FIG. 4 is a schematic diagram illustrating luminous mechanism by energy level bandgap among luminous materials in accordance with an exemplary aspect of the present disclosure.

As described above, the organic compound having the structure of Chemical Formulae 1 to 9 has excellent thermal property as well as very high excited triplet energy level $T_1^H$. As illustrated in FIG. 4, each of an excited singlet energy level $S_1^H$ and an excited triplet energy level $T_1^H$ of the first compound H of the host in the EML 240 should be higher than each of the excited singlet energy level $S_1^{TD}$ and the excited triplet energy level $T_1^{TD}$ of the second compound TD of the delayed fluorescent material, respectively. As an example, the excited triplet energy level $T_1^H$ of the first compound can be higher than the excited triplet energy level $T_1^{TD}$ of the third compound TD by at least about 0.5 eV, e.g. at least about 0.2 eV. In this case, the energy confinement efficiency between the first compound H and the second compound TD can be improved, and the reverse charge transfer, i.e., exciton energy transfer from the excited triplet energy level $T_1^{TD}$ of the second compound TD to the excited triplet energy level $T_1^H$ of the first compound H, can be suppressed.

When at least one of the excited singlet energy level $S_1^H$ and the excited triplet energy level $T_1^H$ of the first compound H is not high enough than each of the singlet energy level $S_1^{TD}$ and the excited triplet energy level $T_1^{TD}$ of the second compound TD, the exciton at the excited triplet energy level $T_1^{TD}$ of the second compound TD can be reversely transferred to the excited triplet energy level $T_1^H$ of the first compound H. In this case, the triplet exciton reversely transferred to the first compound H where the triplet exciton cannot be emitted is quenched as non-emission so that the triplet exciton energy of the second compound TD having the delayed fluorescent property cannot contribute to luminescence. The energy level bandgap $\Delta E_{ST}^{TD}$ between the excited singlet energy level $S_1^{TD}$ and the excited triplet energy level $T_1^{TD}$ of the second compound TD can be equal to or less than about 0.3 eV, for example, between about 0.05 eV and about 0.3 eV so as to implement delayed fluorescence (see, FIG. 3)

In addition, it is necessary to adjust the LUMO and HOMO energy levels of the first and second compounds H and TD so that holes and electrons are injected rapidly into the EML 240 to recombine excitons efficiently. For example, it is preferable that an energy level bandgap ($|HOMO^H - HOMO^{TD}|$) between the HOMO energy level ($HOMO^H$) of the first compound H and the HOMO energy level ($HOMO^{TD}$) of the second compound TD, or an energy level bandgap ($|LUMO^H - LUMO^{TD}|$) between the LUMO energy level ($LUMO^H$) of the first compound H and the LUMO energy level ($LUMO^{TD}$) of the second compound TD can be equal to or less than about 0.5 eV, for example, between about 0.1 eV to about 0.5 eV.

When the EML 240 comprise both the first compound H of the organic compound having the structure of Chemical Formulae 1 to 9 and the second compound TD, the exciton energy can be transferred to the second compound TD without energy loss in the luminescence process. In this case, the exciton quenching owing to the interaction between the host exciton and the peripheral polarons can be minimized. In addition, since the organic compound having the structure of Chemical Formulae 1 to 9 has excellent thermal property, its degradations or damages such as crystallizations caused by Joule's heat generated in the course of driving the OLED D1 can be suppressed, and therefore, the OLED D1 can implement long luminescent lifetime.

In one exemplary aspect, the second compound can be delayed fluorescent material emitting red (R), green (G) or blue (B) light. As an example, the second compound TD can have, but is not limited to, the excited single energy level $S_1^{TD}$ between about 2.7 eV and about 2.75 eV, and the excited triplet energy level $T_1^{TD}$ between about 2.4 eV and about 2.5 eV. Also, the second compound TD can have the HOMO energy level between about −5.0 eV and about −6.0 eV, preferably between about −5.0 eV and about −5.5 eV, and the LUMO energy level between about −2.5 eV and about −3.5 eV, preferably between about −2.5 eV and about −3.0 eV. In this case, the energy level bandgap $E_g$ between the HOMO energy level and the LUMO energy level of the second compound TD can be between about 2.2 eV and about 3.0 eV, preferably between about 2.4 eV and 2.8 eV.

In one exemplary aspect, the second compound TD of the blue emitting delayed fluorescent material in the EML 240 can comprise, but is not limited to, 10-(4-(diphenylphosphoryl)phenyl)-10H-phenoxazine 4,4'-(phenylphosphoryl) bis(4,1-phenylene))bis(10H-phenoxazine (DPXZPO), 10,10',10'''-(4,4',4''-phosphoryltris(benzene-4,1-diyl))tris (10H-phenoxazine (TPXZPO), 9,9'-(5-(4,6-diphenyl-1,3,5-triazin-2-yl)-1,3-phenylene)bis(9H-carbazole) (DcZTrz), 9,9',9'',9'''-((6-phenyl-1,3,5-triazin-2,4-diyl)bis(benzene-5,3,1-triyl))tetrakis(9H-carbazole) (DDczTrz), 2,7-bis(9,9-dimethylacridin-10(9H)-yl)-9,9-dimethyl-9H-thioxanthene-10, 10-dioxide (DMTDAc), 9,9'-(4,4'-sulfonylbis(4,1-phenylene))bis(3,6-dimethoxyl-9H-carbazole) (DMOC-DPS), 10,10'''-(4,4'-Sulfonylbis(4,1-phenylene))bis(9,9-dimethyl-9,10-dihydroacridine (LMAC-DPS), 10-(4-(4,6-diphenyl-1,3,5-triazin-2-yl)phenyl)-9,9-dimethyl-9,10-dihydroacridine (DMAC-TRZ), 10-phenyl-10H,10'H-spiro [acridine-9,9'-anthracen]-10'-one (ACRSA), 3,6-dibenzoyl-4,5-di(1-methyl-9-phenyl-9H-carbazoyl)-2-ethynylbenzonitrile (Cz-VPN), 9,9',9''-(5-(4,6-diphenyl-1,3,5-triazin-2-yl)benzene-1,2,3-triyl) tris(9H-carbazole) (TcZTrz), 2'-(10H-phenoxazin-10-yl)-[1,1':3',1''-terphenyl]-5'-carbonitrile (mPTC), bis(4-(9H-3,9'-bicarbazol-9-yl)phenyl)methanone (CC2BP), 9-'[4-(4,6-diphenyl-1,3,5-triazin-2-yl)phenyl]-3,3'',6,6''-tetraphenyl-9,3':6',9''-ter-9H-carbazole (BDPCC-TPTA), 9'-[4-(4,6-diphenyl-1,3,5-triazin-2-yl)phenyl]-9,3':,6',9''-ter-9H-carbazole (BCC-TPTA), 9-(4-(4,6-diphenyl-1,3,5-triazin-2-yl)phenyl)-3',6'-diphenyl-9H-3,9'-bicarbazole (DPCC-TPTA), 1044,6-diphenyl-1,3,5-triazin-2-yl)-10H-phenoxazine (Phen-TRZ), 9-(4-(4,6-diphenyl-1,3,5-triazin-2-yl)phenyl)-9H-carbazole (Cab-Ph-TRZ), 10-(4-(4,6-diphenyl-1,3,5-triazin-2-yl)phenyl)-10H-spiro[acridine-9,9'-fluorene] (SpiroAC-TRZ), 4,6-di(9H-carbazol-9-yl)isophthalonitrile (DczIPN), 3CzFCN and 2,3,4,6-tetra(9H-carbazol-9-yl)-5-fluorobenzonitrile (4CzFCN).

In another exemplary aspect, the second compound TD of the green emitting delayed fluorescent material in the EML 240 can comprise, but is not limited to, 5'-(phenoxazin-10-yl)-[1,1':3',1''-terphenyl]-2'-carbonitrile (oPTC), 2-biphenyl-4,6-bis(12-phenylindolo[2,3-a]carbazol-11-yl)-1,3,5-triazine (PIC-TRZ), 9,9',9''-(5-(4,6-diphenyl-1,3,5-triazin-2-yl)benzene-1,2,3-triyl)tris(3,6-dimentyl-9H-carbazole (TmCzTrz), 2,5-bis(4-(10H-phenoxazin-10-yl)phenyl)-1,3, 4-oxadiazole (2PXZ-OXD), bis(4-(9,9-dimethylacridin-10 (9H)-yl)phenyl)methanone (DMAC-BP), 2-(9-phenyl-9H-carbazol-3-yl)-10,10-dioxide-9H-thioxanthen-9-one (TXO-PhCz), 2,4,5,6-tetra(9H-carbazol-9-yl)isophthalonitrile (4CzIPN), 3,4,5,6-tetra(9H-carbazol-9-yl)isophtlialonitrile (4CzPN), 9H-carbazol-9-yl)-5-fluorobenzonitrile (4CzFCN), 6,6-(9H,9'H-[3,3'-bicarbazole]-9,9'-diyl)bis(4-(9H-carbazol-9-yl)isophthalonitrile (33 TczPN), 4,5-bis(5H-benzofuro[3,2-c]carbazol-5-yl)phthalonitrile (BFCz-2CN), 4,5-bis(5H-benzo[4,5]thieno[3,2-c]carbazol-5-yl)phthalonitrile (BTCz-2CN), 4,4''-bis(9,9-dimethylacridin-10(9H)-yl)-[1,1':2',1''-terphenyl]-4,5-dicarbonitrile (Ac-VPN), 4,4''-di (10H-phenoxazin-10-yl)-[1,1':2',1''-terphenyl]-4',5'-dicarbonitrile (Px-VPN), 5,5'-(9H,9'H-[3,3'-bicarbazole]-9, 9'-diyl)diisophthalnonitrile (35IPNDcz), 2,2'-(9H,9'H-[3,3'-bicarbazole]-9,9'-diyl)diisophthalnonitrile (26IPNDcz), 9,9', 9''-(5-(4,6-diphenyl-1,3,5-triazin-2-yl)benzene-1,2,3-triyl) tris(9H-carbazole) (TcZTrz) and 32alCTRZ.

In still another exemplary aspect, the second compound TD of the red emitting delayed fluorescent material in the EML 240 can comprise, but is not limited to, 1,3-bis[4-(10H-phenoxazin-10-yl)benzoyl]benzene (mPx2BBP), 2,3, 5,6-tetrakis(3,6-diphenylcarbazol-9-yl)-1,4-dicyanobenzene (4CzTPN-Ph), 10,10'-(sulfonylbis(4,1-phenylene))bis(5-phenyl-5,10-dihydrophenazine) (PPZ-DPS), 5,10-bis(4-(benzo[d]thiazol-2-yl)phenyl)-5,10-dihydrophenazine (DHPZ-2BTZ), 5,10-bis(4-(4,6-diphenyl-1,3,5-triazin-2-yl) phenyl)-5,10-dihydrophenazine (DHPZ-2TRZ) and 7,10-bis (4-(diphenylamino)phenyl)-2,3-dicyanopyrazino phenanathrene (TPA-DCPP).

For example, the delayed fluorescent material that can be used as the second compound TD in the EML 240 can be any compound having the following structure of Chemical Formula 10:

[Chemical Formula 10]

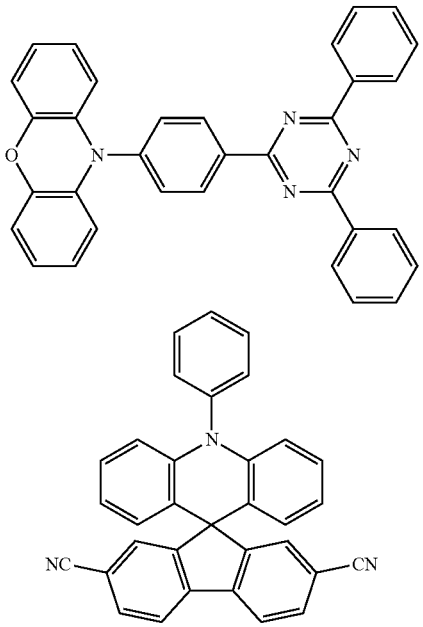

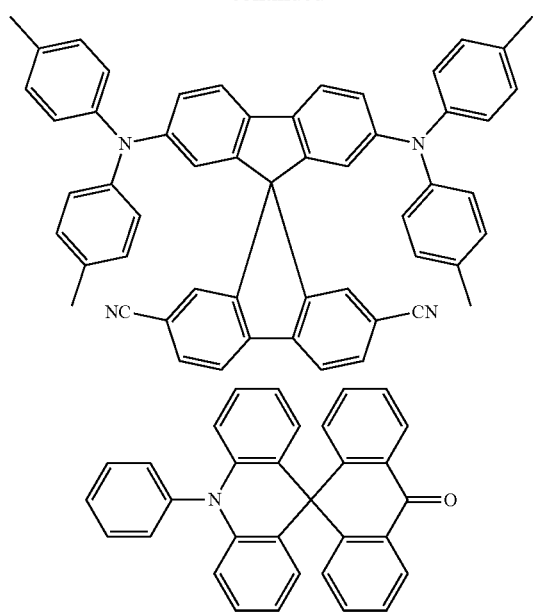
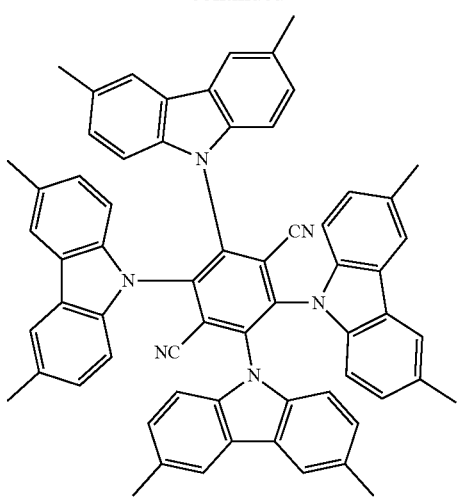
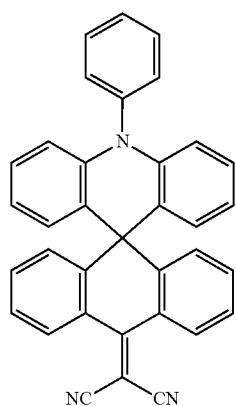
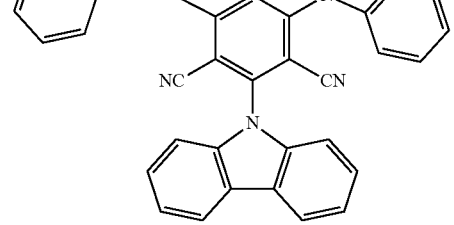
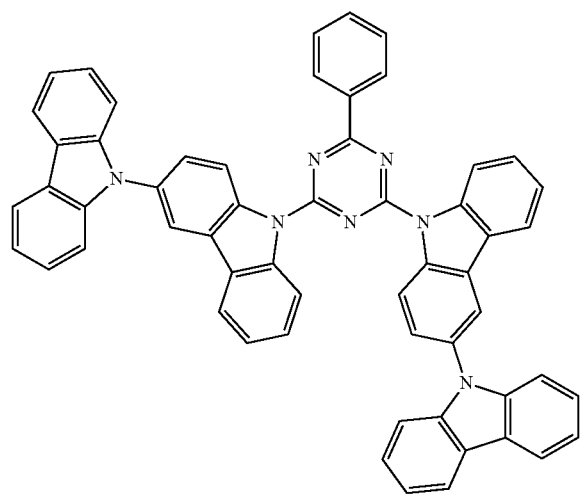
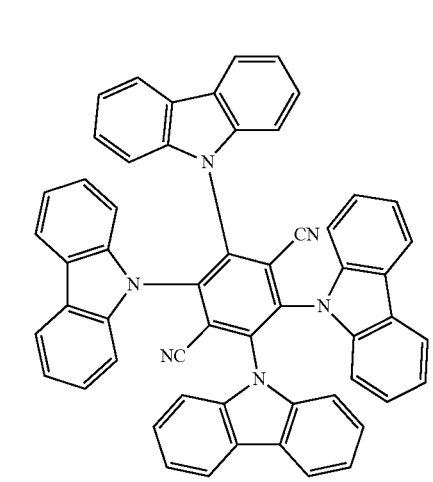

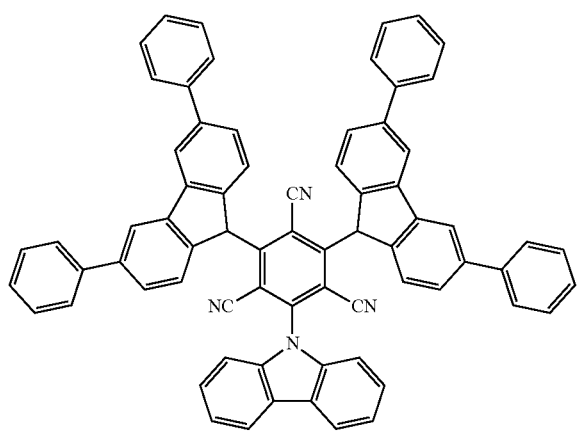
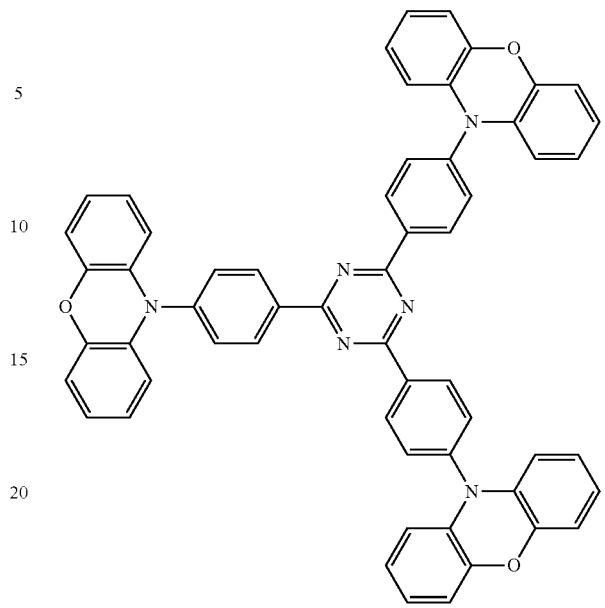
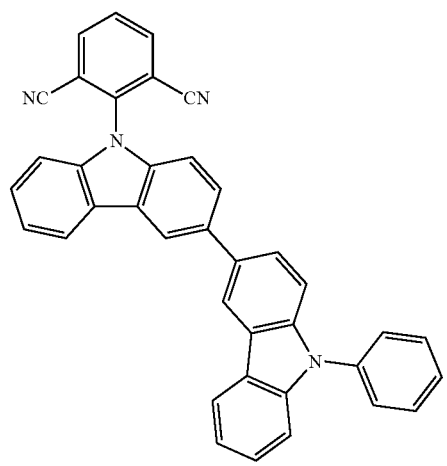
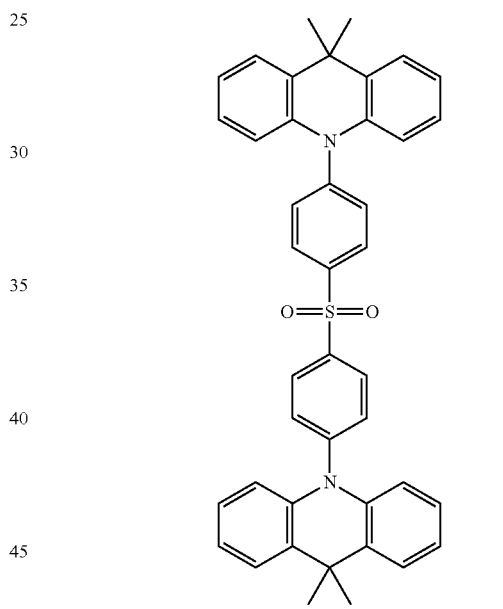
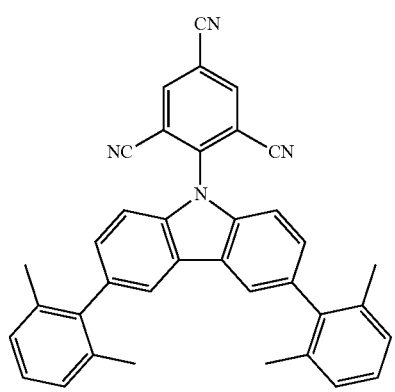
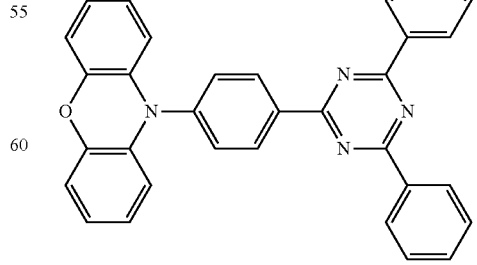

47
-continued
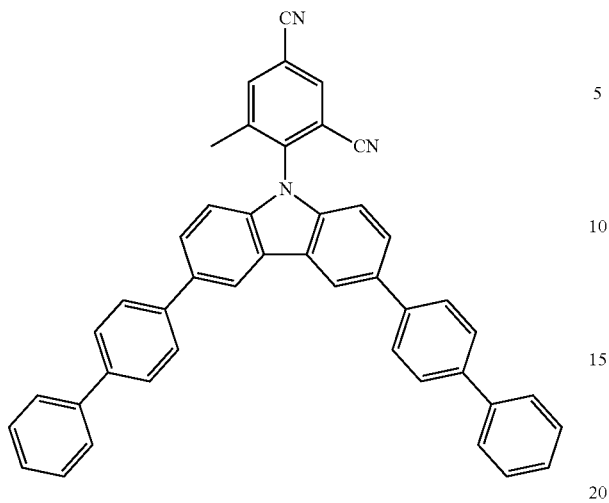
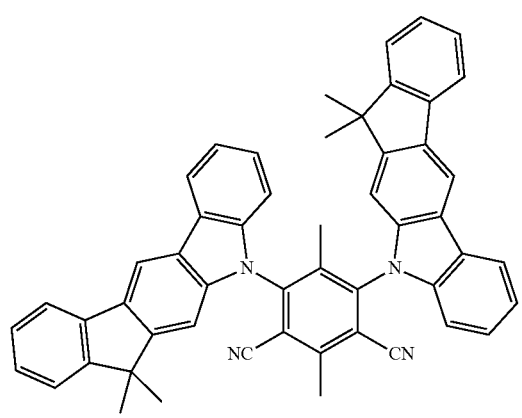
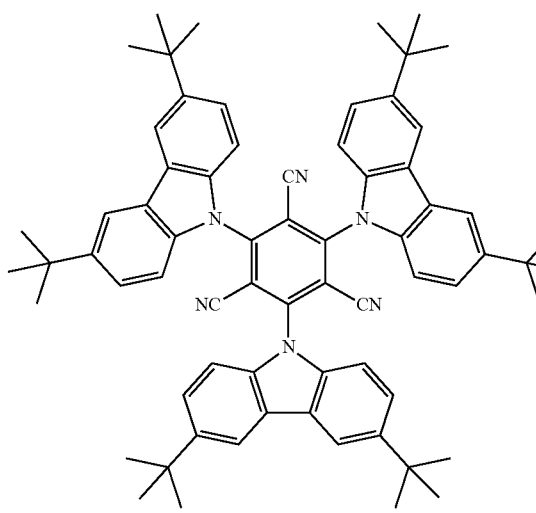
48
-continued
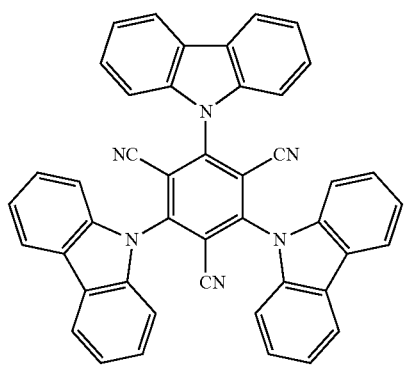
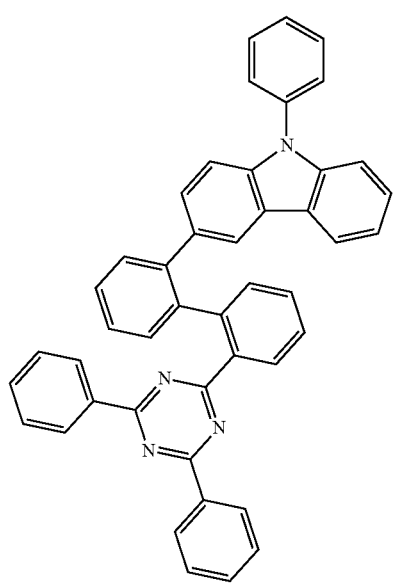
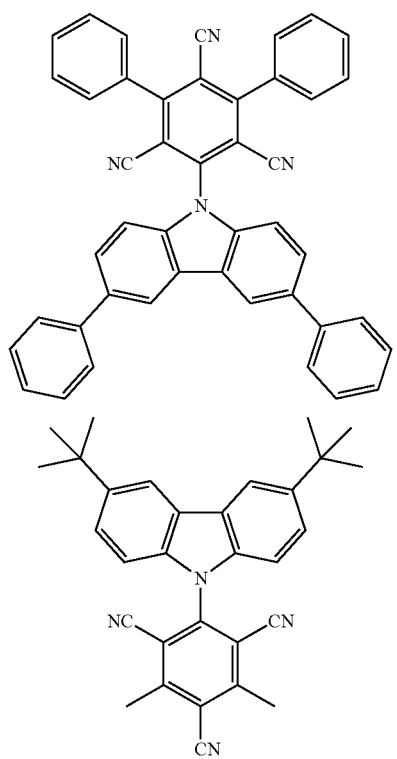

-continued
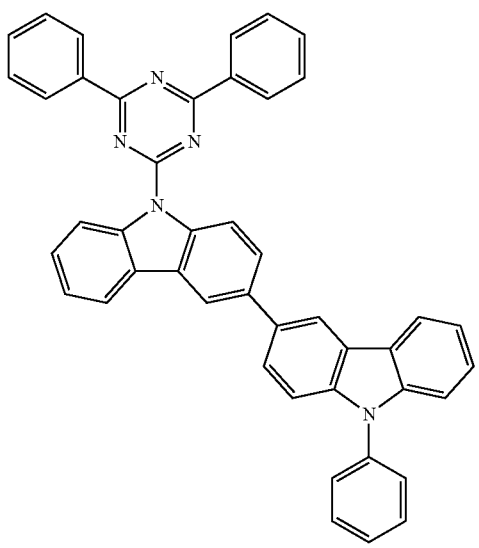
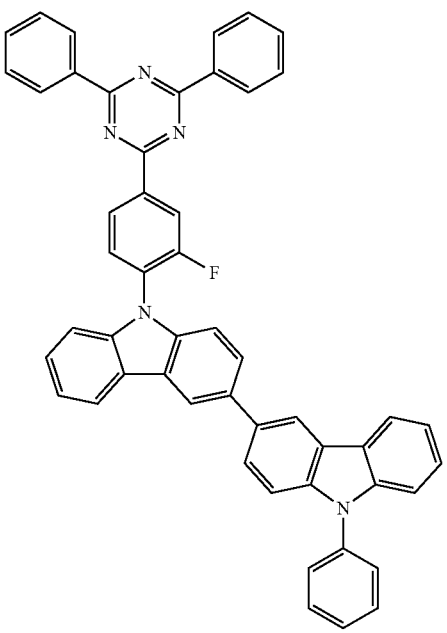
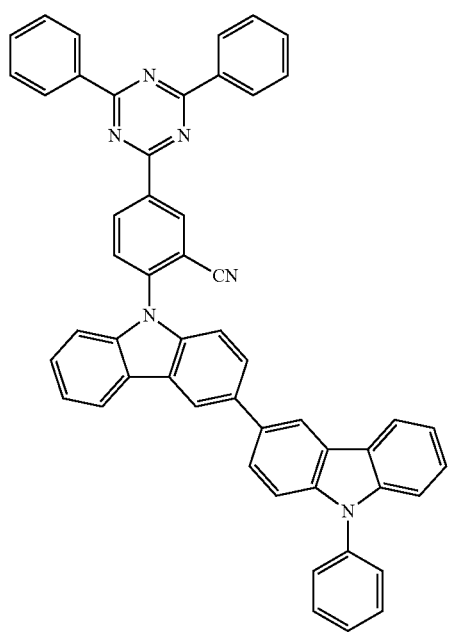
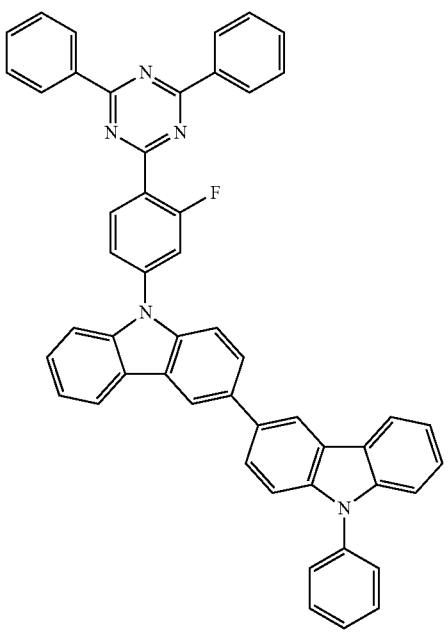

51
-continued
52
-continued
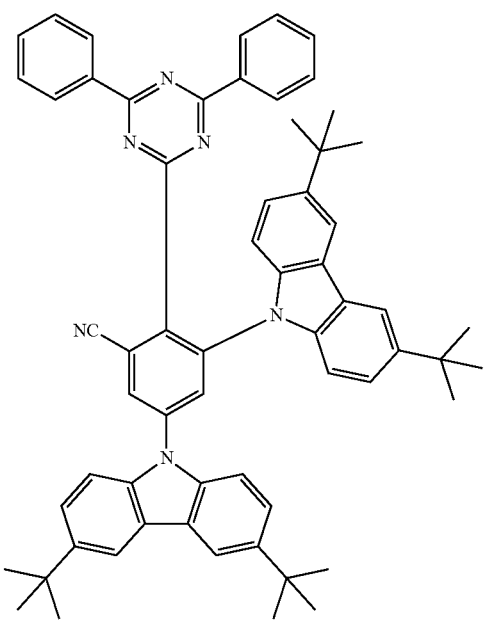
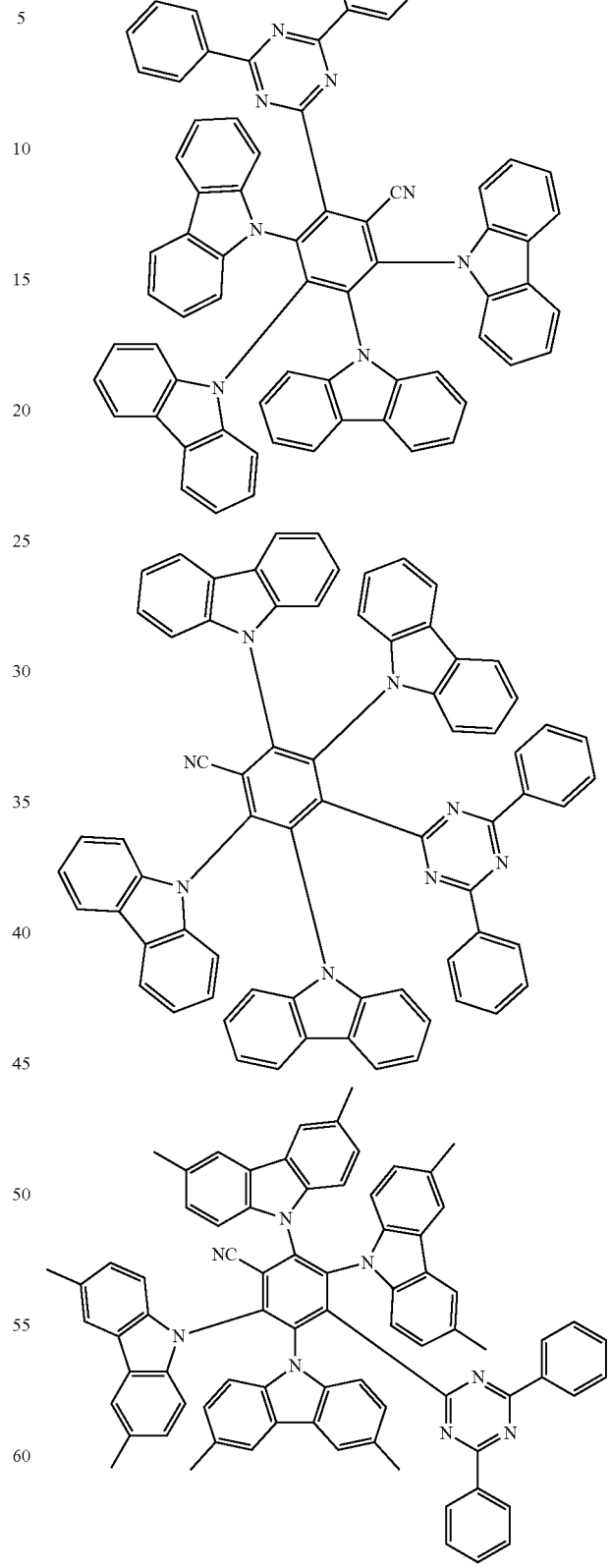
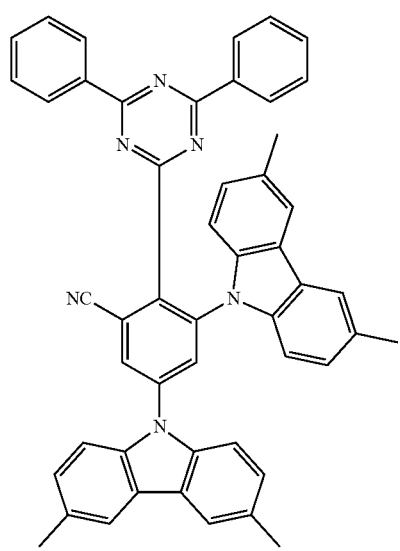

53
-continued
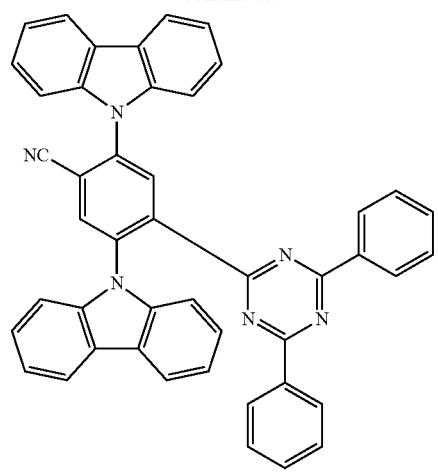
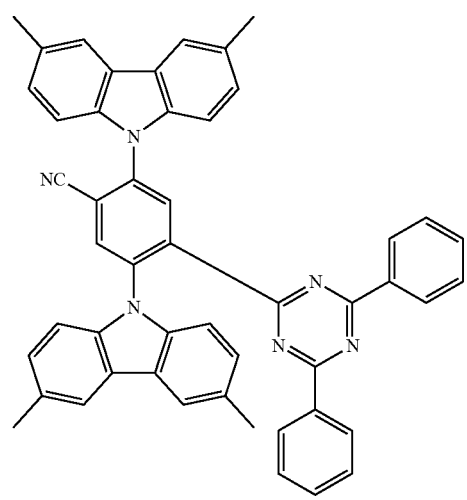
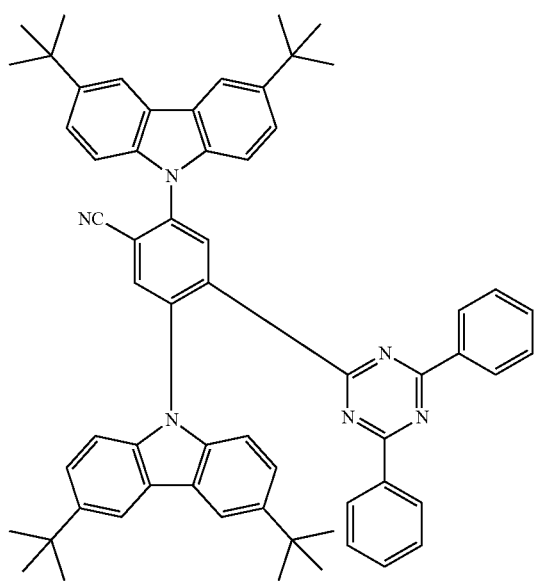
54
-continued
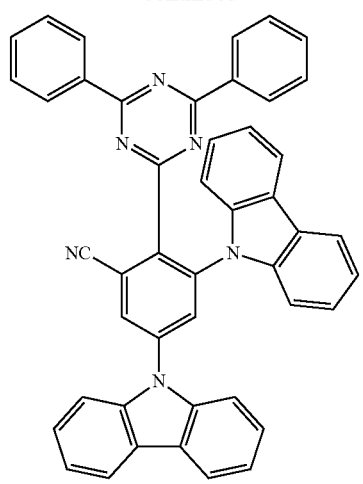
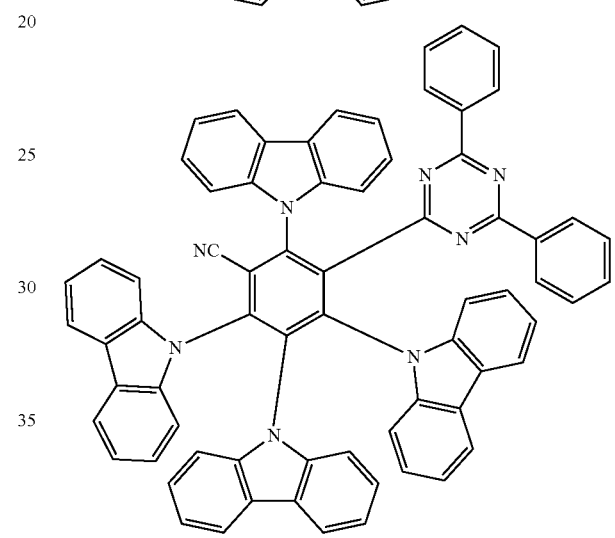
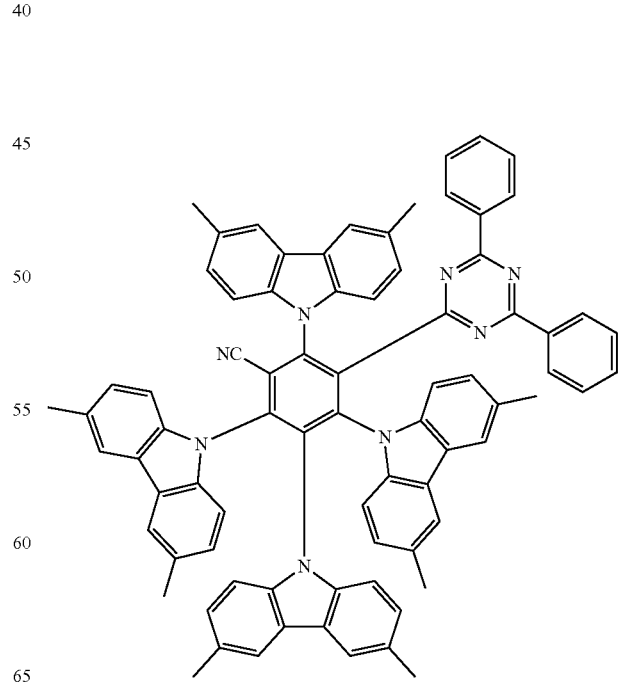

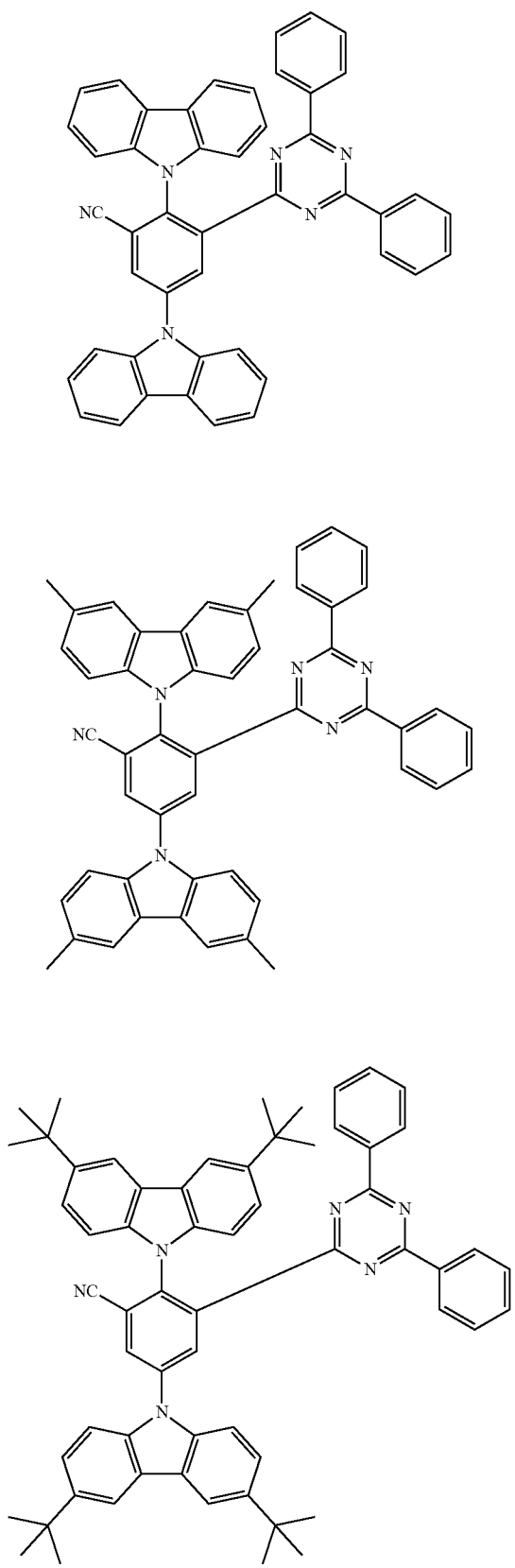
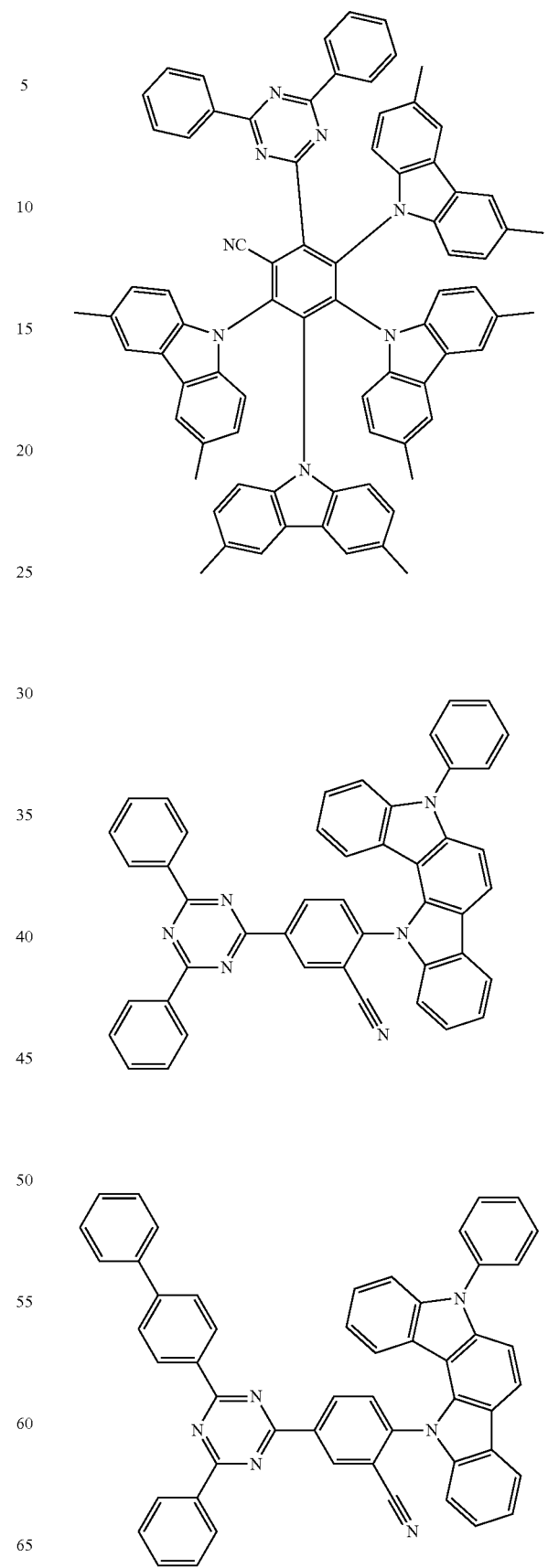

57
-continued
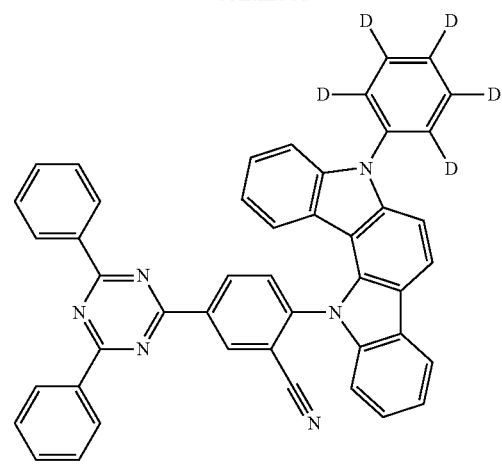
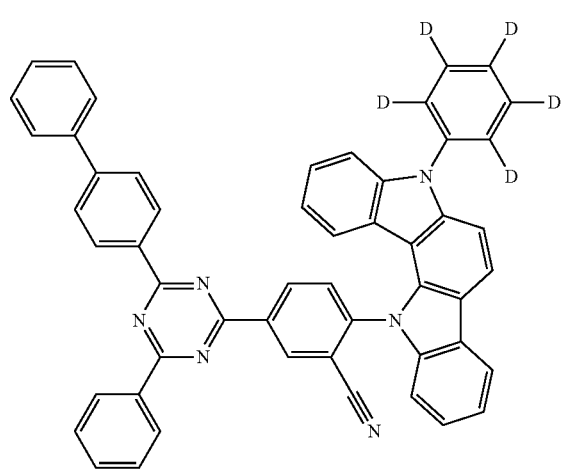
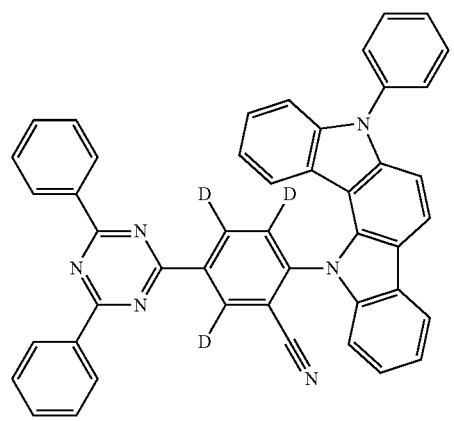
58
-continued
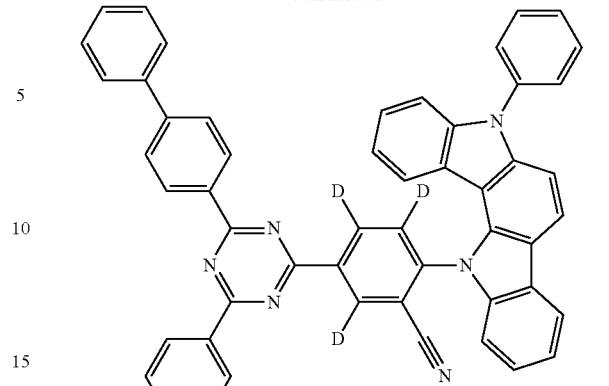
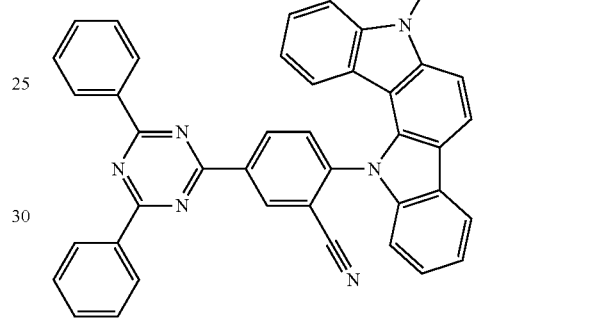
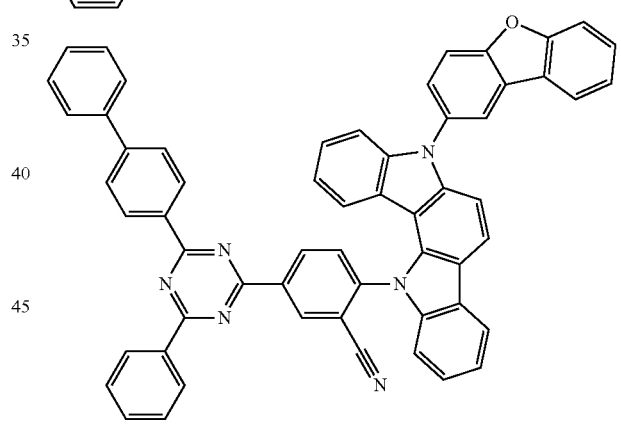
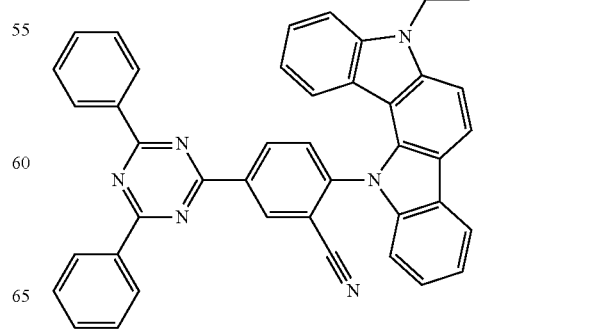

-continued

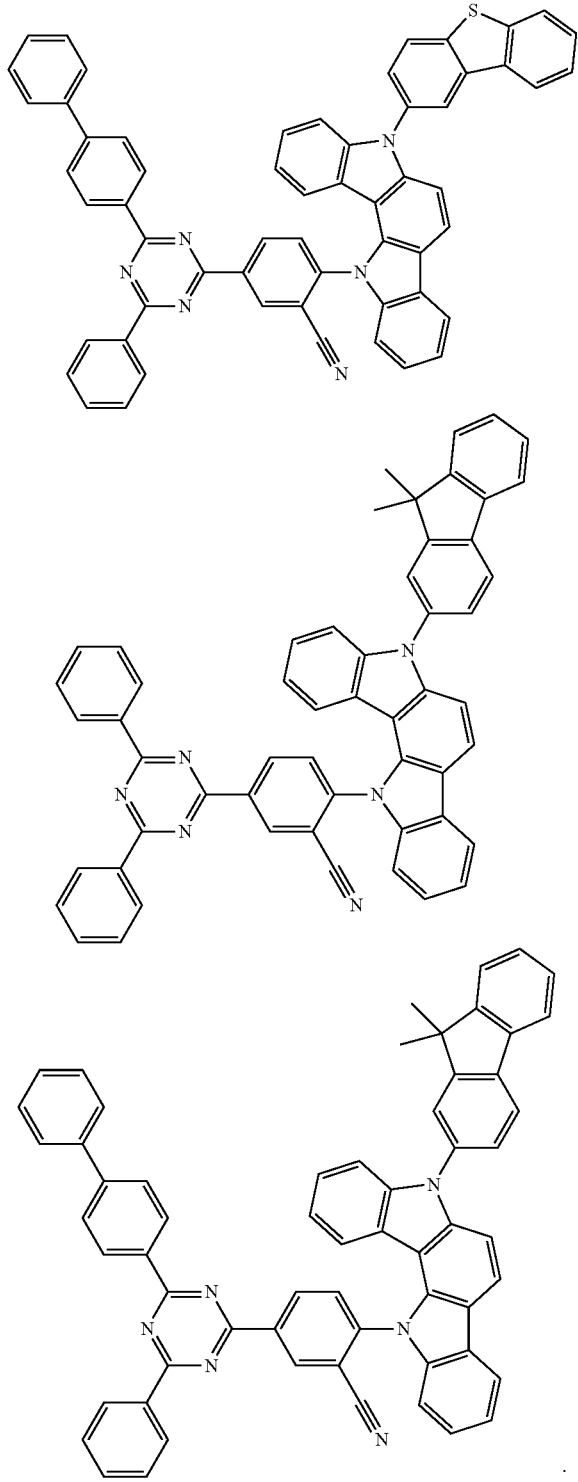

When the EML 240 includes the first compound H of the host and the second compound TD of the delayed fluorescent material, the contents of the second compound TD in the EML 240 can be, but is not limited to, between about 10 wt % and about 70 wt %, preferably between about 10 wt % and about 50 wt %, and more preferably between about 20 wt % and about 40 wt %.

Figure 5:
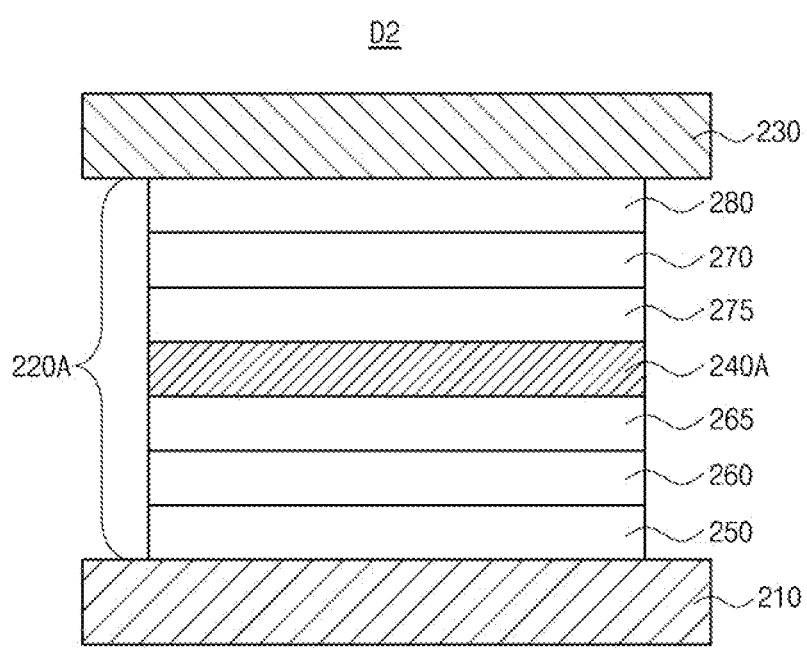
FIG. 5 is a schematic cross-sectional view illustrating an OLED in accordance with another exemplary aspect of the present disclosure.

FIG. 5 is a schematic cross-sectional view illustrating an OLED in accordance with another exemplary aspect of the present disclosure. As illustrated in FIG. 5, the OLED D2 comprises the first electrode 210, the second electrode 230 facing the first electrode 210 and an emissive layer 220A disposed between the first and second electrodes 210 and 230. The organic light emitting display device 100 (FIG. 1) may include a red pixel region, a green pixel region and a blue pixel region, and the OLED D2 may be located in any one of the red green pixel region, the green pixel region and the blue pixel region.

The emissive layer 220A having single emitting part comprises an EML 240A. Also, the emissive layer 220A may comprise at least one of a HTL 260 disposed between the first electrode 210 and the EML 240A and an ETL 270 disposed between the second electrode 230 and the EML 240A. Also, the emissive layer 220 may further comprise at least one of a HIL 250 disposed between the first electrode 210 and the HTL 260 and an EIL 280 disposed between the second electrode 230 and the ETL 270. Alternatively, the emissive layer 220A can further comprise the EBL 265 disposed between the HTL 260 and the EML 240A and/or the HBL 275 disposed between the EML 240A and the ETL 270. The configurations of the first and second electrodes 210 and 230 as well as other layers except the EML 240A in the emissive layer 220A can be substantially identical to the corresponding electrodes and layers in the OLED D1.

In this aspect, the EML 240A comprise the first compound H, the second compound TD and a third compound FD. The first compound H can be the host, the second compound TD can be the delayed fluorescent material (first dopant) and the third compound FD can be fluorescent or phosphorescent material (second dopant). The first compound H can be the organic compound having the structure of Chemical Formulae 1 to 9. When the EML 240A further comprises the fluorescent or phosphorescent material FD as well as the delayed fluorescent material TD, it is possible to realize OLED D2 having much enhanced luminous efficiency by adjusting energy levels among the host and the dopants.

The EML 240 (see, FIG. 3) includes only the first compound H of the host and the second compound TD having the delayed fluorescent property, the second compound TD exhibit maximally 100% internal quantum efficiency in theory, which is equivalent to the conventional phosphorescent material such as metal complexes. However, because of the bond formation between the electron acceptor and the electron donor and conformational twists within the delayed fluorescent material, additional charge transfer transition (CT transition) within the delayed fluorescent material is caused thereby, and the delayed fluorescent material has various geometries. As a result, the delayed fluorescent materials show luminescence spectra having very broad FWHM (full-width at half maximum) in the luminescence process, which results in poor color purity. In addition, the delayed fluorescent material utilizes the triplet exciton energy as well as the singlet exciton energy in the luminescence process with rotating each moiety within its molecular structure, which results in twisted internal charge transfer (TICT). As a result, the luminous lifetime of an OLED including only the delayed fluorescent materials can be reduced owing to weakening of molecular bonding forces among the delayed fluorescent materials.

The EML 240A of this aspect further comprises the third compound FD of fluorescent or phosphorescent material so as to prevent the color purity and the luminous lifetime of the OLED D1 from being deteriorated when the EML includes only the delayed fluorescent material as a dopant. With referring to FIG. 6, the triplet exciton energy of the second compound TD having the delayed fluorescent property is converted upwardly to its own singlet exciton energy, and then the converted singlet exciton energy of the second compound TD can be transferred to the third compound FD in the same EML 240A via FRET (Forster Resonance Energy Transfer) mechanism to implement hyper fluorescence.

Figure 6:
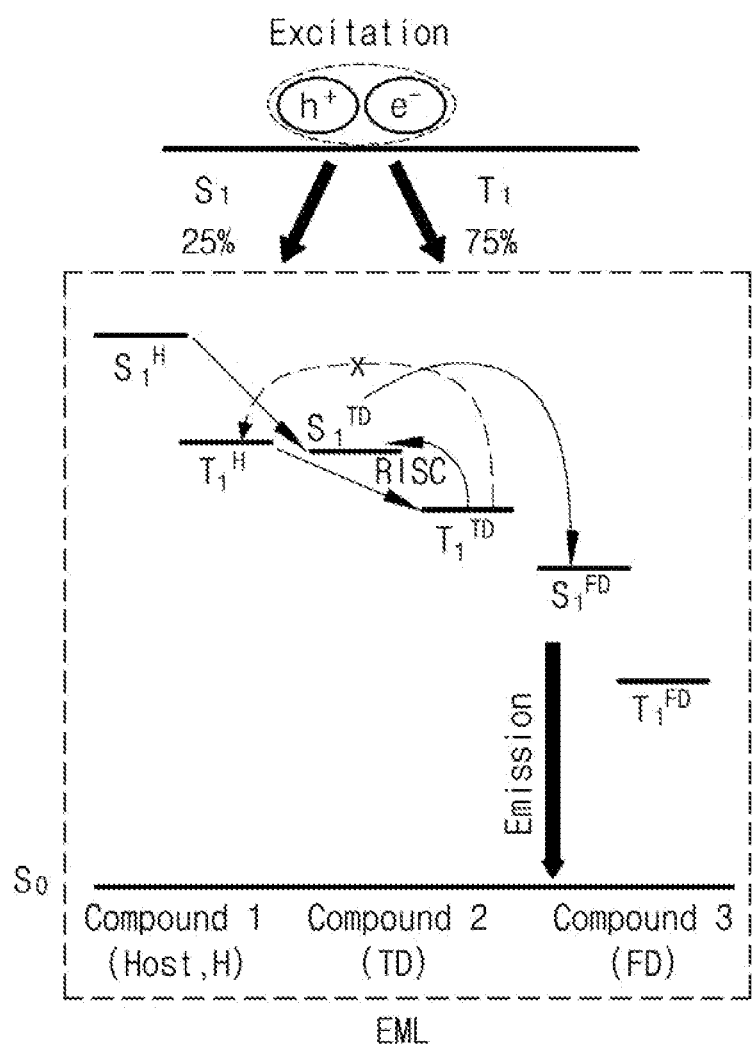
FIG. 6 is a schematic diagram illustrating luminous mechanism by energy level bandgap among luminous materials in accordance with another exemplary aspect of the present disclosure.

When the EML 240A comprise the first compound H of the host, the second compound TD having the delayed fluorescent property and the third compound FD of the fluorescent or phosphorescent material, it is necessary to adjust properly the energy levels among those luminous materials. FIG. 6 is a schematic diagram illustrating luminous mechanism by energy level bandgap among luminous materials in accordance with another exemplary aspect of the present disclosure.

As illustrated in FIG. 6, the second compound TD can have the energy level bandgap $\Delta E_{ST}^{TD}$ between the excited singlet energy level $S_1^{TD}$ and the excited triplet energy level $T_1^{TD}$ equal to or less than about 0.3 eV so as to realize delayed fluorescence (see, FIG. 3). Each of the excited singlet energy level $S_1^H$ and the excited triplet energy level $T_1^H$ of the first compound H of the host in the EML 240A is higher than each of the excited singlet energy level $S_1^{TD}$ and the excited triplet energy level $T_1^{TD}$ of the second, respectively. As an example, the excited triplet energy level $T_1^H$ of the first compound H can be higher than the excited triplet energy level $T_1^{TD}$ of the second compound TD by at least about 0.2 eV, e.g. at least about 0.3 eV, preferably at least about 0.5 eV.

In addition, it is necessary for the EML 240A to implement high luminous efficiency and color purity as well as to transfer exciton energy efficiently from the second compound TD, which is converted to ICT complex state by RISC mechanism in the EML 240A, to the third compound FD of the fluorescent or phosphorescent material in the EML 240A. To this end, the excited triplet energy level $T_1^{TD}$ of the second compound TD is higher than the excited triplet energy level $T_1^{FD}$ of the third compound FD. Optionally, the excited singlet energy level $S_1^{TD}$ of the second compound TD can be higher than the excited singlet energy level $S_1^{FD}$ of the third compound FD. Each of the first and second compounds H and TD can be the compound described in the above aspect.

In addition, exciton energies should be efficiently transferred from the second compound TD of the delayed fluorescent material to the third compound FD of the fluorescent or phosphorescent material to implement hyper fluorescence. As an example, fluorescent or phosphorescent material having absorption (Abs.) spectrum with large overlapping region with the photoluminescence (PL) spectrum of the second compound TD having the delayed fluorescent property can be used as the third compound FD.

The third compound FD can emit blue (B), green (G) or red (R) light. As an example, the fluorescent material that can be used as the third compound FD can emit blue light. In this case, the third compound FD can comprise, but is not limited, to, a pyrene-based compound, an anthracene-based compound, a fluoranthene-based compound and a boron-based compound. For example, the third compound FD of the blue emitting fluorescent material can include any organic compound having the following structure of Chemical Formula 11:

[Chemical Formula 11]

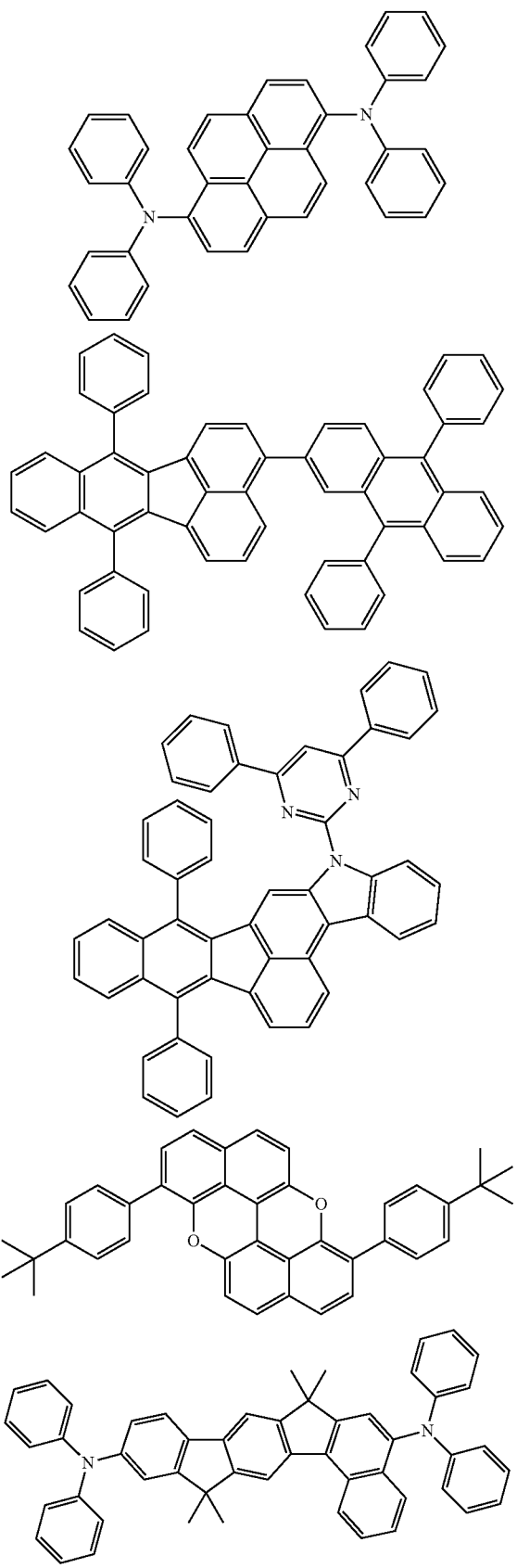

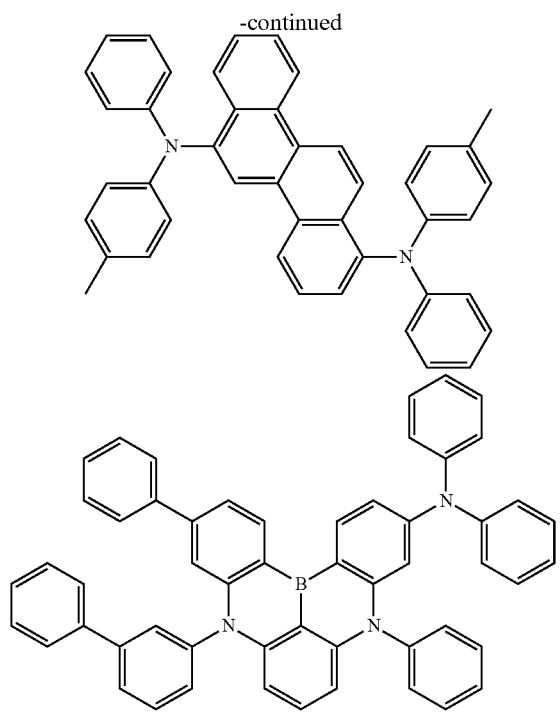

In another alternative aspect, the third compound FD of the green emitting fluorescent material can comprise, but is not limited to, a boron-dipyrromethene (4,4-difluoro-bora-3a,4a-diaza-indacene, BODIPY) core and/or a quinolino-acridine core. As an example, the third compound FD can comprise, but is not limited to, 5,12-dimethylquinolino[2,3-b]acridine-7,14(5H, 12H)-dione, 5,12-diethylquinolino[2,3-b]acridine-7,14(5H, 12H)-dione, 5,12-dibutyl-3,10-difluoroquinolino[2,3-b]acridine-7,14(5H, 12H)-dione, 5,12-dibutyl-3,10-bis(trifluoromethyl)quinolino[2,3-b]acridine-7,14(5H, 12H)-dione, 5,12-dibutyl-2,3,9,10-tetrafluoroquinolino[2,3-b]acridine-7,14(5H, 12H)-dione and 1,1,7,7-tetramethyl-2,3,6,7-tetrahydro-1H,5H-benzo[i,j]quinolizin-9-yl)ethenyl]-4H-pyran-4-ylidene propanedinitrile (DCJTB). Alternatively, the third compound FD can comprise any metal complex emitting red, green or blue light as the phosphorescent material.

In one exemplary aspect, the contents of the first compound H in the EML 240A can be larger than each of the contents of the second compound TD, and the contents of the second compound TD can be larger than the contents of the third compound FD. In this case, the exciton energy can be transferred sufficiently from the second compound TD to the third compound FD. For example, the EML 240A can comprise, but is not limited to, the first compound H between about 60 wt % and about 75 wt %, the second compound TD between about 20 wt % and about 40 wt %, and the third compound FD between about 0.1 wt % and about 5 wt %.

Figure 7:
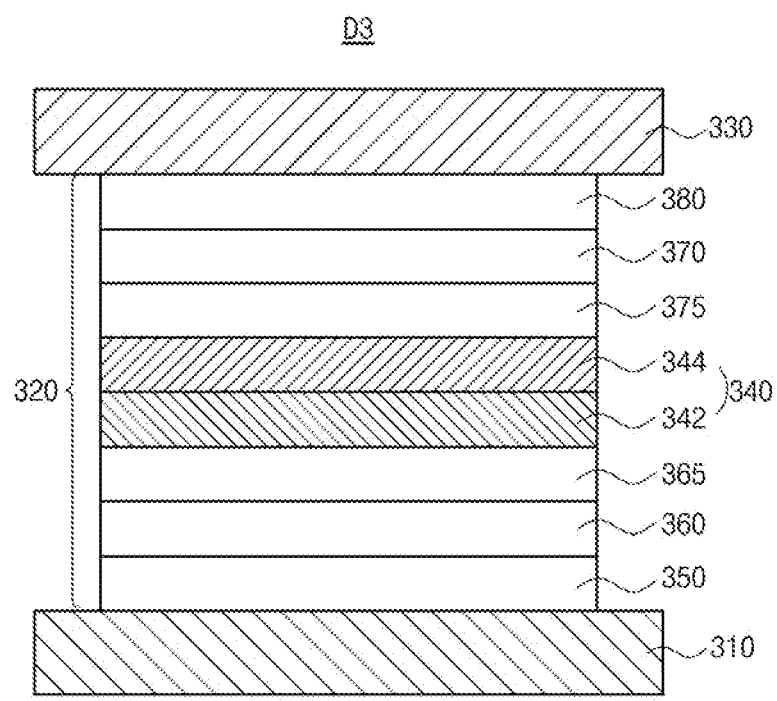
FIG. 7 is a schematic cross-sectional view illustrating an OLED diode in accordance with another exemplary aspect of the present disclosure.
Figure 8:
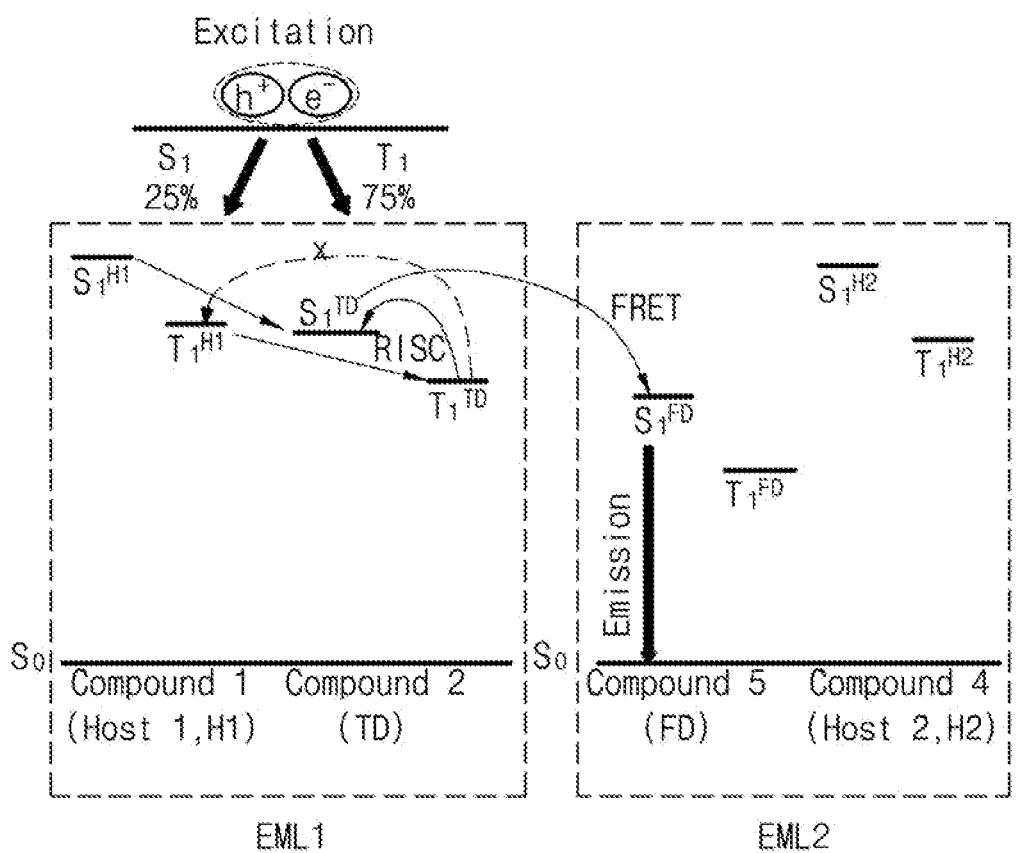
FIG. 8 is a schematic diagram illustrating luminous mechanism by energy level bandgap among luminous materials in accordance with another exemplary aspect of the present disclosure.

The OLEDs in accordance with the previous aspects have a single-layered EML. Alternatively, an OLED in accordance with the present disclosure can include multiple-layered EML. FIG. 7 is a schematic cross-sectional view illustrating an OLED having a double-layered EML in accordance with another exemplary aspect of the present disclosure. FIG. 8 is a schematic diagram illustrating luminous mechanism by energy level bandgap among luminous materials in accordance with another exemplary aspect of the present disclosure.

As illustrated in FIG. 7, the OLED D3 in accordance with this aspect includes first and second electrodes 310 and 330 facing each other and an emissive layer 320 having single emitting part disposed between the first and second electrodes 310 and 330. The organic light emitting display device 100 (FIG. 1) may include a red pixel region, a green pixel region and a blue pixel region, and the OLED D3 may be located in any one of the red green pixel region, the green pixel region and the blue pixel region.

In one exemplary aspect, the emissive layer 320 comprises an EML 340. The emissive layer 320 comprises may comprise at least one of a HTL 360 disposed between the first electrode 310 and the EML 340 and an ETL 370 disposed between the second electrode 330 and the EML 340. Also, the emissive layer 320 may further comprise at least one of a HIL 350 disposed between the first electrode 310 and the HTL 360 and an EIL 380 disposed between the second electrode 330 and the ETL 370. Alternatively, the emissive layer 320 can further comprise an EBL 365 disposed between the HTL 360 and the EML 340 and/or a HBL 375 disposed between the EML 340 and the ETL 370. The configuration of the first and second electrodes 310 and 330 as well as other layers except the EML 340 in the emissive layer 320 can be substantially identical to the corresponding electrodes and layers in the OLEDs D1 and D2.

The EML 340 includes a first EML (EML1, lower EML, first layer) 342 and a second EML (EML2, upper EML, second layer) 344. The EML1 342 is disposed between the EBL 365 and the HBL 375 and the EML2 344 is disposed between the EML1 342 and the HBL 375. One of the EML1 342 and the EML2 344 includes the second compound TD (first dopant) of the delayed fluorescent material, and the other of the EML1 342 and the EML2 344 includes a fifth compound FD (second dopant) of the fluorescent or phosphorescent material. Hereinafter, the EML 340 where the EML1 342 comprises the second compound TD and the EML2 344 comprises the fifth compound FD will be explained.

The EML1 342 comprises the first compound H1 of the organic compound having the structure of Chemical Formulae 1 to 9 as the first host and the second compound TD of the delayed fluorescent material as the first dopant. The triplet exciton energy of the second compound TD in the EML1 342 can be transferred upwardly to its own singlet exciton energy via RISC mechanism (see, FIG. 3). While the second compound TD has high internal quantum efficiency, but it has poor color purity due to its wide FWHM. On the contrary, the EML2 344 comprises the fourth compound H2 as the second host and the fifth compound FD of the fluorescent or phosphorescent material as the second dopant. The fifth compound FD of the fluorescent or phosphorescent material in the EML2 344 has an advantage in terms of color purity due to its narrow FWHM, but its internal quantum efficiency is low because its triplet exciton cannot be involved in the luminescence process.

However, in this exemplary aspect, the singlet exciton energy and the triplet exciton energy of the second compound TD having the delayed fluorescent property in the EML1 342 can be transferred to the fifth compound FD in the EML2 344 disposed adjacently to the EML1 342 by FRET mechanism, and the ultimate light emission occurs in the fifth compound FD within the EML2 344. In other words, the triplet exciton energy of the second compound TD is converted upwardly to its own singlet exciton energy in the EML1 342 by RISC mechanism. Then, the converted singlet exciton energy of the second compound TD is transferred to the singlet exciton energy of the fifth compound FD in the EML2 344.

The fifth compound FD in the EML2 344 can emit light using the triplet exciton energy as well as the singlet exciton energy. As the exciton energy generated at the second compound TD of the delayed fluorescent material in the EML1 342 is transferred efficiently to the fifth compound FD of the fluorescent or phosphorescent material in the EML2 344, the OLED D3 can implement hyper fluorescence. In this case, while the second compound TD having the delayed fluorescent property only acts as transferring exciton energy to the fifth compound FD, substantial light emission is occurred in the EML2 344 including the fifth compound FD of the fluorescent or phosphorescent material. Accordingly, the OLED D3 can improve its quantum efficiency and color purity with narrow FWHM.

Each of the EML1 342 and the EML2 344 includes the first compound H1 of the first host and the fourth compound H2 of the second host, respectively. The exciton energies generated at the first and fourth compounds H1 and H2 should be transferred primarily to the second compound TD. To this end, each of the excited singlet energy levels $S_1^{H1}$ and SP and excited triplet energy levels $T_1^{H1}$ and $T_1^{H2}$ of the first and fourth compounds H1 and H2 is higher than each of the excited singlet energy level $S_1^{TD}$ and the excited triplet energy level $T_1^{TD}$ of the second compound TD having the delayed fluorescent property, respectively. As an example, each of the excited triplet energy levels $T_1^{H1}$ and $T_1^{H2}$ of the first and fourth compounds H1 and H2 can be higher than the excited triplet energy level $T_1^{TD}$ of the second compound TD by at least about 0.2 eV, e.g. at least about 0.3 eV, preferably at least about 0.5 eV.

In addition, the excited singlet energy level $S_1^{H2}$ of the fourth compound H2 in the EML2 344 is higher than the excited singlet energy level $S_1^{FD}$ of the fifth compound FD. Alternatively, the excited triplet energy level $T_1^{H2}$ of the fourth compound H2 can be higher than the excited triplet energy level $T_1^{FD}$ of the fifth compound FD. In this case, the singlet exciton energy generated at the fourth compound H2 can be transferred to the singlet energy of the fifth compound FD.

Moreover, exciton energy should be transferred efficiently from the second compound TD that is converted to ICT complex state by RISC in the EML1 342 to the fifth compound FD of the fluorescent or phosphorescent material in the EML2 344. To this end, the excited singlet energy level $S_1^{TD}$ of the second compound TD in the EML1 342 is higher than the excited singlet energy level $S_1^{FD}$ of the fifth compound FD in the EML2 344. Alternatively, the excited triplet energy level $T_1^{TD}$ of the second compound TD in the EML1 342 is higher than the excited triplet energy level $T_1^{FD}$ of the fifth compound FD in the EML2 344.

Also, the energy level bandgap ($|HOMO^H-HOMO^{TD}|$) between the HOMO energy level ($HOMO^H$) of the first and/or fourth compounds H1 and H2 and the HOMO energy level ($HOMO^{TD}$) of the second compound TD, or the energy level bandgap ($|LUMO^H-LUMO^{TD}|$) between a LUMO energy level ($LUMO^H$) of the first and/or fourth compounds H1 and H2 and the LUMO energy level ($LUMO^{TD}$) of the second compound TD can be equal to or less than about 0.5 eV. When the luminous materials do not satisfy the requirements above, excitons can be quenched as non-radiation at each of the second compound TD or excitons cannot be transferred to the dopants from the hosts, and results in luminous efficiency reduction in the OLED D3.

The first and fourth compounds H1 and H2 can be the same or different from each other. In one exemplary aspect, each of the first and fourth compounds H1 and H2 can comprise independently the organic compound having the structure of Chemical Formulae 1 to 9. The second compound TD of the delayed fluorescent material can the same as the second compound in the above first and second aspects. The fifth compound FD can have narrow FWHM and have Abs. spectrum with wide overlapping region with the PL spectrum of the second compound TD. As an example, the firth compound FD can be the fluorescent or phosphorescent material emitting blue, green or red light. For example, the fifth compound FD can be the same as the third compound described in the second aspect.

In one exemplary aspect, each of the contents of the first and fourth compounds H1 and H2 in the EML1 342 and the EML2 344 can be larger than or equal to the contents of the second and fifth compounds TD and FD in the same layer. Also, the contents of the second compound TD in the EML1 342 can be larger than the contents of the fifth compound FD in the EML2 344. In this case, exciton energy can be transferred sufficiently from the second compound TD to the fifth compound FD via FRET mechanism. As an example, the contents of the second compound TD in the EML1 342 can be, but is not limited to, between about 1 wt % and about 70 wt %, preferably between about 10 wt % and about 50 wt %, and more preferably between about 20 wt % and about 50 wt %. On the contrary, the EML2 344 can comprise the fourth compound H2 between about 90 wt % and about 99 wt %, preferably between about 95 wt % and about 99 wt %, and the fifth compound FD between about 1 wt % and about 10 wt %, preferably between about 1 wt % and about 5 wt %.

In another exemplary aspect, when the EML2 344 is disposed adjacently to the HBL 375, the fourth compound H2, which is included in the EML2 344 together with the fifth compound FD, can be the same material as the HBL 375. In this case, the EML2 344 can have s hole blocking function as well as an emission function. In other words, the EML2 344 can act as a buffer layer for blocking holes. In one aspect, the HBL 375 can be omitted where the EML2 344 can be a hole blocking layer as well as an emitting material layer.

In another aspect, when the EML2 344 is disposed adjacently to the EBL 365, the fourth compound H2 in the EML2 344 can be the same as the EBL 365. In this case, the EML2 344 can have an electron blocking function as well as an emission function. In other words, the EML2 344 can act as a buffer layer for blocking electrons. In one aspect, the EBL 365 can be omitted where the EML2 344 can be an electron blocking layer as well as an emitting material layer.

Figure 9:
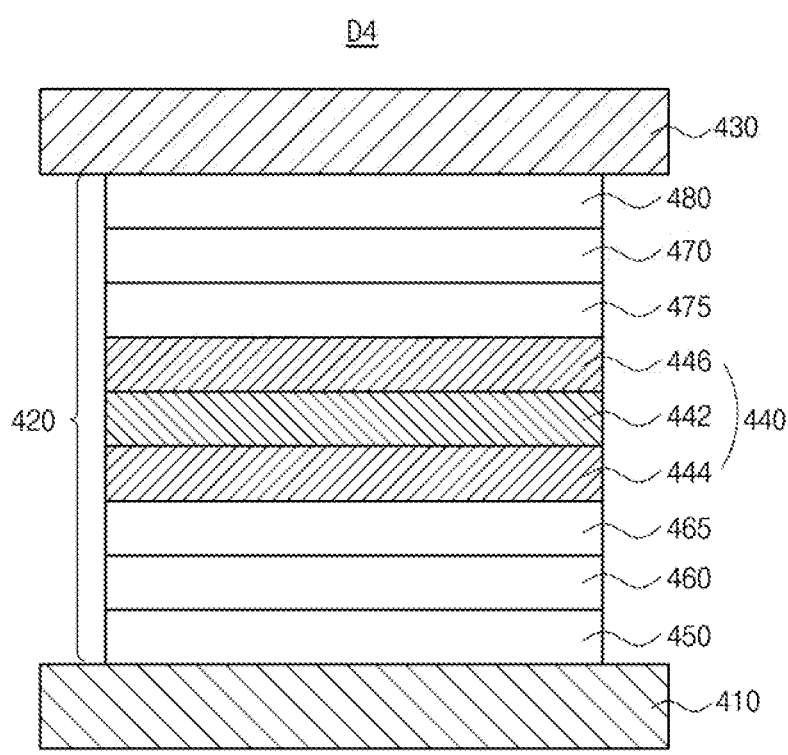
FIG. 9 is a schematic cross-sectional view illustrating an OLED in accordance with another exemplary aspect of the present disclosure.
Figure 10:
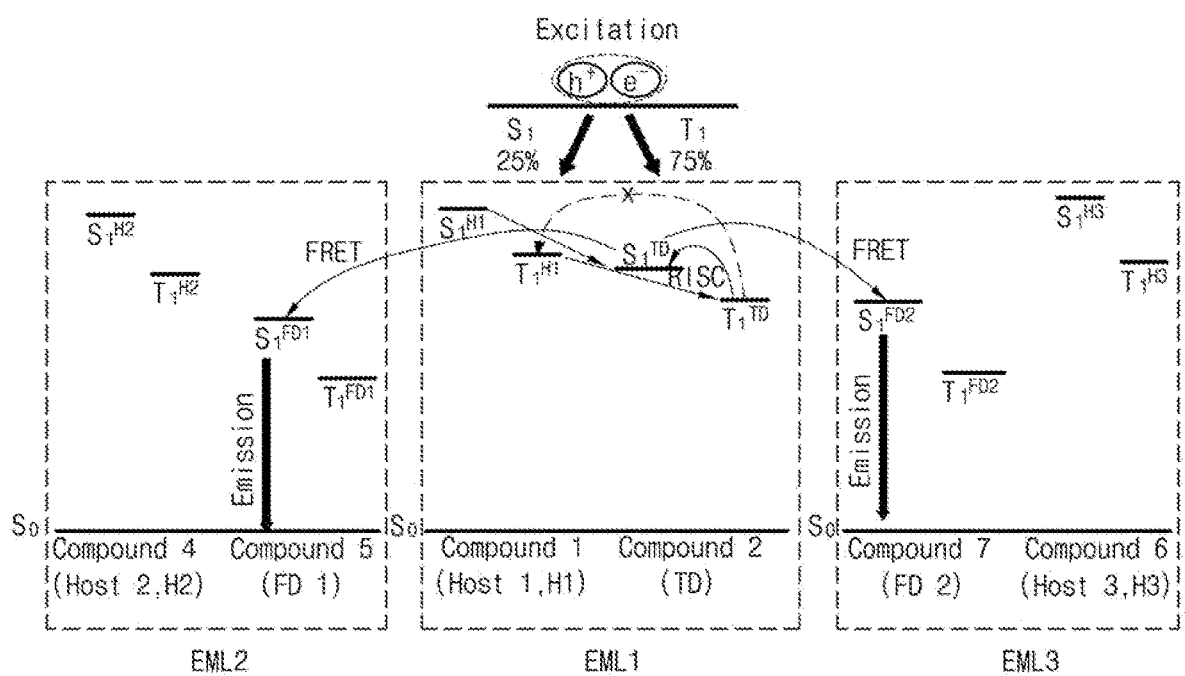
FIG. 10 is a schematic diagram illustrating luminous mechanism by energy level bandgap among luminous materials in accordance with another exemplary aspect of the present disclosure.

An OLED having a triple-layered EML will be explained. FIG. 9 is a schematic cross-sectional view illustrating an OLED having a triple-layered EML in accordance with another exemplary aspect of the present disclosure. FIG. 10 is a schematic diagram illustrating luminous mechanism by energy level bandgap among luminous materials in accordance with another exemplary aspect of the present disclosure.

As illustrated in FIG. 9, the OLED D4 in this aspect comprises first and second electrodes 410 and 430 facing each other and an emissive layer 420 having a single emitting part disposed between the first and second electrodes 410 and 430. The organic light emitting display device 100 (FIG. 1) may include a red pixel region, a green pixel region and a blue pixel region, and the OLED D4 may be located in any one of the red green pixel region, the green pixel region and the blue pixel region.

In one exemplary aspect, the emissive layer 420 having single emitting part comprises a three-layered EML 440. The emissive layer 420 may comprise at least one of a HTL 460 disposed between the first electrode 410 and the EML 440 and an ETL 470 disposed between the second electrode 430 and the EML 440. Also, the emissive layer 420 may further comprise at least one of a HIL 450 disposed between the first electrode 410 and the HTL 460 and an EIL 480 disposed between the second electrode 430 and the ETL 470. Alternatively, the emissive layer 420 can further comprise an EBL 465 disposed between the HTL 460 and the EML 440 and/or a HBL 475 disposed between the EML 440 and the ETL 470. The configurations of the first and second electrodes 410 and 430 as well as other layers except the EML 440 in the emissive layer 420 can be substantially identical to the corresponding electrodes and layers in the OLEDs D1, D2 and D3.

The EML 440 comprises a first EML (EML1, middle EML, first layer) 442, a second EML (EML2, lower EML, second layer) 444 and a third EML (EML3, upper EML, third layer) 446. The EML1 442 is disposed between the EBL 465 and the HBL 475, the EML2 444 is disposed between the EBL 465 and the EML1 442 and the EML3 446 is disposed between the EML1 442 and the HBL 475.

The EML1 442 comprises the second compound TD of the delayed fluorescent material (first dopant), and each of the EML2 444 and the EML3 446 comprises the fifth compound FD1 (second dopant) and a seventh compound FD2 (third dopant) each of can be the fluorescent or phosphorescent material, respectively. In addition, each of the EML1 442, EML2 444 and EML3 446 further includes the first, fourth and sixth compounds H1, H2 and H3 each of which can be the first to third hosts, respectively.

In accordance with this aspect, the singlet energy as well as the triplet energy of the second compound TD, i.e. the delayed fluorescent material in the EML1 442 can be transferred to the fifth and seventh compounds FD1 and FD2, i.e. the fluorescent or phosphorescent material each of which is included in the EML2 444 and EML3 446 disposed adjacently to the EML1 442 by FRET mechanism. Accordingly, the ultimate emission occurs in the fifth and seventh compounds FD1 and FD2 in the EML2 444 and the EML3 446.

In other words, the triplet exciton energy of the second compound TD having the delayed fluorescent property in the EML1 442 is converted upwardly to its own singlet exciton energy by RISC mechanism, then the singlet exciton energy of the second compound TD is transferred to the singlet exciton energy of the fifth and seventh compounds FD1 and FD2 in the EML2 444 and the EML3 446 because the second compound TD has the excited singlet energy level $S_1^{TD}$ higher than each of the excited singlet energy levels $S_1^{FD1}$ and $S_1^{FD2}$ of the fifth and seventh compounds FD1 and FD2 (see, FIG. 10).

Since the fifth and seventh compounds FD1 and FD2 in the EML2 444 and EML3 446 can emit light using the singlet exciton energy and the triplet exciton energy derived from the second compound TD, the OLED D4 can improve its luminous efficiency. In addition, since each of the fifth and seventh compounds FD1 and FD2 has relatively narrow FWHM compared to the second compound TD, the OLED D4 can enhance its color purity. Particularly, in case of using the fifth and seventh compounds FD1 and FD2 having Abs. spectrum with large overlapping area with the PL spectrum of the second compound TD, exciton energy can be transferred efficiently from the second compound TD to the fifth and seventh compounds FD1 and FD2. In this case, while the second compound TD only acts as transferring exciton energy to the fifth and seventh compounds FD1 and FD2, substantial light emission is occurred in the EML2 444 and the EML3 446 including the fifth and seventh compounds FD1 and FD2.

In addition, it is necessary to adjust luminous materials introduced into the EML1 442, the EML2 444 and the EML3 446 so as to implement efficient luminescence. With referring to FIG. 10, each of the excited singlet energy levels $S_1^{H1}$, $S_1^{H2}$ and $S_1^{H3}$ and the excited triplet energy levels $T_1^{H1}$, $T_1^{H2}$ and $T_1^{H3}$ of the first, fourth and sixth compounds H1, H2 and H3, each of which is the first to third hosts, respectively, is higher than each of the excited singlet energy level $S_1^{TD}$ and the excited triplet energy level $T_1^{TD}$ of the second compound TD, respectively.

Also, exciton energy should be transferred efficiently from the second compound TD that is converted to ICT complex state by RISC in the EML1 442 to the fifth and seventh compounds FD1 and FD2 each of which is the fluorescent or phosphorescent material in the EML2 444 and in the EML3 446. To this end, the excited singlet energy level $S_1^{TD}$ of the second compound TD in the EML1 442 is higher than each of the excited singlet energy levels $S_1^{FD1}$ and $S_1^{FD2}$ of the fifth and seventh compounds FD1 and FD2 in the EML2 444 and the EML3 446. Alternatively, the excited triplet energy level $T_1^{TD}$ of the second compound TD in the EML1 442 is higher than each of the excited triplet energy levels $T_1^{FD1}$ and $T_1^{FD2}$ of the fifth and seventh compounds FD1 and FD2 in the EML2 444 and the EML3 446.

In addition, the exciton energy transferred from the second compound TD of the delayed fluorescent material to the fifth and seventh compounds FD1 and FD2 of the fluorescent or phosphorescent material should not transferred to the fourth and sixth compounds H2 and H3 in order to realize efficient luminescence. To this end, each of the excited singlet energy levels SP and SP of the fourth and sixth compounds H2 and H3, each of which is the second and third hosts, respectively, is higher than each of the excited singlet energy levels $S_1^{FD1}$ and $S_1^{FD2}$ of the fifth and seventh compounds FD1 and FD2, each of which is the fluorescent or phosphorescent material. Alternatively, each of the excited triplet energy levels $T_1^{H2}$ and $T_1^{H3}$ of the fourth and sixth compounds H2 and H3 can be higher than each of the excited triplet energy levels $T_1^{FD1}$ and $T_1^{FD2}$ of the fifth and seventh compounds FD1 and FD2.

As described above, each of the EML1 442, the EML2 444 and the EML3 446 comprises the first, fourth and sixth compounds H1, H2 and H3 each of which is the first to third hosts, respectively. The first, fourth and sixth compounds H1, H2 and H3 can be the same or different from each other. In one exemplary aspect, each of the first, fourth and sixth compounds H1, H2 and H3 can comprise independently the organic compound having the structure of Chemical Formulae 1 to 9. The second compound TD of the delayed fluorescent material can be the same as the second compound in the above aspects. Each of the fifth and seventh compounds FD1 and FD2 can be independently the same as the third compound FD in the second aspect.

In one exemplary aspect, the contents of the second compound TD in the EML1 442 can be larger than the contents of each of the fifth and seventh compounds FD1 and FD2 in the EML2 444 and in the EML3 446. In this case, exciton energy can be transferred sufficiently from the second compound TD to the fifth and seventh compounds FD1 and FD2 via FRET mechanism. As an example, the contents of the second compound TD in the EML1 442 can be, but is not limited to, about 1 wt % to about 70 wt %, preferably about 10 wt % to about 50 wt %, and more preferably about 20 wt % to about 50 wt %. On the contrary, each of the EML2 444 and the EML3 446 can comprise the fourth or sixth compound H2 or H3 between about 90 wt % and about 99 wt %, preferably between about 95 wt % and about 99 wt %, and the fifth or seventh compound FD1 or FD2 between about 1 wt % and about 10 wt %, preferably between about 1 wt % and about 5 wt %.

In one exemplary aspect, when the EML2 444 is disposed adjacently to the EBL 465, the fourth compound H2 in the EML2 444 can be the same material as the EBL 465. In this case, the EML2 444 can have an electron blocking function as well as an emission function. In other words, the EML2 444 can act as a buffer layer for blocking electrons. In one aspect, the EBL 465 can be omitted where the EML2 444 can be an electron blocking layer as well as an emitting material layer.

When the EML3 446 is disposed adjacently to the HBL 475, the sixth compound H3 in the EML3 446 can be the same material as the HBL 475. In this case, the EML3 446 can have a hole blocking function as well as an emission function. In other words, the EML3 446 can act as a buffer layer for blocking holes. In one aspect, the HBL 475 can be omitted where the EML3 446 can be a hole blocking layer as well as an emitting material layer.

In still another exemplary aspect, the fourth compound H2 in the EML2 444 can be the same material as the EBL 465 and the sixth compound H3 in the EML3 446 can be the same material as the HBL 475. In this aspect, the EML2 444 can have an electron blocking function as well as an emission function, and the EML3 446 can have a hole blocking function as well as an emission function. In other words, each of the EML2 444 and the EML3 446 can act as a buffer layer for blocking electrons or hole, respectively. In one aspect, the EBL 465 and the HBL 475 can be omitted where the EML2 444 can be an electron blocking layer as well as an emitting material layer and the EML3 446 can be a hole blocking layer as well as an emitting material layer.

Figure 11:
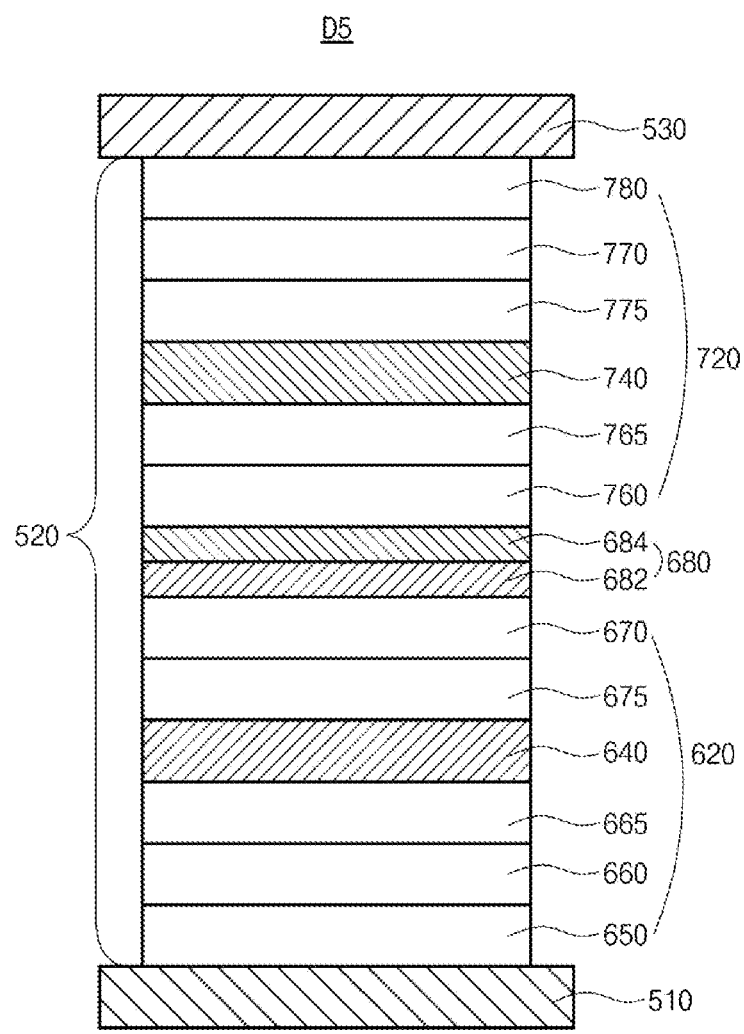
FIG. 11 is a schematic cross-sectional view illustrating an OLED in accordance with still another exemplary aspect of the present disclosure.

In an alternative aspect, an OLED may include multiple emitting parts. FIG. 11 is a schematic cross-sectional view illustrating an OLED in accordance with still another exemplary aspect of the present disclosure.

As illustrated in FIG. 10, the OLED D5 comprises first and second electrodes 510 and 530 facing each other and an emissive layer 520 with two emitting parts disposed between the first and second electrodes 510 and 530. The organic light emitting display device 100 (FIG. 1) includes a red pixel region, a green pixel region and a blue pixel region, and the OLED D5 may be disposed in any one of the red pixel region, the green pixel region and the blue pixel region. The first electrode 510 may be an anode and the second electrode 530 may be a cathode.

The emissive layer 520 includes a first emitting part 620 that includes a first EML (EML1) 640, and a second emitting part 720 that includes a second EML (EML2) 740. Also, the emissive layer 520 may further comprise a charge generation layer (CGL) 680 disposed between the first emitting part 620 and the second emitting part 720.

The CGL 680 is disposed between the first and second emitting parts 620 and 720 so that the first emitting part 620, the CGL 680 and the second emitting part 720 are sequentially disposed on the first electrode 510. In other words, the first emitting part 620 is disposed between the first electrode 510 and the CGL 680 and the second emitting part 720 is disposed between the second electrode 530 and the CGL 680.

The first emitting part 620 comprises the EML1 640. The first emitting part 620 may further comprise at least one of a first HTL (HTL1) 660 disposed between the first electrode 510 and the EML1 640, a HIL 650 disposed between the first electrode 510 and the HTL1 660 and a first ETL (ETL1) 670 disposed between the EML1 640 and the CGL 680. Alternatively, the first emitting part 620 may further comprise a first EBL (EBL1) 665 disposed between the HTL1 660 and the EML1 640 and/or a first HBL (HBL1) 675 disposed between the EML1 640 and the ETL1 670.

The second emitting part 720 comprises the EML2 740. The second emitting part 720 may further comprise at least one of a second HTL (HTL2) 760 disposed between the CGL 680 and the EML2 740, a second ETL (ETL2) 770 disposed between the EML2 740 and the second electrode 530 and an EIL 780 disposed between the ETL2 770 and the second electrode 530. Alternatively, the second emitting part 720 may further comprise a second EBL (EBL2) 765 disposed between the HTL2 760 and the EML2 740 and/or a second HBL (HBL2) 775 disposed between the EML2 740 and the ETL2 770.

The CGL 680 is disposed between the first emitting part 620 and the second emitting part 720. The first emitting part 620 and the second emitting part 720 are connected via the CGL 680. The CGL 680 may be a PN-junction CGL that junctions an N-type CGL (N-CGL) 682 with a P-type CGL (P-CGL) 684.

The N-CGL 682 is disposed between the ETL1 670 and the HTL2 760 and the P-CGL 684 is disposed between the N-CGL 682 and the HTL2 760. The N-CGL 682 transports electrons to the EML1 640 of the first emitting part 620 and the P-CGL 684 transport holes to the EML2 740 of the second emitting part 720. In one exemplary aspect, the N-CGL 682 may comprise the organic compound having the structure of Chemical Formulae 1 to 9.

In this aspect, each of the EML1 640 and the EML2 740 may be a red emitting material layer, a green emitting material layer or a blue emitting material layer. For example, at least one of the EML1 640 and the EML2 740 comprise a first compound of a host, a second compound of delayed fluorescent material and/or a third compound of fluorescent or phosphorescent material. For example, the EML1 640 may comprise the first compound, the second compound and the third compound.

When the EML1 640 includes the first compound having the structure of Chemical Formulae 1 to 9, the second compound and the third compound, the contents of the first compound may be larger than the contents of the second compound, and the contents of the second compound is larger than the contents of the third compound. In this case, exciton energy can be transferred efficiently from the second compound to the third compound. As an example, each of the contents of the first to third compounds in the EML1 640 may be, but is not limited to, about 60 wt % to about 75 wt %, about 20 wt % to about 40 wt % and about 0.1 wt % to about 5 wt %, respectively.

In one exemplary aspect, the EML2 740 may comprise the first compound of a host having the structure of Chemical Formulae 1 to 9, the second compound of delayed fluorescent material and/or the third compound of fluorescent or phosphorescent material similar to the EML1 640. Alternatively, the EML2 740 may include another compound that is different from at least one of the second compound and the third compound in the EML1 640, and thus the EML2 740 may emit light different from the light emitted from the EML1 640 or may have different luminous efficiency different from the luminous efficiency of the EML1 640.

In FIG. 11, each of the EML1 640 and the EML2 740 has a single-layered structure. Alternatively, each of the EML1 640 and the EML2 740, each of which may include the first to third compounds, may have a double-layered structure (FIG. 7) or a triple-layered structure (FIG. 9), respectively.

In the OLED D5, the singlet exciton energy of the second compound of delayed fluorescent material is transferred to the third compound of fluorescent or phosphorescent material, and the final emission is occurred at the third compound. Accordingly, the OLED D5 can have excellent luminous efficiency and color purity. In addition, the OLED D4 has a double stack structure of a red, green or blue emitting material layer, the OLEO D5 improve its color sense or optimize its luminous efficiency.

Figure 12:
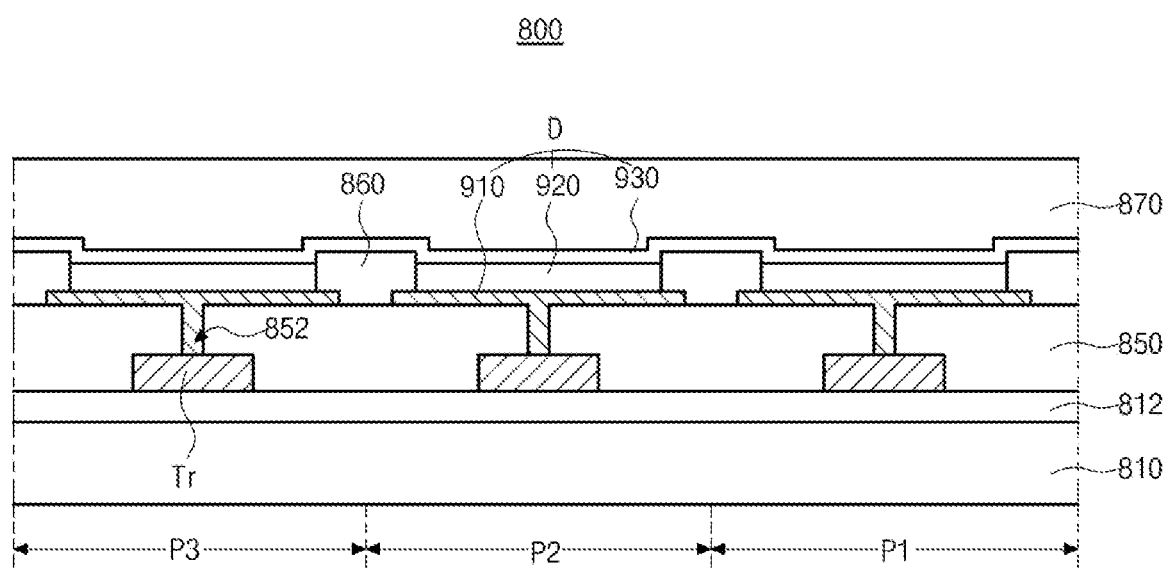
FIG. 12 is a schematic cross-sectional view illustrating an organic light emitting display device in accordance with another exemplary aspect of the present disclosure.

FIG. 12 is a schematic cross-sectional view illustrating an organic light emitting display device in accordance with another exemplary aspect of the present disclosure. As illustrated in FIG. 12, an organic light emitting display device 800 includes a substrate 810 that defines first to third pixel regions P1, P2 and P3, a thin film transistor Tr disposed over the substrate 810 and an OLED D disposed over the thin film transistor Tr and connected to the thin film transistor Tr. As an example, the first pixel region P1 may be a blue pixel region, the second pixel region P2 may be a green pixel region and the third pixel region P3 may be a red pixel region.

The substrate 810 may be a glass substrate or a flexible substrate. For example, the flexible substrate may be any one of a PI substrate, a PES substrate, a PEN substrate, a PET substrate and a PC substrate.

A buffer layer 812 is disposed over the substrate 810 and the thin film transistor Tr is disposed over the buffer layer 812. The buffer layer 812 may be omitted. As illustrated in FIG. 1, the thin film transistor Tr includes a semiconductor layer, a gate electrode, a source electrode and a drain electrode and acts as a driving element.

A passivation layer 850 is disposed over the thin film transistor Tr. The passivation layer 850 has a flat top surface and a drain contact hole 852 that exposes a drain electrode of the thin film transistor Tr.

The OLED D is disposed over the passivation layer 850, and includes a first electrode 910 that is connected to the drain electrode of the thin film transistor Tr, an emissive layer 920 and a second electrode 930 each of which is disposed sequentially on the first electrode 910. The OLED D is disposed in each of the first to third pixel regions P1, P2 and P3 and emits different light in each pixel region. For example, the OLED D in the first pixel region P1 may emit blue light, the OLED D in the second pixel region P2 may emit green light and the OLED D in the third pixel region P3 may emit red light.

The first electrode 910 is separately formed for each of the first to third pixel regions P1, P2 and P3, and the second electrode 930 corresponds to the first to third pixel regions P1, P2 and P3 and is formed integrally.

The first electrode 910 may be one of an anode and a cathode, and the second electrode 930 may be the other of the anode and the cathode. In addition, one of the first electrode 910 and the second electrode 930 is a transmissive (or semi-transmissive) electrode and the other of the first electrode 910 and the second electrode 930 is a reflective electrode.

For example, the first electrode 910 may be an anode and may include conductive material having a relatively high work function value, i.e., a transparent conductive oxide layer of transparent conductive oxide (TCO). The second electrode 930 may be a cathode and may include conductive material having relatively low work function value, i.e., a metal material layer of low-resistant metal. For example, the first electrode 910 may include any one of ITO, IZO, ITZO, SnO, ZnO, ICO and AZO, and the second electrode 930 may include Al, Mg, Ca, Ag, alloy thereof or combination thereof.

When the organic light emitting display device 800 is a bottom-emission type, the first electrode 910 may have a single-layered structure of a transparent conductive oxide layer.

Alternatively, when the organic light emitting display device 800 is a top-emission type, a reflective electrode or a reflective layer may be disposed under the first electrode 910. For example, the reflective electrode or the reflective layer may include, but is not limited to, Ag or APC alloy. In the OLED D of the top-emission type, the first electrode 910 may have a triple-layered structure of ITO/Ag/ITO or ITO/APC/ITO. Also, the second electrode 930 is thin so as to have light-transmissive (or semi-transmissive) property.

A bank layer 860 is disposed on the passivation layer 850 in order to cover edges of the first electrode 910. The bank layer 860 corresponds to each of the first to third pixel regions P1, P2 and P3 and exposes a center of the first electrode 910.

The emissive layer 920 is disposed on the first electrode 910. In one exemplary aspect, the emissive layer 920 may have a single-layered structure of an EML. Alternatively, the emissive layer 920 may include at least one of a HIL, a HTL, and an EBL disposed sequentially between the first electrode 910 and the EML and/or a HBL, an ETL and an EIL disposed sequentially between the EML and the second electrode 930.

In one exemplary aspect, the EML of the emissive layer 930 in the first pixel region P1 of the blue pixel region may comprise a first compound of a host, a second compound of blue delayed fluorescent material and/or a third compound of blue fluorescent or phosphorescent material. The EML of the emissive layer 930 in the second pixel region P2 of the green pixel region may comprise a first compound of a host, a second compound of green delayed fluorescent material and/or a third compound of green fluorescent or phosphorescent material. The EML of the emissive layer 930 in the third pixel region P3 of the red pixel region may comprise a first compound of a host, a second compound of red delayed fluorescent material and/or a third compound of red fluorescent or phosphorescent material. In this case, the EML in each of the first to third pixel regions P1, P2 and P3 may have a single-layered, double-layered or a triple-layered structure.

Alternatively, the EML of the EML 930 located in any one of the first to third pixel regions P1, P2 and P3 may comprise other organic compound than the first to third compounds.

An encapsulation film 870 is disposed over the second electrode 930 in order to prevent outer moisture from penetrating into the OLED D. The encapsulation film 870 may have, but is not limited to, a triple-layered structure of a first inorganic insulating film, an organic insulating film and a second inorganic insulating film.

The organic light emitting display device 800 may have a polarizer in order to decrease external light reflection. For example, the polarizer may be a circular polarizer. When the organic light emitting display device 800 is a bottom-emission type, the polarizer may be disposed under the substrate 810. Alternatively, when the organic light emitting display device 800 is a top emission type, the polarizer may be disposed over the encapsulation film 870.

Figure 13:
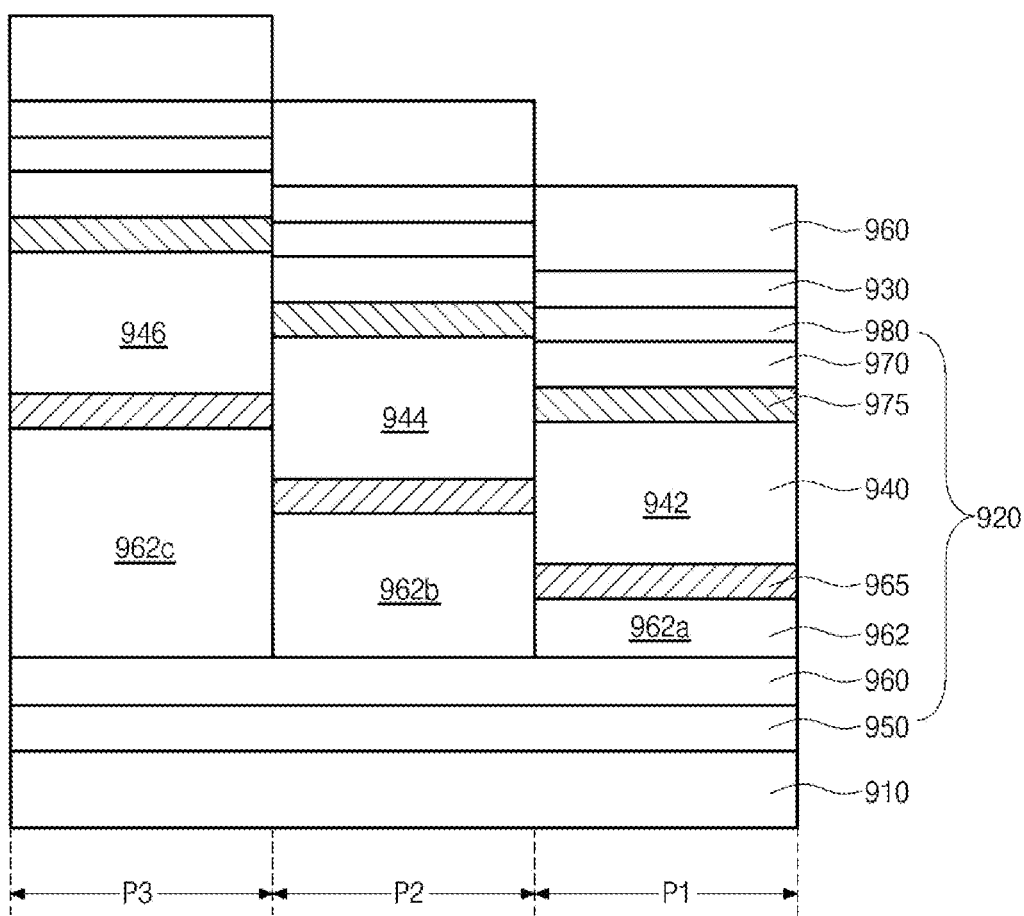
FIG. 13 is a schematic cross-sectional view illustrating an OLED in accordance with still another exemplary aspect of the present disclosure.

FIG. 13 is a schematic cross-sectional view illustrating an OLED in accordance with still another exemplary aspect of the present disclosure. As illustrated in FIG. 13, the OLED D6 comprises a first electrode 910, a second electrode 930 facing the first electrode 910 and an emissive layer 920 disposed between the first and second electrodes 910 and 930.

The first electrode 910 may be an anode and the second electrode 930 may be a cathode. As an example, the first electrode 910 may be a reflective electrode and the second electrode 930 may be a transmissive (or semi-transmissive) electrode.

The emissive layer 920 comprises an EML 940. The emissive layer 930 may comprise at least one of a HTL 960 disposed between the first electrode 910 and the EML 940 and an ETL 970 disposed between the second electrode 930 and the EML 940. Also, the emissive layer 920 may further comprise at least one of a HIL 950 disposed between the first electrode 910 and the HTL 960 and an EIL 980 disposed between the second electrode 930 and the ETL 970. Alternatively, the emissive layer 920 may further comprise an EBL 965 disposed between the HTL 960 and the EML 940 and/or a HBL 975 disposed between the EML 940 and the ETL 970.

In addition, the emissive layer 920 may further comprise an auxiliary hole transport layer (auxiliary HTL) 962 disposed between the HTL 960 and the EBL 965. The auxiliary HTL 962 may comprise a first auxiliary HTL 962a located in the first pixel region P1, a second auxiliary HTL 962b located in the second pixel region P2 and a third auxiliary HTL 962c located in the third pixel region P3.

The first auxiliary HTL 962a has a first thickness, the second auxiliary HTL 962b has a second thickness and the third auxiliary HTL 962c has a third thickness. The first thickness is less than the second thickness and the second thickness is less than the third thickness. Accordingly, the OLED D6 has a micro-cavity structure.

Owing to the first to third auxiliary HTLs 962a, 962b and 962c having different thickness to each other, the distance between the first electrode 910 and the second electrode 930 in the first pixel region P1 emitting light in the first wavelength range (blue light) is less than the distance between the first electrode 910 and the second electrode 930 in the second pixel region P2 emitting light in the second wavelength (green light). Also, the distance between the first electrode 910 and the second electrode 930 in the second pixel region P2 emitting light in the second wavelength is less than the distance between the first electrode 910 and the second electrode 930 in the third pixel region P3 emitting in the third wavelength (red light). Accordingly, the OLED D6 has improved luminous efficiency.

In FIG. 13, the first auxiliary HTL 962a is located in the first pixel region P1. Alternatively, the OLED D6 may implement the micro-cavity structure without the first auxiliary HTL 962a. In addition, a capping layer may be disposed over the second electrode in order to improve out-coupling of the light emitted from the OLED D6.

The EML 940 comprises a first EML (EML1) 942 located in the first pixel region P1, a second EML (EML2) 944 located in the second pixel region P2 and a third EML (EML3) 946 located in the third pixel region P3. Each of the EML1 942, the EML2 944 and the EML3 946 may be a blue EML, a green EML and a red EML, respectively.

In one exemplary aspect, the EML1 942 located in the first pixel region P1 may comprise a first compound f a host, a second compound of blue delayed fluorescent material and/or a third compound of blue fluorescent or phosphorescent material. The first compound may be an organic compound having the structure of Chemical Formulae 1 to 9. The EML2 944 located in the second pixel region P2 may comprise a first compound f a host, a second compound of green delayed fluorescent material and/or a third compound of green fluorescent or phosphorescent material. The EML3 944 located in the third pixel region P3 may comprise a first compound f a host, a second compound of red delayed fluorescent material and/or a third compound of red fluorescent or phosphorescent material. In this case, each of the EML1 942, the EML2 944 and the EML3 may have a single-layered structure, a double-layered structure (FIG. 7) or a triple-layered structure (FIG. 9).

When each of the EML1 942, the EML2 944 and the EML3 includes the first compound, the second compound and the third compound, the contents of the first compound may be larger than the contents of the second compound, and the contents of the second compound is larger than the contents of the third compound. In this case, exciton energy can be transferred efficiently from the second compound to the third compound As an example, each of the contents of the first to third compounds in each of the EML1 942, the EML2 944 and the EML3 946 may be, but is not limited to, about 60 wt % to about 75 wt %, about 20 wt % to about 40 wt % and about 0.1 wt % to about 5 wt %, respectively.

In another exemplary aspect, at least one of the EML1 942, the EML2 944 and the EML3 946 may include the first to third compound and the rest of the EML1 942, the EML2 944 and the EML3 946 may include other compound than the first to the third compounds. The EML1 942, the EML2 944 and the EML3 946 including the first to third compounds may have a single-layered structure, a double-layered structure or a triple-layered structure.

For example, the EML1 942 in the first pixel region P1 may include the first compound of the host, a second compound of the blue delayed fluorescent material and/or a third compound of the blue fluorescent or phosphorescent material. The EML2 944 in the second pixel region P2 may include a host and a green dopant and the EML3 946 in the third pixel region P3 may include a host and a red dopant. In this case, the host of the EML2 944 and/or the EML3 944 may include the first compound. Each of the green dopant and the red dopant may include at least one of the green or red phosphorescent material, the green or red fluorescent material and the green or red delayed fluorescent material.

The OLED D6 emits blue light, green light and red light in each of the first to third pixel regions P1, P2 and P3 so that the organic light emitting display device 800 (FIG. 12) may implement a full-color image.

The organic light emitting display device 800 may further comprise a color filter layer corresponding to the first to third pixel regions P1, P2 and P3 for improving color purity of the light emitted from the OLED D. As an example, the color filter layer may comprise a first color filter layer (blue color filter layer) corresponding to the first pixel region P1, the second color filter layer (green color filter layer) corresponding to the second pixel region P2 and the third color filter layer (red color filter layer) corresponding to the third pixel region P3.

When the organic light emitting display device 800 is a bottom-emission type, the color filter layer may be disposed between the OLED D and the substrate 810. Alternatively, when the organic light emitting display device 800 is a top-emission type, the color filter layer may be disposed over the OLED D.

Figure 14:
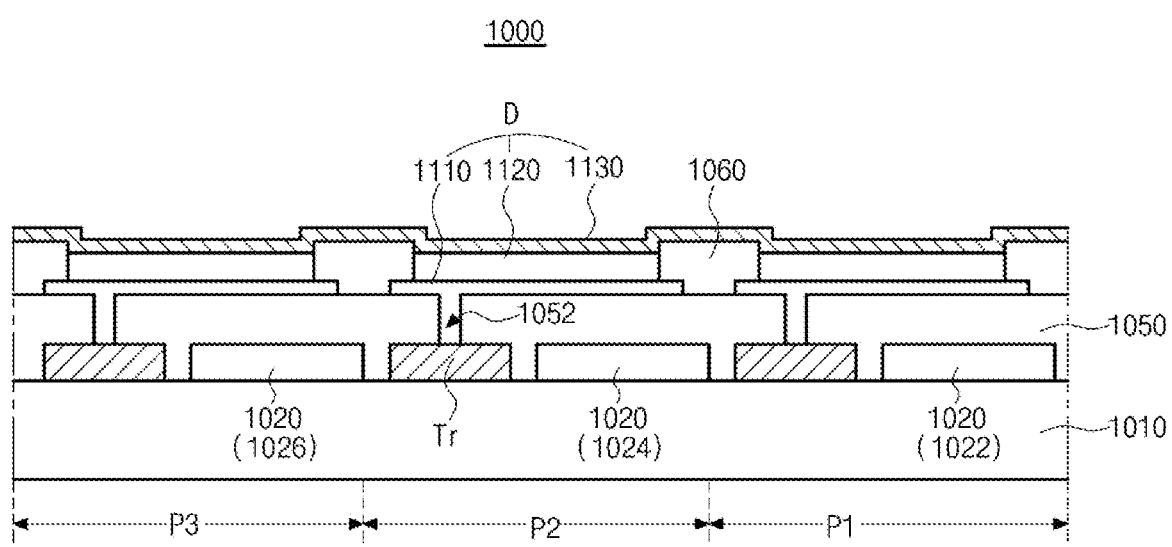
FIG. 14 is a schematic cross-sectional view illustrating an organic light emitting display device in accordance with still another exemplary aspect of the present disclosure.

FIG. 14 is a schematic cross-sectional view illustrating an organic light emitting display device in accordance with still another exemplary aspect of the present disclosure. As illustrated in FIG. 14, the organic light emitting display device 1000 comprise a substrate 1010 defining a first pixel region P1, a second pixel region P2 and a third pixel region P3, a thin film transistor Tr disposed over the substrate 1010, an OLED D disposed over the thin film transistor Tr and connected to the thin film transistor Tr and a color filter layer 1020 corresponding to the first to third pixel regions P1, P2 and P3. As an example, the first pixel region P1 may be a blue pixel region, the second pixel region P2 may be a green pixel region and the third pixel region P3 may be a red pixel region.

The substrate 1010 may be a glass substrate or a flexible substrate. For example, the flexible substrate may be any one of a PI substrate, a PES substrate, a PEN substrate, a PET substrate and a PC substrate. The thin film transistor Tr is located over the substrate 1010. Alternatively, a buffer layer may be disposed over the substrate 1010 and the thin film transistor Tr may be disposed over the buffer layer. As illustrated in FIG. 1, the thin film transistor Tr includes a semiconductor layer, a gate electrode, a source electrode and a drain electrode and acts as a driving element.

The color filter layer 1020 is located over the substrate 1010. As an example, the color filter layer 1020 may comprise a first color filter layer 1022 corresponding to the first pixel region P1, a second color filter layer 1024 corresponding to the second pixel region P2 and a third color filter layer 1026 corresponding to the third pixel region P3. The first color filter layer 1022 may be a blue color filter layer, the second color filter layer 1024 may be a green color filter layer and the third color filter layer 1026 may be a red color filter layer. For example, the first color filter layer 1022 may comprise at least one of blue dye or green pigment, the second color filter layer 1024 may comprise at least one of green dye or red pigment and the third color filter layer 1026 may comprise at least one of red dye or blue pigment.

A passivation layer 1050 is disposed over the thin film transistor Tr and the color filter layer 1020. The passivation layer 1050 has a flat top surface and a drain contact hole 1052 that exposes a drain electrode of the thin film transistor Tr.

The OLED D is disposed over the passivation layer 1050 and corresponds to the color filter layer 1020. The OLED D includes a first electrode 1110 that is connected to the drain electrode of the thin film transistor Tr, and an emissive layer 1120 and a second electrode 1130 each of which is disposed sequentially on the first electrode 1110. The OLED D emits white light in the first to third pixel regions P1, P2 and P3.

The first electrode 1110 is separately formed for each of the first to third pixel regions P1, P2 and P3, and the second electrode 1130 corresponds to the first to third pixel regions P1, P2 and P3 and is formed integrally.

The first electrode 1110 may be one of an anode and a cathode, and the second electrode 1130 may be the other of the anode and the cathode. In addition, the first electrode 1110 may be a transmissive (or semi-transmissive) electrode and the second electrode 1130 may be a reflective electrode.

For example, the first electrode 1110 may be an anode and may include conductive material having a relatively high work function value, i.e., a transparent conductive oxide layer of transparent conductive oxide (TCO). The second electrode 1130 may be a cathode and may include conductive material having relatively low work function value, i.e., a metal material layer of low-resistant metal. For example, the transparent conductive oxide layer of the first electrode 1110 may include any one of ITO, IZO, ITZO, SnO, ZnO, ICO and AZO, and the second electrode 1130 may include Al, Mg, Ca, Ag, alloy thereof (ex., Mg—Ag) or combination thereof.

The emissive layer 1120 is disposed on the first electrode 1110. The emissive layer 1120 includes at least two emitting parts emitting different colors. Each of the emitting part may have a single-layered structure of an EML. Alternatively, each of the emitting parts may include at least one of a HIL, a HTL, and an EBL, a HBL, an ETL and an EIL. In addition, the emissive layer 1120 may further comprise a CGL disposed between the emitting parts.

At least one of the at least two emitting parts may comprise a first compound of a host having the structure of Chemical Formulae 1 to 9, a second compound of delayed fluorescent material and/or a third compound of fluorescent or phosphorescent material.

A bank layer 1060 is disposed on passivation layer 1050 in order to cover edges of the first electrode 1110. The bank layer 1060 corresponds to each of the first to third pixel regions P1, P2 and P3 and exposes a center of the first electrode 1110. As described above, since the OLED D emits white light in the first to third pixel regions P1, P2 and P3, the emissive layer 1120 may be formed as a common layer without being separated in the first to third pixel regions P1, P2 and P3. The bank layer 1060 is formed to prevent current leakage from the edges of the first electrode 1110, and the bank layer 1060 may be omitted.

Moreover, the organic light emitting display device 1000 may further comprise an encapsulation film disposed on the second electrode 1130 in order to prevent outer moisture from penetrating into the OLED D. In addition, the organic light emitting display device 1000 may further comprise a polarizer disposed under the substrate 1010 in order to decrease external light reflection.

In the organic light emitting display device 1000 in FIG. 14, the first electrode 1110 is a transmissive electrode, the second electrode 1130 is a reflective electrode, and the color filter layer 1020 is disposed between the substrate 1010 and the OLED D. That is, the organic light emitting display device 1000 is a bottom-emission type. Alternatively, the first electrode 1110 may be a reflective electrode, the second electrode 1120 may be a transmissive electrode (or semi-transmissive electrode) and the color filter layer 1020 may be disposed over the OLED D in the organic light emitting display device 1000.

In the organic light emitting display device 1000, the OLED D located in the first to third pixel regions P1, P2 and P3 emits white light, and the white light passes through each of the first to third pixel regions P1, P2 and P3 so that each of a blue color, a green color and a red color is displayed in the first to third pixel regions P1, P2 and P3, respectively.

A color conversion film may be disposed between the OLED D and the color filter layer 1020. The color conversion film corresponds to the first to third pixel regions P1, P2 and P3, and comprises a blue color conversion film, a green color conversion film and a red color conversion film each of which can convert the white light emitted from the OLED D into blue light, green light and red light, respectively. For example, the color conversion film may comprise quantum dots. Accordingly, the organic light emitting display device 1000 may further enhance its color purity. Alternatively, the color conversion film may displace the color filter layer 1020.

Figure 15:
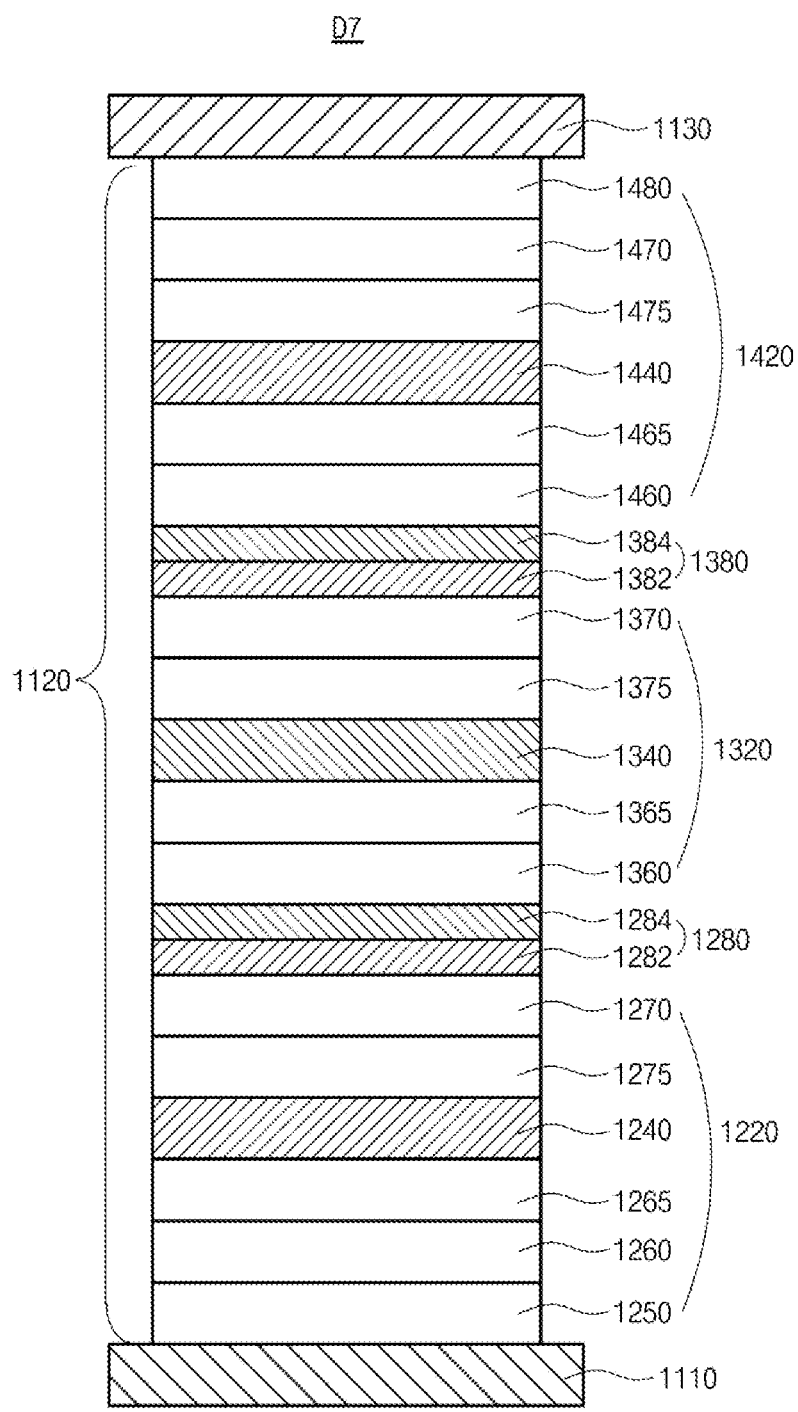
FIG. 15 is a schematic cross-sectional view illustrating an OLED in accordance with still another exemplary aspect of the present disclosure.

FIG. 15 is a schematic cross-sectional view illustrating an OLED in accordance with still another exemplary aspect of the present disclosure. As illustrated in FIG. 15, the OLED D7 comprises first and second electrodes 1110 and 1120 facing each other and an emissive layer 1120 disposed between the first and second electrodes 1110 and 1120. The first electrode 1110 may be an anode and the second electrode 1120 may be a cathode. For example, the first electrode 1100 may be a transmissive electrode and the second electrode 1120 may be a reflective electrode.

The emissive layer 1120 includes a first emitting part 1220 comprising a first EML (EML1) 1240, a second emitting part 1320 comprising a second EML (EML2) 1340 and a third emitting part 1420 comprising a third EML (EML3) 1440. In addition, the emissive layer 1120 may further comprise a first charge generation layer (CGL1) 1280 disposed between the first emitting part 1220 and the second emitting part 1320 and a second charge generation layer (CGL2) 1380 disposed between the second emitting part 1320 and the third emitting part 1420. Accordingly, the first emitting part 1220, the CGL1 1280, the second emitting part 1320, the CGL2 1380 and the third emitting part 1420 are disposed sequentially on the first electrode 1110.

The first emitting part 1220 may further comprise at least one of a first HTL (HTL1) 1260 disposed between the first electrode 1110 and the EML1 1240, a HIL 1250 disposed between the first electrode 1110 and the HTL1 1260 and a first ETL (ETL1) 1270 disposed between the EML1 1240 and the CGL1 1280. Alternatively, the first emitting part 1220 may further comprise a first EBL (EBL1) 1265 disposed between the HTL1 1260 and the EML1 1240 and/or a first HBL (HBL1) 1275 disposed between the EML1 1240 and the ETL1 1270.

The second emitting part 1320 may further comprise at least one of a second HTL (HTL2) 1360 disposed between the CGL1 1280 and the EML2 1340, a second ETL (ETL2) 1370 disposed between the EML2 1340 and the CGL2 1380. Alternatively, the second emitting part 1320 may further comprise a second EBL (EBL2) 1365 disposed between the HTL2 1360 and the EML2 1340 and/or a second HBL (HBL2) 1375 disposed between the EML2 1340 and the ETL2 1370.

The third emitting part 1420 may further comprise at least one of a third HTL (HTL3) 1460 disposed between the CGL2 1380 and the EML3 1440, a third ETL (ETL3) 1470 disposed between the EML3 1440 and the second electrode 1130 and an EIL 1480 disposed between the ETL3 1470 and the second electrode 1130. Alternatively, the third emitting part 1420 may further comprise a third EBL (EBL3) 1465 disposed between the HTL3 1460 and the EML3 1440 and/or a third HBL (HBL3) 1475 disposed between the EML3 1440 and the ETL3 1470.

The CGL1 1280 is disposed between the first emitting part 1220 and the second emitting part 1320. That is, the first emitting part 1220 and the second emitting part 1320 are connected via the CGL1 1280. The CGL1 1280 may be a PN-junction CGL that junctions a first N-type CGL (N-CGL1) 1282 with a first P-type CGL (P-CGL1) 1284.

The N-CGL1 1282 is disposed between the ETL1 1270 and the HTL2 1360 and the P-CGL1 1284 is disposed between the N-CGL1 1282 and the HTL2 1360. The N-CGL1 1282 transports electrons to the EML1 1240 of the first emitting part 1220 and the P-CGL1 1284 transport holes to the EML2 1340 of the second emitting part 1320.

The CGL2 1380 is disposed between the second emitting part 1320 and the third emitting part 1420. That is, the second emitting part 1320 and the third emitting part 1420 are connected via the CGL2 1380. The CGL2 1380 may be a PN-junction CGL that junctions a second N-type CGL (N-CGL2) 1382 with a second P-type CGL (P-CGL2) 1384.

The N-CGL2 1382 is disposed between the ETL2 1370 and the HTL3 1460 and the P-CGL2 1384 is disposed between the N-CGL2 1382 and the HTL3 1460. The N-CGL2 1382 transports electrons to the EML2 1340 of the second emitting part 1320 and the P-CGL2 1384 transport holes to the EML3 1440 of the third emitting part 1420. In one exemplary aspect, at least one of the N-CGL1 1282 and the N-CGL2 1382 may comprise the organic compound having the structure of Chemical Formulae 1 to 9.

In this aspect, one of the first to third EMLs 1240, 1340 and 1440 may be a blue EML, another of the first to third EMLs 1240, 1340 and 1440 may be a green EML and the third of the first to third EMLs 1240, 1340 and 1440 may be a red EML.

As an example, the EML1 1240 may be a blue EML, the EML2 1340 may be a green EML and the EML3 1440 may be a red EML. Alternatively, the EML1 1240 may be a red EML, the EML2 1340 may be a green EML and the EML3 1440 may be a blue EML1. Hereinafter, we will describe the OLED D7 where the EML1 1240 is the blue EML, the EML2 1340 is the green EML and the EML3 1440 is the red EML.

As described below, at least one of the EML1 1240, the EML2 1340 and the EML3 1440 may comprise the first compound, the second compound and/or the third compound. The EMLs 1240, 1340 and 1440 including the first compound, the second compound and/or the third compound may have a single-layered structure, a double-layered structure or a triple-layered structure.

The EML1 1240 may comprise the first compound of a host having the structure of Chemical Formulae 1 to 9, the second compound of blue delayed fluorescent material and/or the third compound of blue fluorescent or phosphorescent material. Alternatively, the EML1 1240 may comprise the host and other blue dopant. The host may comprise the first compound and other blue dopant may comprise at least one of blue phosphorescent material, blue fluorescent material and blue delayed fluorescent material.

The EML2 1340 may comprise the first compound of a host having the structure of Chemical Formulae 1 to 9, the second compound of green delayed fluorescent material and/or the third compound of green fluorescent or phosphorescent material. Alternatively, the EML2 1340 may comprise the host and other green dopant. The host may comprise the first compound and other green dopant may comprise at least one of green phosphorescent material, green fluorescent material and green delayed fluorescent material.

The EML3 1440 may comprise the first compound of a host having the structure of Chemical Formulae 1 to 9, the second compound of red delayed fluorescent material and/or the third compound of red fluorescent or phosphorescent material. Alternatively, the EML1 1240 may comprise the host and other red dopant. The host may comprise the first compound and other red dopant may comprise at least one of red phosphorescent material, red fluorescent material and red delayed fluorescent material.

For example, each of the EML1 1240, the EML2 1340 and the EML3 1440 includes the first compound, the second compound and the third compound, the contents of the first compound may be larger than the contents of the second compound, and the contents of the second compound is larger than the contents of the third compound. In this case, exciton energy can be transferred efficiently from the second compound to the third compound. As an example, each of the contents of the first to third compounds in each of the EML1 1240, the EML2 1340 and the EML3 1440 may be, but is not limited to, about 60 wt % to about 75 wt %, about 20 wt % to about 40 wt % and about 0.1 wt % to about 5 wt %, respectively.

The OLED D7 emits white light in each of the first to third pixel regions P1, P2 and P3 and the white light passes though the color filter layer 1020 (FIG. 14) correspondingly disposed in the first to third pixel regions P1, P2 and P3. Accordingly, the OLED D7 can implement a full-color image.

Figure 16:
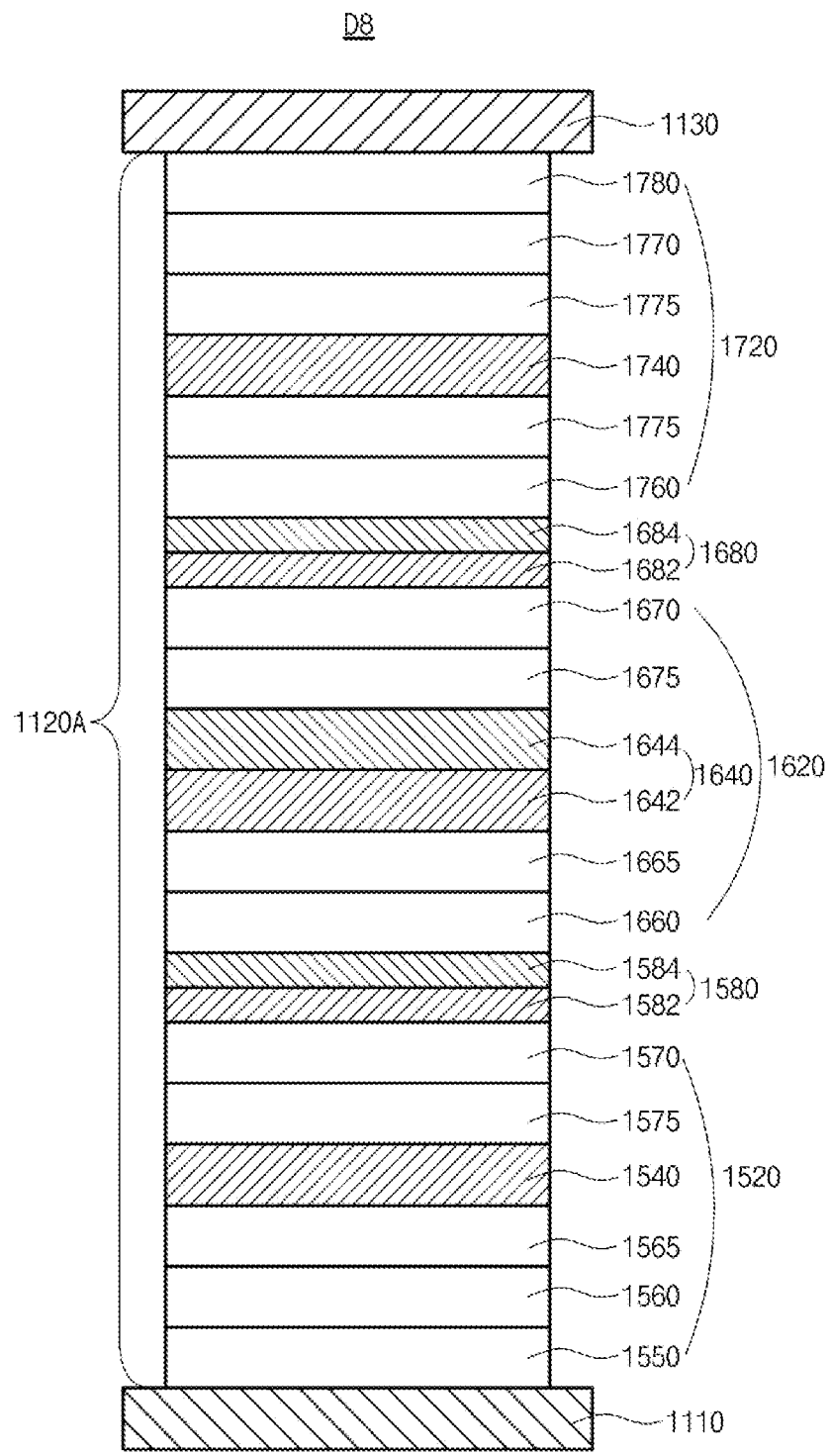
FIG. 16 is a schematic cross-sectional view illustrating an OLED in accordance with still another exemplary aspect of the present disclosure.

FIG. 16 is a schematic cross-sectional view illustrating an OLED in accordance with still another exemplary aspect of the present disclosure. As illustrated in FIG. 16, the OLED D8 comprises first and second electrodes 1110 and 1120 facing each other and an emissive layer 1120A disposed between the first and second electrodes 1110 and 1120. The first electrode 1110 may be an anode and the second electrode 1120 may be a cathode. For example, the first electrode 1100 may be a transmissive electrode and the second electrode 1120 may be a reflective electrode.

The emissive layer 1120A includes a first emitting part 1520 comprising an EML1 1540, a second emitting part 1620 comprising an EML2 1640 and a third emitting part 1720 comprising a EML3 1740. In addition, the emissive layer 1120A may further comprise a CGL1 1580 disposed between the first emitting part 1520 and the second emitting part 1620 and a CGL2 1680 disposed between the second emitting part 1620 and the third emitting part 1720. Accordingly, the first emitting part 1520, the CGL1 1580, the second emitting part 1620, the CGL2 1680 and the third emitting part 1720 are disposed sequentially on the first electrode 1110.

The first emitting part 1520 may further comprise at least one of a HTL1 1560 disposed between the first electrode 1110 and the EML1 1540, a HIL 1550 disposed between the first electrode 1110 and the HTL1 1560 and an ETL1 1570 disposed between the EML1 1540 and the CGL1 1580. Alternatively, the first emitting part 1520 may further comprise an EBL1 1565 disposed between the HTL1 1560 and the EML1 1540 and/or a HBL1 1575 disposed between the EML1 1540 and the ETL1 1570.

The EML2 1640 of the second emitting part 1620 comprises a lower EML 1642 and an upper EML 1644. The lower EML 1642 is located adjacently to the first electrode 1110 and the upper EML 1644 is located adjacently to the second electrode 1130. In addition, the second emitting part 1620 may further comprise at least one of a HTL2 1660 disposed between the CGL1 1580 and the EML2 1640, an ETL2 1670 disposed between the EML2 1640 and the CGL2 1680. Alternatively, the second emitting part 1620 may further comprise an EBL2 1665 disposed between the HTL2 1660 and the EML2 1640 and/or a HBL2 1675 disposed between the EML2 1640 and the ETL2 1670.

The third emitting part 1720 may further comprise at least one of a HTL3 1760 disposed between the CGL2 1680 and the EML3 1740, an ETL3 1770 disposed between the EML3 1740 and the second electrode 1130 and an EIL 1780 disposed between the ETL3 1770 and the second electrode 1130. Alternatively, the third emitting part 1720 may further comprise an EBL3 1765 disposed between the HTL3 1760 and the EML3 1740 and/or a HBL3 1775 disposed between the EML3 1740 and the ETL3 1770.

The CGL1 1380 is disposed between the first emitting part 1520 and the second emitting part 1620. That is, the first emitting part 1520 and the second emitting part 1620 are connected via the CGL1 1580. The CGL1 1580 may be a PN-junction CGL that junctions an N-CGL1 1582 with a P-CGL1 1584. The N-CGL1 1582 is disposed between the ETL1 1570 and the HTL2 1660 and the P-CGL1 1584 is disposed between the N-CGL1 1582 and the HTL2 1560.

The CGL2 1680 is disposed between the second emitting part 1620 and the third emitting part 1720. That is, the second emitting part 1620 and the third emitting part 1720 are connected via the CGL2 1680. The CGL2 1680 may be a PN-junction CGL that junctions an N-CGL2 1682 with a P-CGL2 1684. The N-CGL2 1682 is disposed between the ETL2 1570 and the HTL3 1760 and the P-CGL2 1684 is disposed between the N-CGL2 1682 and the HTL3 1760. In one exemplary aspect, at least one of the N-CGL1 1582 and the N-CGL2 1682 may include any organic compound having the structure of Chemical Formulae 1 to 9.

As described below, at least one of the EML1 1540, the EML2 1640 and the EML3 1740 may comprise the first compound, the second compound and/or the third compound. The EMLs 1540, 1640 and 1740 including the first compound, the second compound and/or the third compound may have a single-layered structure, a double-layered structure or a triple-layered structure.

In this aspect, each of the EML1 1540 and the EML3 1740 may be a blue EML. In one exemplary aspect, each of the EML1 1540 and the EML3 1740 may comprise the first compound of a host, the second compound of blue delayed fluorescent material and/or the third compound of blue fluorescent or phosphorescent material. Alternatively, at least one of the EML1 1540 and the EML3 1740 may comprise a host and other blue dopant. The host may comprise the first compound and other blue dopant may comprise blue phosphorescent material, blue fluorescent material and blue delayed fluorescent material.

Each of the first to third compounds in the EML1 1540 may be identical to or different from each of the first to third compounds in the EML3 1740. For example, the blue dopant in the EML1 1540 may be different from the blue dopant in the EML3 1740 in terms of luminous efficiency and/or emission wavelength.

One of the lower EML 1642 and the upper EML 1644 in the EML2 1640 may be a green EML and the other of the lower EML 1642 and the upper EML 1644 in the EML2 1640 may be a red EML. The green EML and the red EML is sequentially disposed to form the EML2 1640.

In one exemplary aspect, the lower EML 1642 of the green EML may comprise a first compound of a host, and a second compound of green delayed fluorescent material and/or a third compound of green fluorescent or phosphorescent material. Alternatively, the lower EML 1642 of the green EML may comprise a host and other green dopant. The host may comprise the first compound and the green dopant may comprise at least one of green phosphorescent material, green fluorescent material and green delayed fluorescent material.

The upper EML 1644 of the red EML may comprise a first compound of a host, and a second compound of red delayed fluorescent material and/or a third compound of red fluorescent or phosphorescent material. Alternatively, the lower EML 1642 of the red EML may comprise a host and other red dopant. The host may comprise the first compound and the red dopant may comprise at least one of red phosphorescent material, red fluorescent material and red delayed fluorescent material.

For example, each of the EML1 1540, the EML2 1640 and the EML3 1740 includes the first compound, the second compound and the third compound, the contents of the first compound may be larger than the contents of the second compound, and the contents of the second compound is larger than the contents of the third compound. In this case, exciton energy can be transferred efficiently from the second compound to the third compound. As an example, each of the contents of the first to third compounds in each of the EML1 1240, the EML2 1340 and the EML3 1440 may be, but is not limited to, about 60 wt % to about 75 wt %, about 20 wt % to about 40 wt % and about 0.1 wt % to about 5 wt %, respectively.

The OLED D8 emits white light in each of the first to third pixel regions P1, P2 and P3 and the white light passes though the color filter layer 1020 (FIG. 14) correspondingly disposed in the first to third pixel regions P1, P2 and P3. Accordingly, the organic light emitting display device 1000 (FIG. 13) can implement a full-color image.

In FIG. 16, the OLED D8 has a three-stack structure including the first to three emitting parts 1520, 1620 and 1720 which includes the EML1 1540 and the EML3 1740 as a blue EML. Alternatively, the OLED D8 may have a two-stack structure where one of the first emitting part 1520 and the third emitting part 1720 each of which includes the EML1 1540 and the EML3 1740 as a blue EML is omitted.

Synthesis Example 1: Synthesis of Compound 1-1

(1) Synthesis of Intermediate A

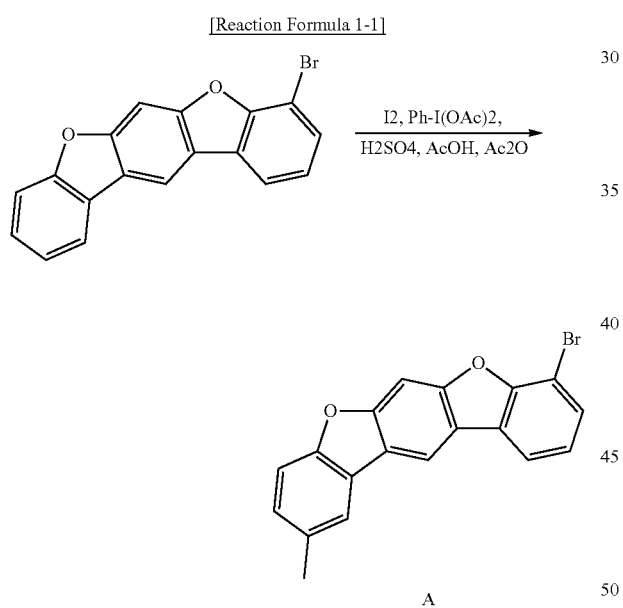

4-bromobenzo[1,2-b:5,4-b']bisbenzofuran (10 g, 40.65 mmol), iodine (5.1 g, 20.32 mmol) and phenyl iodide diacetate (6.6 g, 20.32 mmol) were dissolved in a mixed solvent of acetic acid (150 mL) and acetic anhydride (150 mL) under nitrogen atmosphere, three drops of sulfuric acid was added into the solution, and then the solution was stirred at room temperature for 10 hours. After the reaction was complete, ethyl acetate was added into the mixed solution, and then the mixed solution was washed with water to separate an organic layer. Anhydrous magnesium sulfate was added into the organic layer and the organic layer was stirred, was filtered with a silica pad and then concentrated under reduced pressure. The obtained crude product was purified with a column chromatography to give an intermediate A (yield: 75%).

(2) Synthesis of Intermediate B

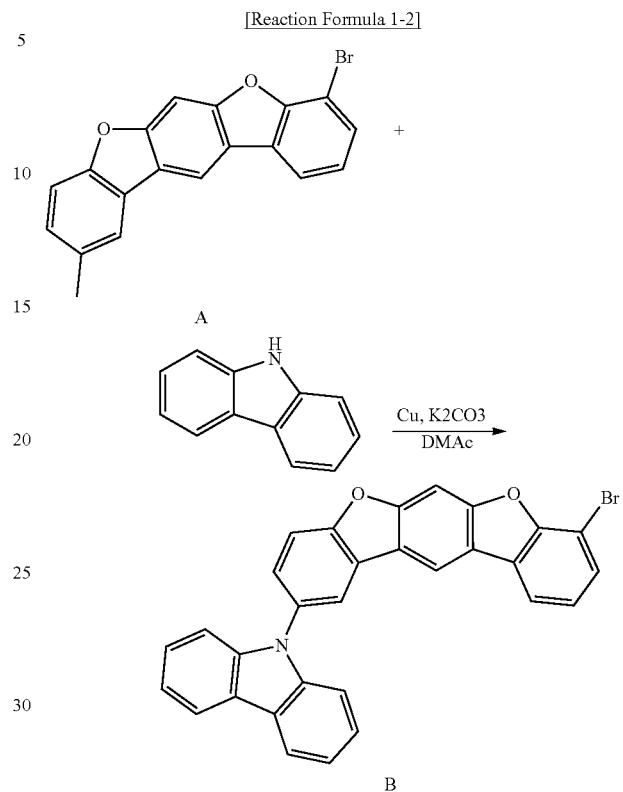

The intermediate A (8.4 g, 20.43 mmol), carbazole (2.2 g, 13.18 mmol), copper powder (2 g, 32.53 mmol) and potassium carbonate (3.6 g, 26.35 mmol) were dissolved in dimethylacetamide (DMAc, 70 mL), and then the solution was stirred at 130° C. for 24 hours. After the reaction was complete, the solution was cooled down to room temperature and filtered with a silica pad to remove the copper powder. Obtained solution was washed with water to separate an organic layer, anhydrous magnesium sulfate was added into the organic layer, and then the organic layer was stirred, filtered with a silica pad and concentrated under reduced pressure. The obtained crude product was purified with a column chromatography to give an intermediate B (yield: 64%).

(3) Synthesis of Compound 1-1

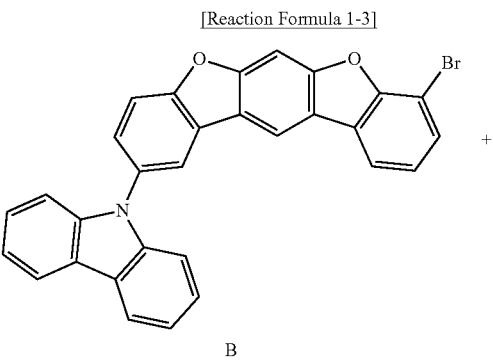

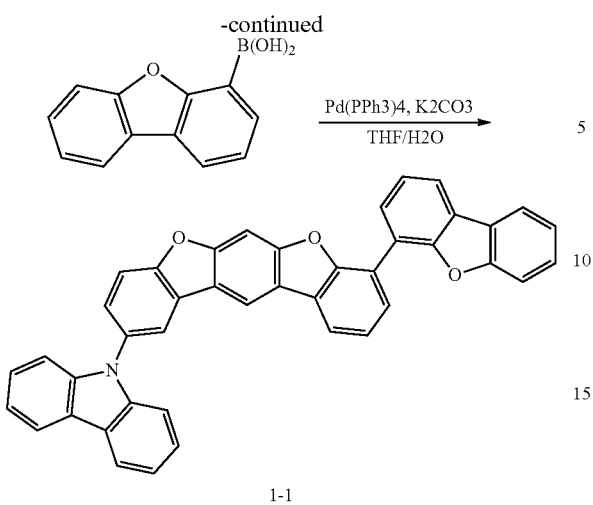

1-1

The intermediate B (8.4 g, 20.43 mmol), dibenzo[b,d]furan-4-ylboronic acid (4.76 g, 22.47 mmol) and tetrakis(triphenylphosphine)palladium(0) (Pd(PPh$_3$)$_4$, 2 mol %) were dissolved in tetrahydrofuran (THF, 50 mL), potassium carbonate (40.86 mmol) was dissolved in water (25 mL), and then two solutions were mixed. The solution was stirred at 80° C. for 12 hours to terminate the reaction. The solution was cooled down to room temperature to separate water from an organic layer. Anhydrous magnesium sulfate was added into the organic layer and the organic layer was stirred, filtered with a silica pad and then concentrated under reduced pressure. The obtained crude product was purified with a column chromatography to give a compound 1-1 (yield: 54%).

Synthesis Example 2: Synthesis of Compound 2-1

(1) Synthesis of Intermediate C

[Reaction Formula 2-1]

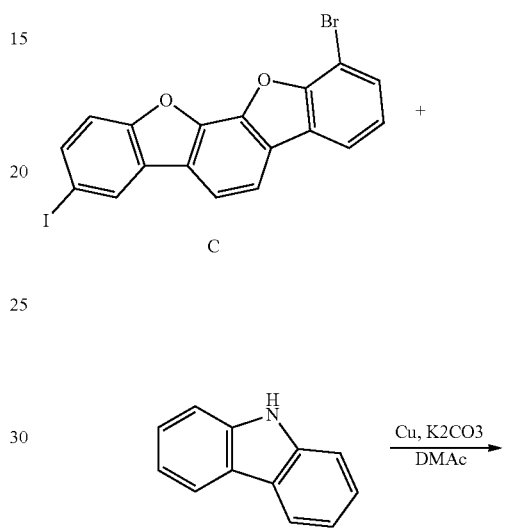

C 4-bromobenzo[2,1-b:3,4-b']bisbenzofuran (10 g, 40.65 mmol), iodine (5.1 g, 20.32 mmol) and phenyl iodide diacetate (6.6 g, 20.32 mmol) were dissolved in a mixed solvent of acetic acid (150 mL) and acetic anhydride (150 mL) under nitrogen atmosphere, three drops of sulfuric acid was added into the solution, and then the solution was stirred at room temperature for 10 hours. After the reaction was complete, ethyl acetate was added into the mixed solution, and then the mixed solution was washed with water to separate an organic layer. Anhydrous magnesium sulfate was added into the organic layer and the organic layer was stirred, was filtered with a silica pad and then concentrated under reduced pressure. The obtained crude product was purified with a column chromatography to give an intermediate C (yield: 70%).

(2) Synthesis of Intermediate D

[Reaction Formula 2-2]

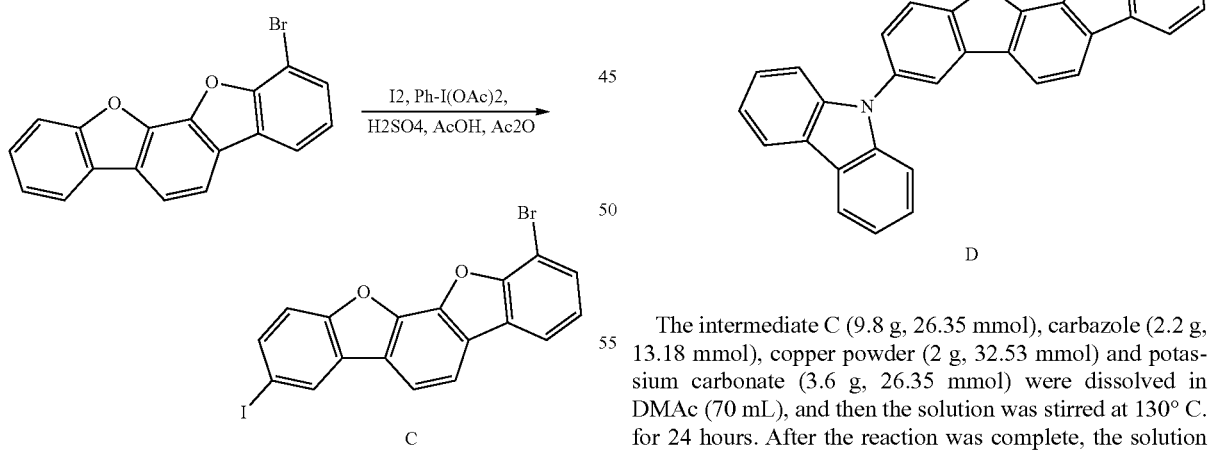

D

The intermediate C (9.8 g, 26.35 mmol), carbazole (2.2 g, 13.18 mmol), copper powder (2 g, 32.53 mmol) and potassium carbonate (3.6 g, 26.35 mmol) were dissolved in DMAc (70 mL), and then the solution was stirred at 130° C. for 24 hours. After the reaction was complete, the solution was cooled down to room temperature and filtered with a silica pad to remove the copper powder. Obtained solution was washed with water to separate an organic layer, anhydrous magnesium sulfate was added into the organic layer, and then the organic layer was stirred, filtered with a silica pad and concentrated under reduced pressure. The obtained crude product was purified with a column chromatography to give an intermediate D (yield: 60%).

(3) Synthesis of Compound 2-1

[Reaction Formula 2-3]

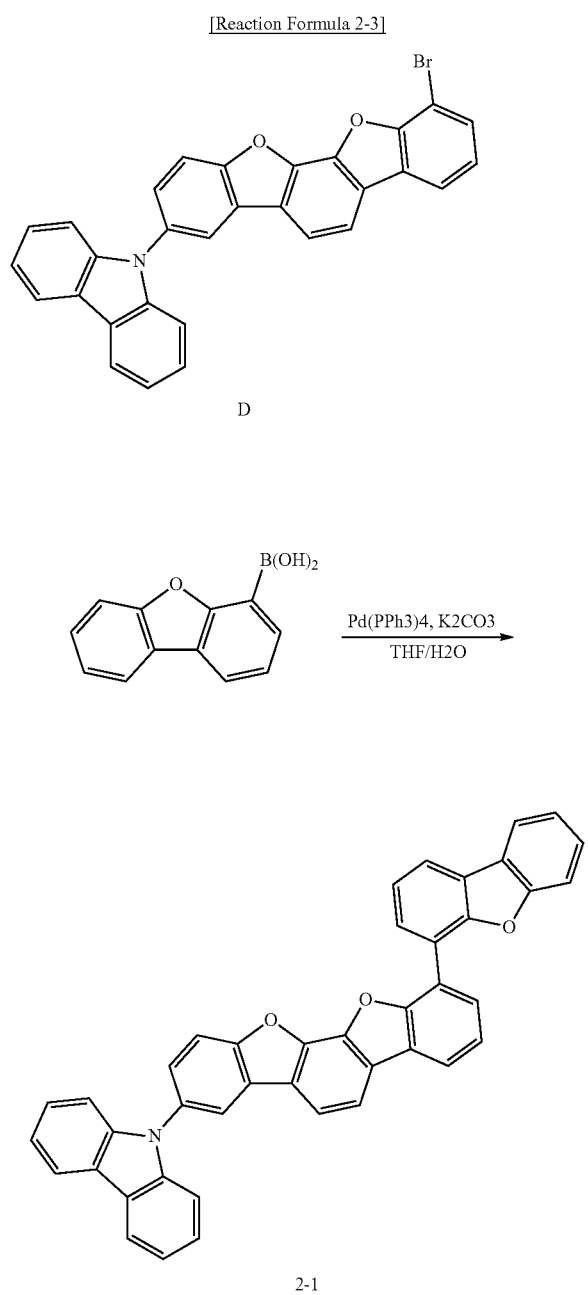

2-1

The intermediate D (8.4 g, 20.43 mmol), dibenzo[b,d]furan-4-ylboronic acid (4.76 g, 22.47 mmol) and Pd(PPh$_3$)$_4$ (2 mol %) were dissolved in THF (50 mL), potassium carbonate (40.86 mmol) was dissolved in water (25 mL), and then two solutions were mixed. The solution was stirred at 80° C. for 12 hours to terminate the reaction. The solution was cooled down to room temperature to separate water from an organic layer. Anhydrous magnesium sulfate was added into the organic layer and the organic layer was stirred, filtered with a silica pad and then concentrated under reduced pressure. The obtained crude product was purified with a column chromatography to give a compound 2-1 (yield: 48%).

Synthesis Example 3: Synthesis of Compound 3-1

(1) Synthesis of Intermediate E

[Reaction Formula 3-1]

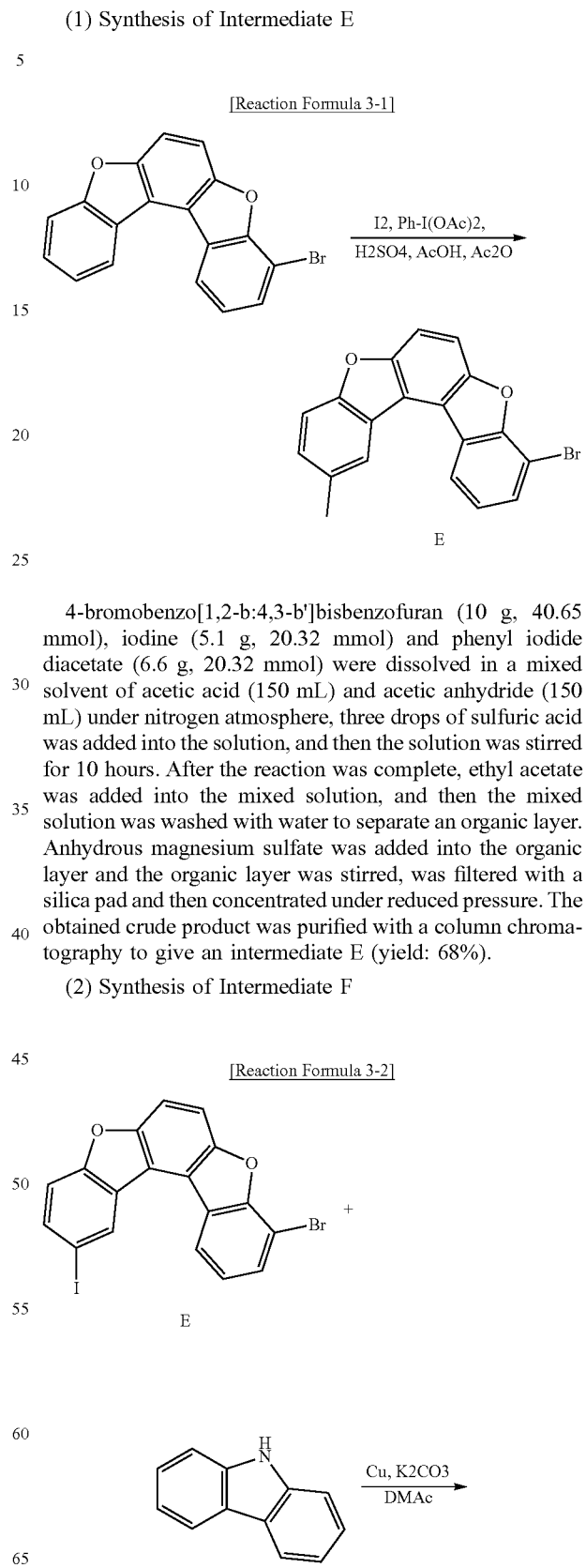

E 4-bromobenzo[1,2-b:4,3-b']bisbenzofuran (10 g, 40.65 mmol), iodine (5.1 g, 20.32 mmol) and phenyl iodide diacetate (6.6 g, 20.32 mmol) were dissolved in a mixed solvent of acetic acid (150 mL) and acetic anhydride (150 mL) under nitrogen atmosphere, three drops of sulfuric acid was added into the solution, and then the solution was stirred for 10 hours. After the reaction was complete, ethyl acetate was added into the mixed solution, and then the mixed solution was washed with water to separate an organic layer. Anhydrous magnesium sulfate was added into the organic layer and the organic layer was stirred, was filtered with a silica pad and then concentrated under reduced pressure. The obtained crude product was purified with a column chromatography to give an intermediate E (yield: 68%).

(2) Synthesis of Intermediate F

[Reaction Formula 3-2]

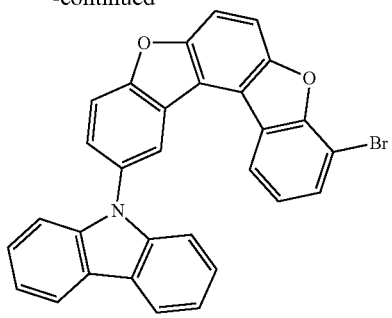

F

The intermediate E (9.8 g, 26.35 mmol), carbazole (2.2 g, 13.18 mmol), copper powder (2 g, 32.53 mmol) and potassium carbonate (3.6 g, 26.35 mmol) were dissolved in DMAc (70 mL), and then the solution was stirred at 130° C. for 24 hours. After the reaction was complete, the solution was cooled down to room temperature and filtered with a silica pad to remove the copper powder. Obtained solution was washed with water to separate an organic layer, anhydrous magnesium sulfate was added into the organic layer, and then the organic layer was stirred, filtered with a silica pad and concentrated under reduced pressure. The obtained crude product was purified with a column chromatography to give an intermediate F (yield: 58%).

(3) Synthesis of Compound 3-1

[Reaction Formula 3-3]

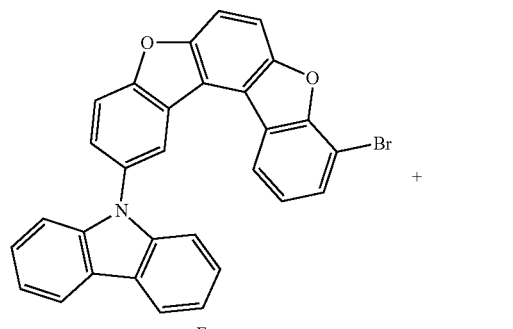

3-1

The intermediate F (8.4 g, 20.43 mmol), dibenzo[b,d]furan-4-ylboronic acid (4.76 g, 22.47 mmol) and Pd(PPh$_3$)$_4$ (2 mol %) were dissolved in THF (50 mL), potassium carbonate (40.86 mmol) was dissolved in water (25 mL), and then two solutions were mixed. The solution was stirred at 80° C. for 12 hours to terminate the reaction. The solution was cooled down to room temperature to separate water from an organic layer. Anhydrous magnesium sulfate was added into the organic layer and the organic layer was stirred, filtered with a silica pad and then concentrated under reduced pressure. The obtained crude product was purified with a column chromatography to give a compound 3-1 (yield: 41%).

Synthesis Example 4: Synthesis of Compound 4-1

(1) Synthesis of Intermediate G

[Reaction Formula 4-1]

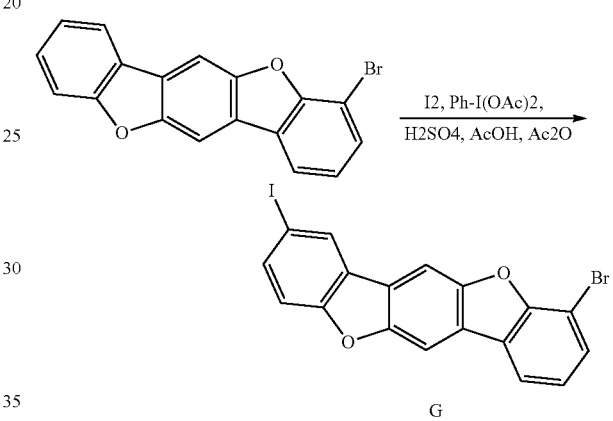

G 4-bromobenzo[2,3-b:2',3-3']bisbenzofuran (10 g, 40.65 mmol), iodine (5.1 g, 20.32 mmol) and phenyl iodide diacetate (6.6 g, 20.32 mmol) were dissolved in a mixed solvent of acetic acid (150 mL) and acetic anhydride (150 mL) under nitrogen atmosphere, three drops of sulfuric acid was added into the solution, and then the solution was stirred for 10 hours. After the reaction was complete, ethyl acetate was added into the mixed solution, and then the mixed solution was washed with water to separate an organic layer. Anhydrous magnesium sulfate was added into the organic layer and the organic layer was stirred, was filtered with a silica pad and then concentrated under reduced pressure. The obtained crude product was purified with a column chromatography to give an intermediate G (yield: 80%).

(2) Synthesis of Intermediate H

[Reaction Formula 4-2]

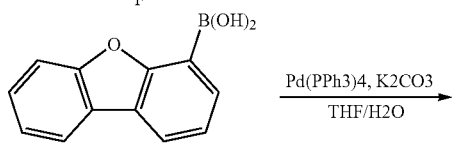

G

-continued

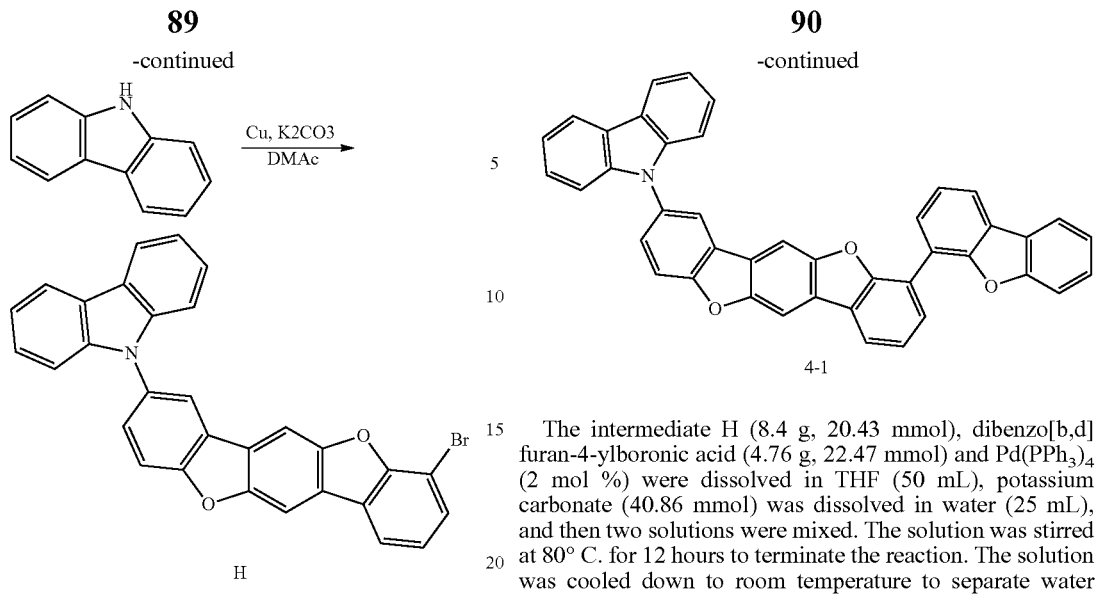

The intermediate G (9.8 g, 26.35 mmol), carbazole (2.2 g, 13.18 mmol), copper powder (2 g, 32.53 mmol) and potassium carbonate (3.6 g, 26.35 mmol) were dissolved in DMAc (70 mL), and then the solution was stirred at 130° C. for 24 hours. After the reaction was complete, the solution was cooled down to room temperature and filtered with a silica pad to remove the copper powder. Obtained solution was washed with water to separate an organic layer, anhydrous magnesium sulfate was added into the organic layer, and then the organic layer was stirred, filtered with a silica pad and concentrated under reduced pressure. The obtained crude product was purified with a column chromatography to give an intermediate H (yield: 65%).

(3) Synthesis of Compound 4-1

[Reaction Formula 4-3]

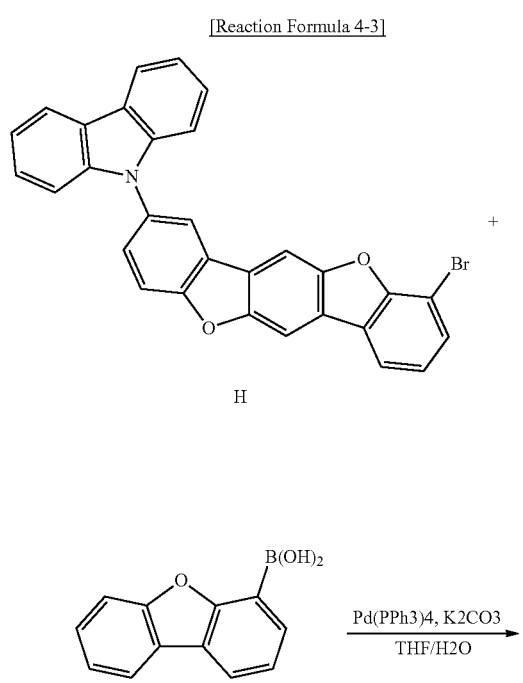

-continued

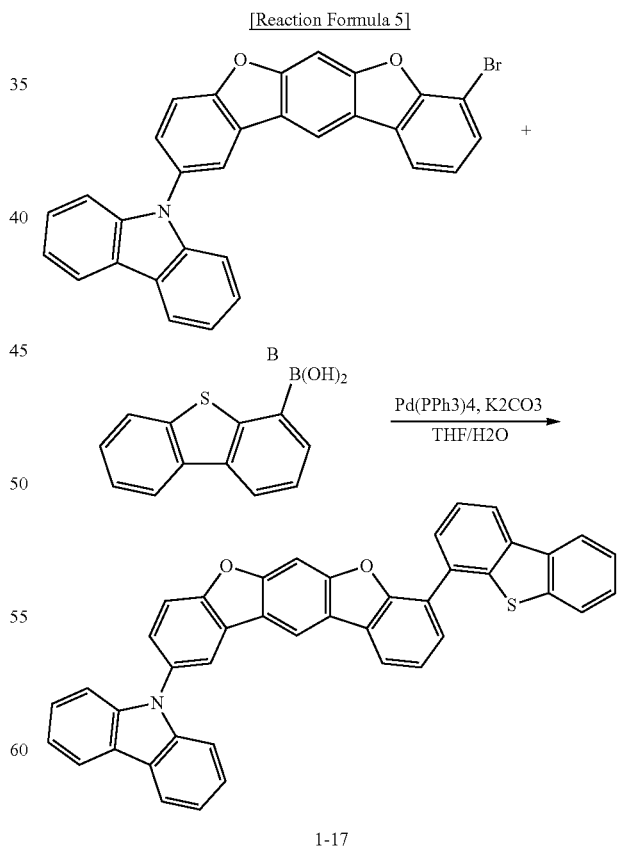

4-1

The intermediate H (8.4 g, 20.43 mmol), dibenzo[b,d]furan-4-ylboronic acid (4.76 g, 22.47 mmol) and Pd(PPh$_3$)$_4$ (2 mol %) were dissolved in THF (50 mL), potassium carbonate (40.86 mmol) was dissolved in water (25 mL), and then two solutions were mixed. The solution was stirred at 80° C. for 12 hours to terminate the reaction. The solution was cooled down to room temperature to separate water from an organic layer. Anhydrous magnesium sulfate was added into the organic layer and the organic layer was stirred, filtered with a silica pad and then concentrated under reduced pressure. The obtained crude product was purified with a column chromatography to give a compound 4-1 (yield: 50%).

Synthesis Example: Synthesis of Compound 1-17

[Reaction Formula 5]

The intermediate B (8.4 g, 20.43 mmol), dibenzo[b,d]thiophen-4-ylboronic acid (5.12 g, 22.47 mmol) and Pd(PPh$_3$)$_4$ (2 mol %) were dissolved in THF (50 mL), potassium carbonate (40.86 mmol) was dissolved in water (25 mL), and then two solutions were mixed. The solution was stirred at 80° C. for 12 hours to terminate the reaction. The solution was cooled down to room temperature to separate water from an organic layer. Anhydrous magnesium sulfate was added into the organic layer and the organic layer was stirred, filtered with a silica pad and then concentrated under reduced pressure. The obtained crude product was purified with a column chromatography to give a compound 1-17 (yield: 54%).

Experimental Example 1: Measurement of Energy Levels

Excited triplet energy level (T$_1$), HOMO energy level, LUMO energy level and HOMO-LUMO energy bandgap (E$_g$) of each of the compounds 1-1, 2-1, 3-1 and 4-1 were evaluated with simulation. For comparison, HOMO energy level, LUMO energy level and HOMO-LUMO energy bandgap (E$_g$) of mCBP which will be used as a host in the EML in comparative Example below, are provided. For the simulation measurement, Schrodinger's program (Optoelectronic Calculation) was used, and the results were evaluated by Approximation calculation and performed under Function_B3LYP<Base set_MIDIX condition. The following table 1 indicates the measurement results.

TABLE 1

Simulation of Energy Levels of Organic Compound

| Compound | T$_1$ (eV) | HOMO(eV) | LUMO(eV) | E$_g$ (eV) |
|---|---|---|---|---|
| mCBP | 2.81 | −5.84 | −2.33 | 3.51 |
| 1-1 | 2.81 | −5.82 | −2.67 | 3.15 |
| 2-1 | 2.89 | −5.83 | −2.66 | 3.17 |
| 3-1 | 2.91 | −5.82 | −2.43 | 3.39 |
| 4-1 | 2.79 | −5.83 | −2.44 | 3.39 |

As indicated in Table 1, each of compounds 1-1, 2-1, 3-1 and 4-1 showed T$_1$, HOMO and LUMO energy level proper for applying in an emissive layer. Particularly, all the compounds synthesized in the Synthesis Examples 1-4 showed very high T$_1$ and shallow LUMO energy level, thus they were proper for the host in an EML, an ETL and/or a HBL.

Example 1 (Ex. 1): Fabrication of OLED

An OLED in which the Compound 1-1 was applied into an EML as a host was fabricated. An ITO attached glass substrate was washed with ozone and was loaded into the vapor system, and then was transferred to a vacuum deposition chamber in order to deposit other layers on the substrate. An organic layer was deposited by evaporation by a heated boat under 10$^{-7}$ torr with setting a deposition rate to 1 Å/s in the following order.

An ITO (50 nm); a HIL (HAT-CN; 10 nm); a HTL (NPBC, 75 nm); an EBL (mCBP, 15 nm); an EML (Compound 1-1 (Host): delayed fluorescent material below (dopant)=60:40 by weight; 35 nm); a HBL (B3PYMPM, 10 nm); an ETL (TPBi; 20 nm); an EIL (LiF; 0.8 nm); and a cathode (Al; 100 nm).

And then, cappling layer (CPL) was deposited over the cathode and the device was encapsulated by glass. After deposition of emissive layer and the cathode, the OLED was transferred from the deposition chamber to a dry box for film formation, followed by encapsulation using UV-curable epoxy resin and moisture getter.

[Delayed Fluorescent Material]

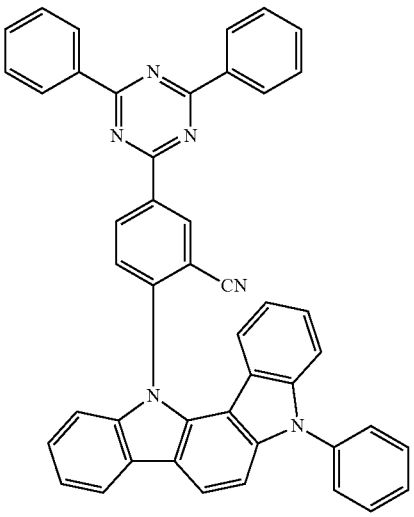

Examples 2-4 (Ex. 2-4): Fabrication of OLED

An OLED was fabricated using the same materials as Example 1, except that Compound 2-1 (Ex. 2), Compound 3-1 (Ex. 3) or Compound 4-1 (Ex. 4) was applied into the EML as the host instead of the Compound 1-1.

Comparative Example (Ref.): Fabrication of OLED

An OLED was fabricated using the same materials as Example 1, except that mCBP was applied into the EML as the host instead of the Compound 1-1.

Experimental Example 2: Measurement of Luminous Properties of OLED

Each of the OLED having luminous area of 9 mm$^2$ and fabricated by Ex. 1-4 and Ref was connected to an external power source and then luminous properties for all the diodes were evaluated using a constant current source (KEITHLEY) and a photometer PR650 at room temperature. In particular, driving voltage (V), current efficiency (cd/A), power efficiency (lm/W), external quantum efficiency (EQE, %), CIE color coordinate, maximum electroluminescence wavelength (EL $\lambda_{max}$, nm) and T$_{95}$ (period of 95% luminance from initial luminance, hour) at a current density of 10 mA/cm$^2$ were measured. The results thereof are shown in the following Table 2.

TABLE 2

Luminous Properties of OLED

| Sample | V | cd/A | lm/W | EQE | CIE(x, y) | $\lambda_{max}$ | T$_{95}$ |
|---|---|---|---|---|---|---|---|
| Ref. | 4.4 | 50.6 | 36.2 | 15.8 | (0.367, 0.567) | 538 | 125 |
| Ex. 1 | 3.8 | 50.7 | 46.5 | 17.2 | (0.377, 0.582) | 540 | 290 |
| Ex. 2 | 4.0 | 53.4 | 44.5 | 18.6 | (0.358, 0.612) | 536 | 235 |
| Ex. 3 | 4.0 | 54.6 | 45.0 | 18.9 | (0.381, 0.571) | 538 | 245 |
| Ex. 4 | 3.8 | 51.1 | 47.5 | 17.6 | (0.376, 0.584) | 540 | 271 |

As indicated in Table 2, compared to the OLED in Ref. in which conventional host mCBP was applied into the EML, the OLEDs in Ex. 1-3 reduced their driving voltages up to 13.6% and enhanced their current efficiency, power efficiency, EQE and luminous lifetime up to 7.9%, 31.2%, 19.6% and 132.0%, respectively.

It will be apparent to those skilled in the art that various modifications and variations can be made in the present disclosure without departing from the scope of the invention. Thus, it is intended that the present disclosure cover the modifications and variations of the present disclosure provided they come within the scope of the appended claims.

What is claimed is:

1. An organic compound having the following structure of Chemical Formula 1:

[Chemical Formula 1]

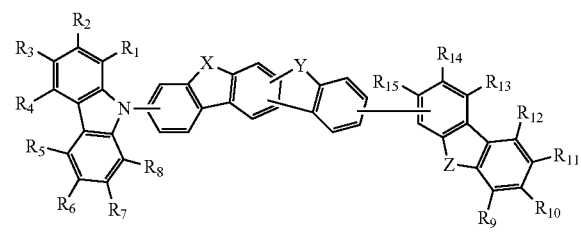

wherein each of $R_1$ to $R_{15}$ is independently selected from the group consisting of hydrogen, an unsubstituted or substituted silyl group, an unsubstituted or substituted $C_1$-$C_{20}$ alkyl group, an unsubstituted or substituted $C_1$-$C_{20}$ alkoxy group, an unsubstituted or substituted $C_1$-$C_{20}$ alkyl amino group, an unsubstituted or substituted $C_6$-$C_{30}$ aromatic group and an unsubstituted or substituted $C_3$-$C_{30}$ hetero aromatic group, or two adjacent groups among $R_1$ to $R_{15}$ form an unsubstituted or substituted $C_6$-$C_{20}$ aromatic ring or an unsubstituted or substituted $C_3$-$C_{20}$ hetero aromatic ring; each of X, Y and Z is independently oxygen (O) or sulfur (S).

2. The organic compound of claim 1, wherein the organic compound has the following structure of Chemical Formula 2:

[Chemical Formula 2]

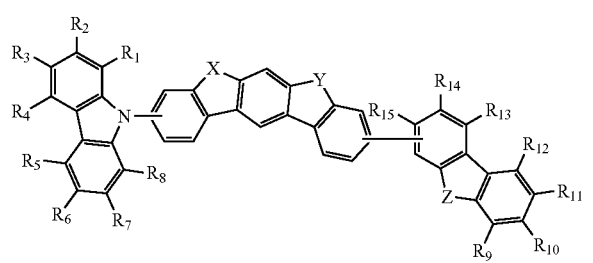

wherein each of $R_1$ to $R_{15}$, X, Y and Z is identical as defined in Chemical Formula 1.

3. The organic compound of claim 2, wherein the organic compound is selected from:

1-1

1-2

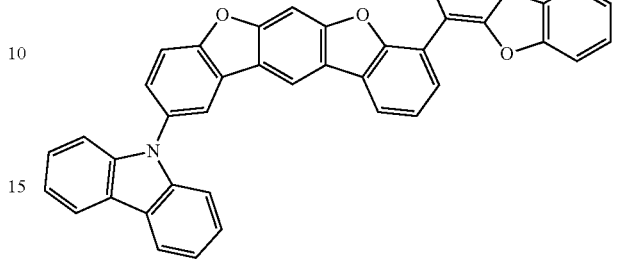

1-3

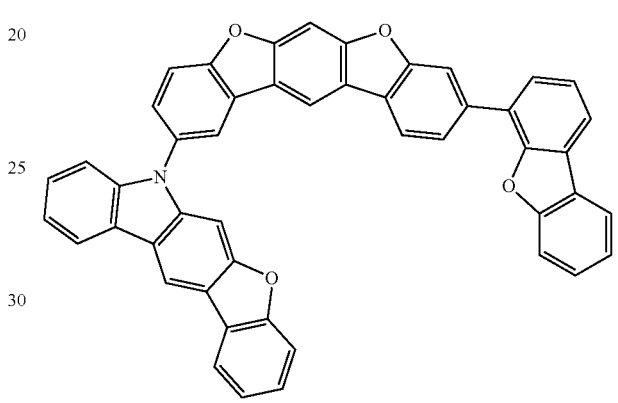

1-4

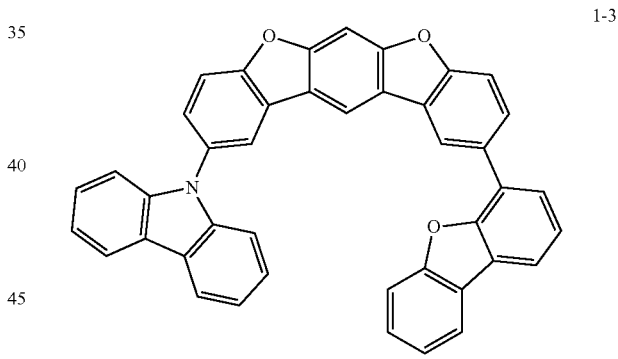

95
-continued
1-5
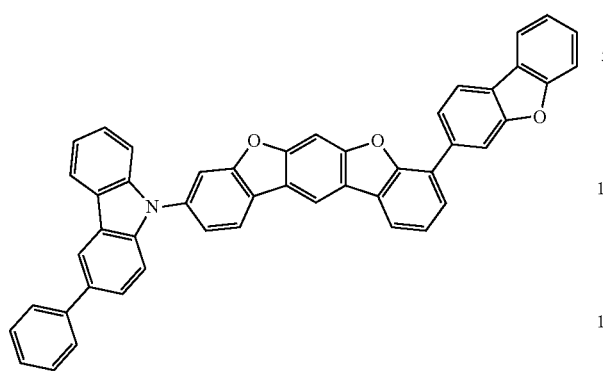
1-6
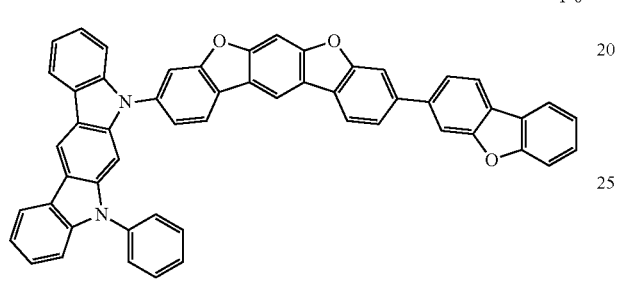
1-7
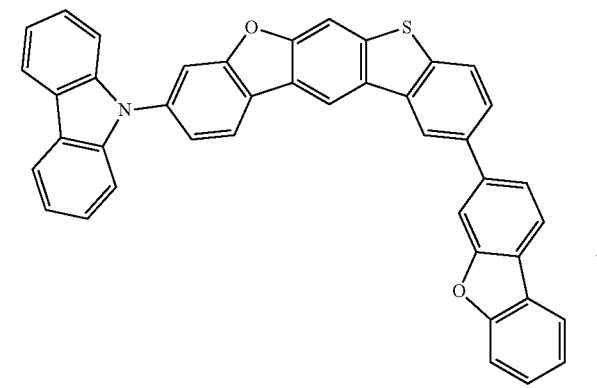
1-8
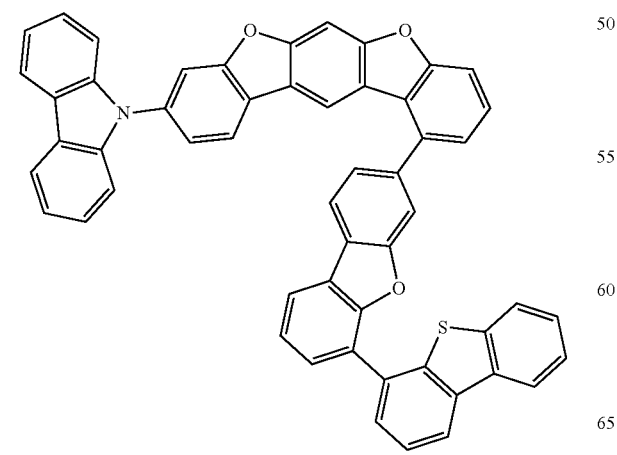
96
-continued
1-9
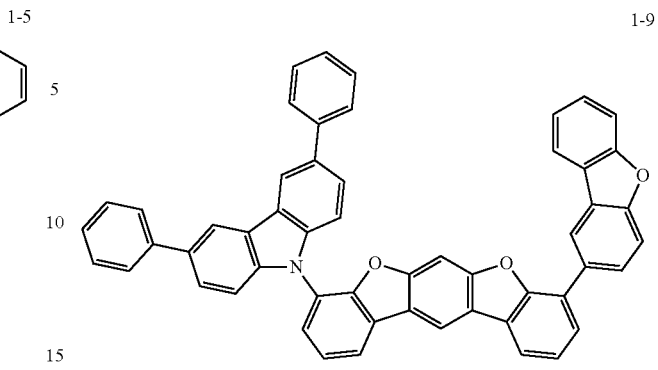
1-10
1-11
1-12
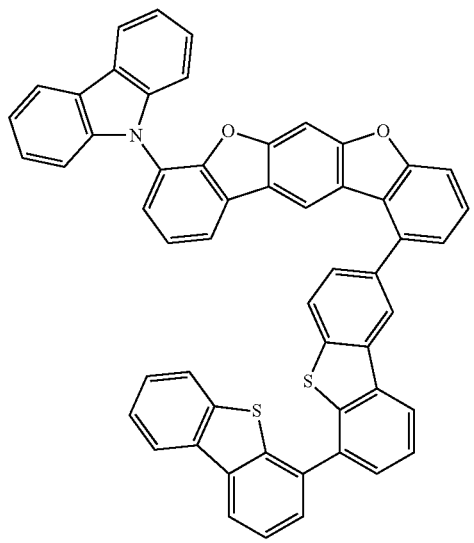

1-13
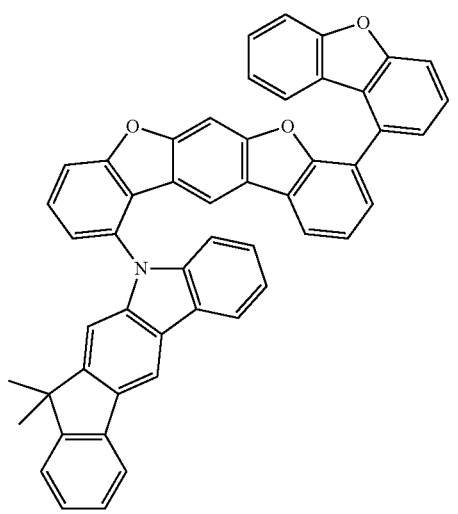
1-14
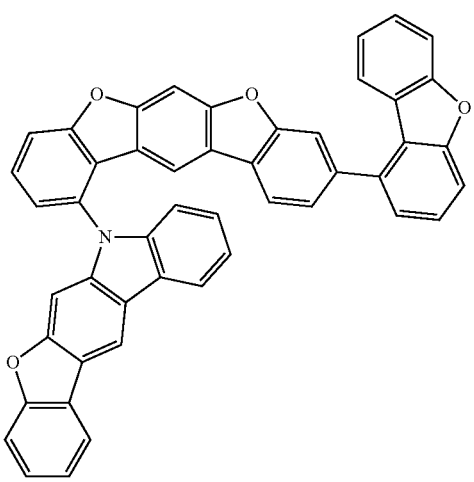
1-15
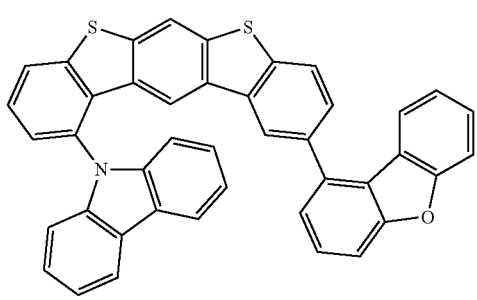
1-16
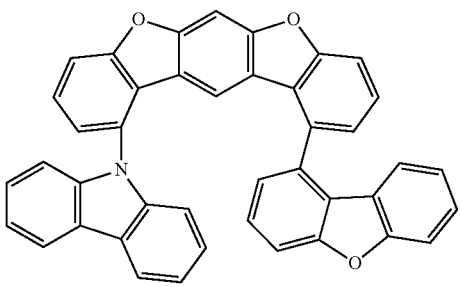
1-17
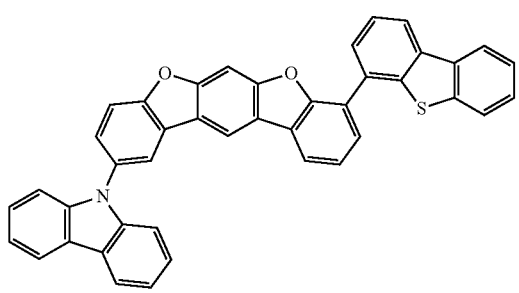
4. The organic compound of claim 1, wherein the organic compound has the following structure of Chemical Formula 4:
[Chemical Formula 4]
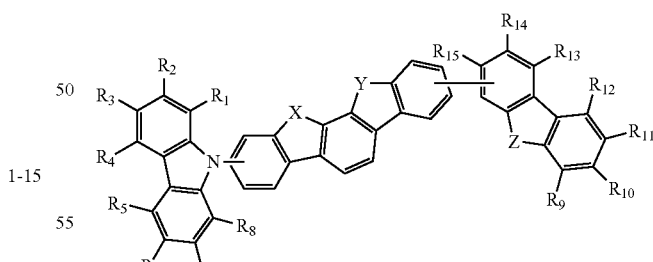
wherein each of $R_1$ to $R_{15}$, X, Y and Z is identical as defined in Chemical Formula 1.
5. The organic compound of claim 4, wherein the organic compound is selected from:

2-1
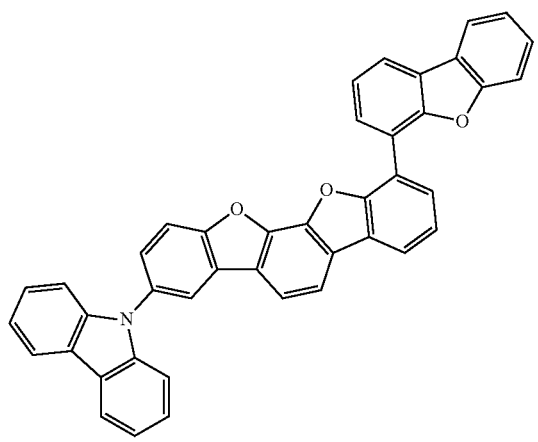
2-2
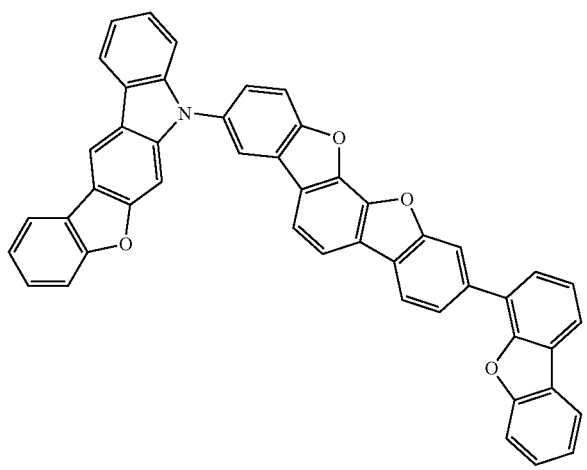
2-3
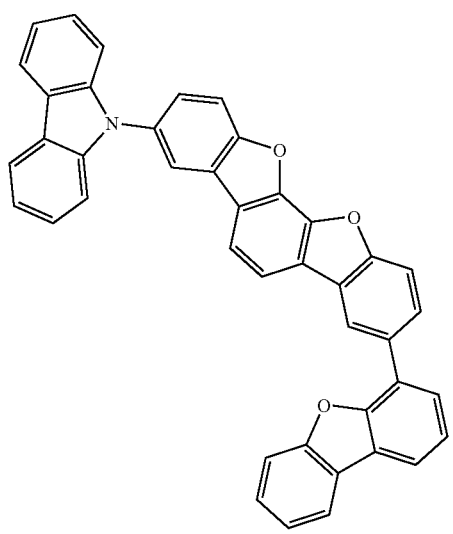
2-4
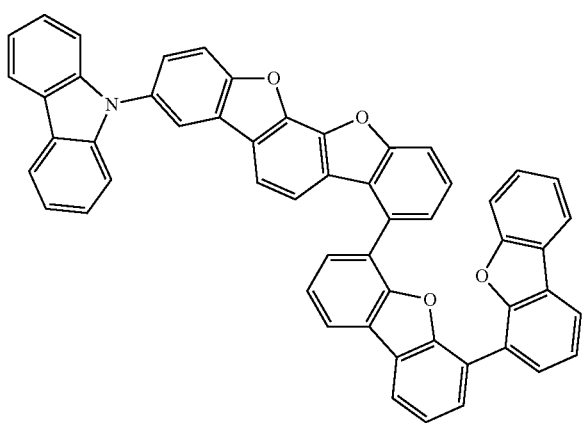
2-5
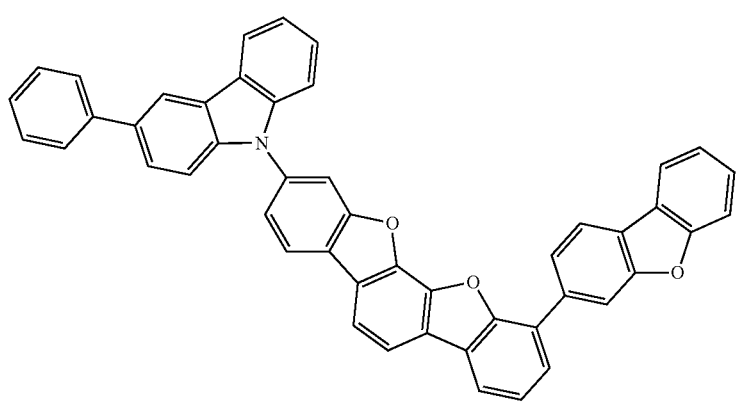

-continued
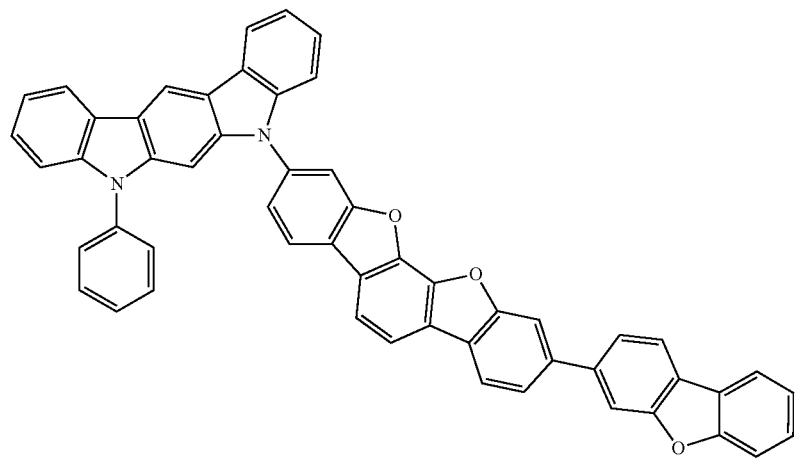
2-6
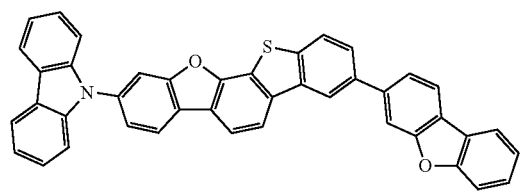
2-7
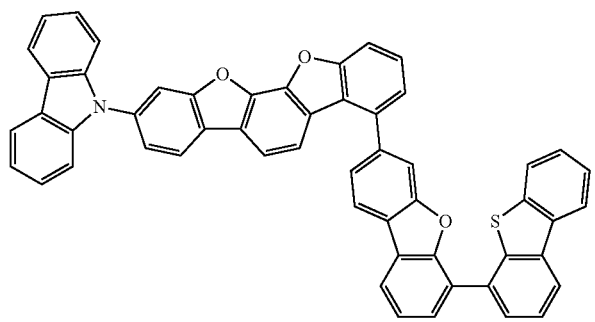
2-8
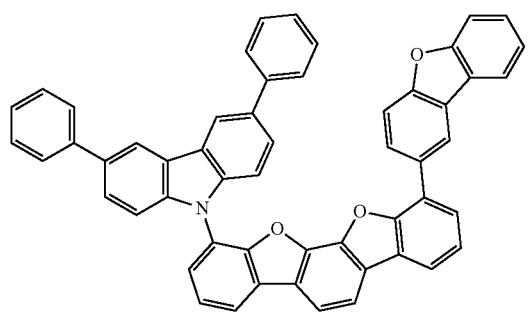
2-9
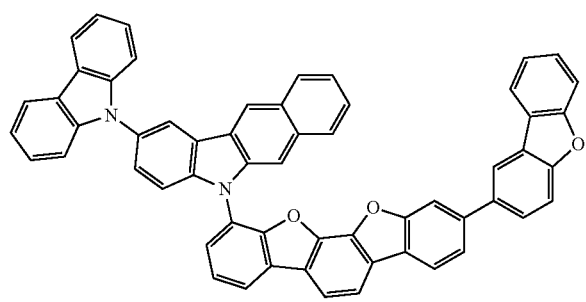
2-10

-continued
2-11
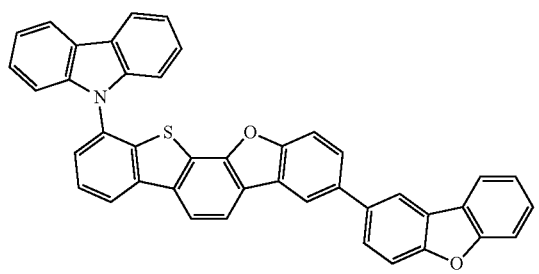
2-12
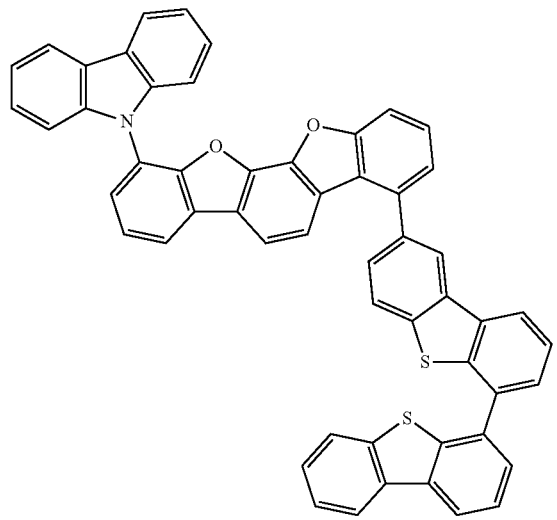
2-13
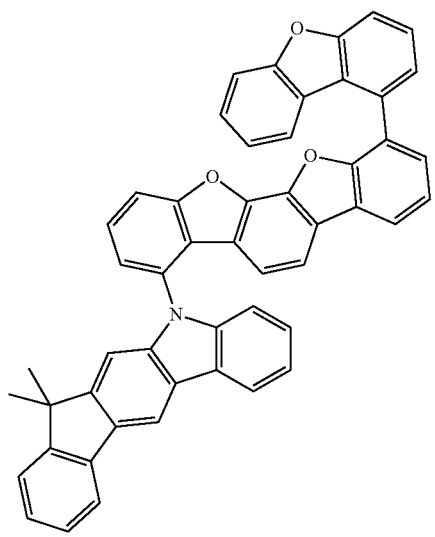
2-14
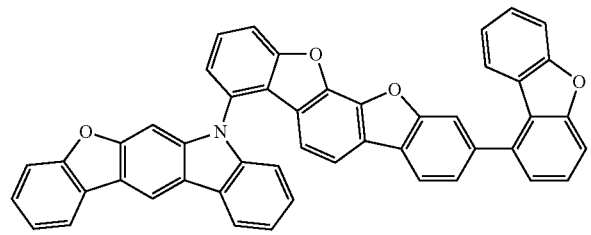
2-15
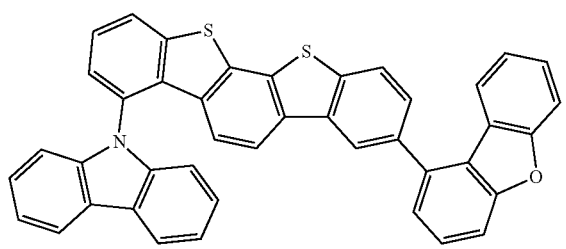
2-16
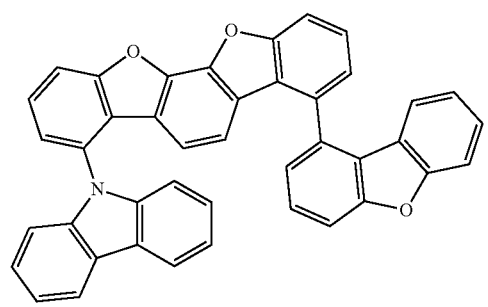

6. The organic compound of claim 1, wherein the organic compound has the following structure of Chemical Formula 6:
[Chemical Formula 6]
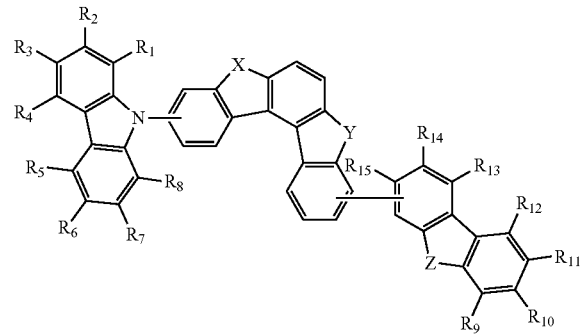
wherein each of $R_1$ to $R_{15}$, X, Y and Z is identical as defined in Chemical Formula 1.
7. The organic compound of claim 6, wherein the organic compound is selected from:
3-1
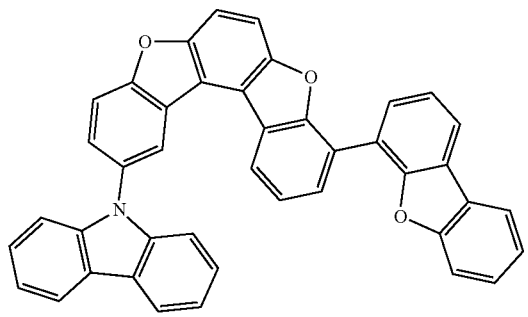
3-2
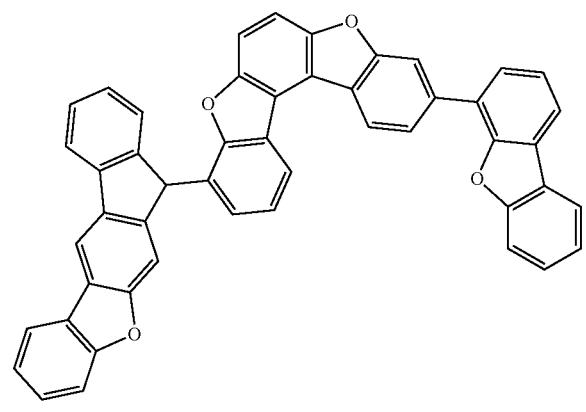
3-3
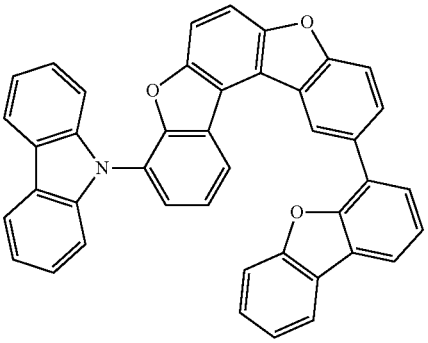
3-4
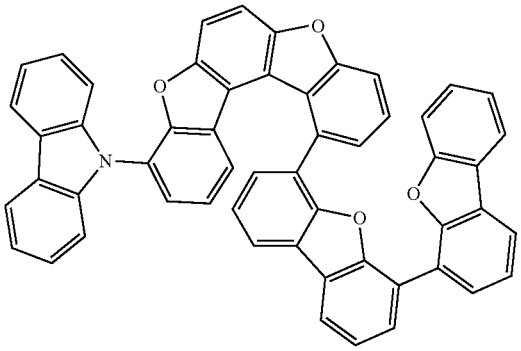
3-5
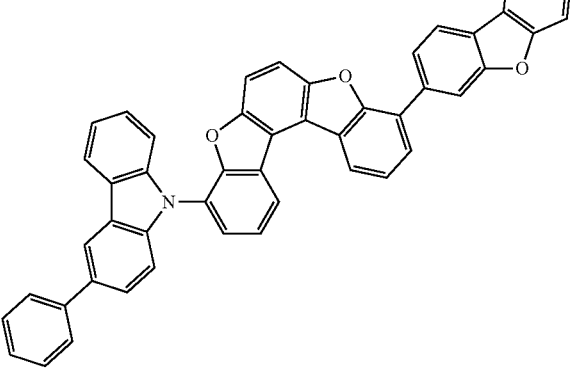
3-6
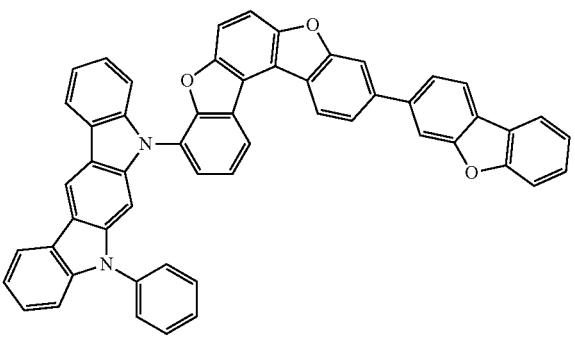

3-7
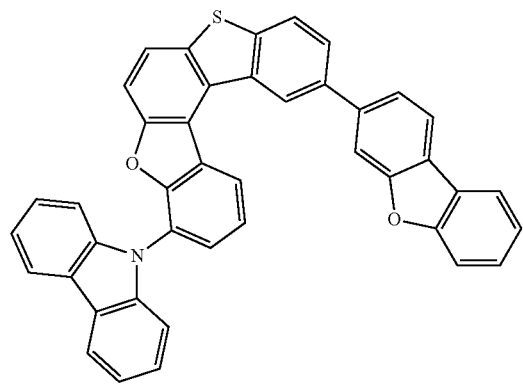
3-8
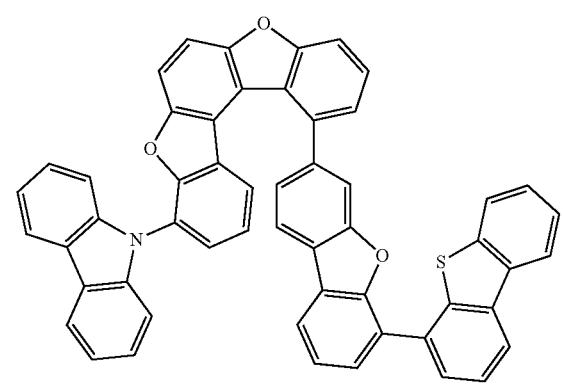
3-9
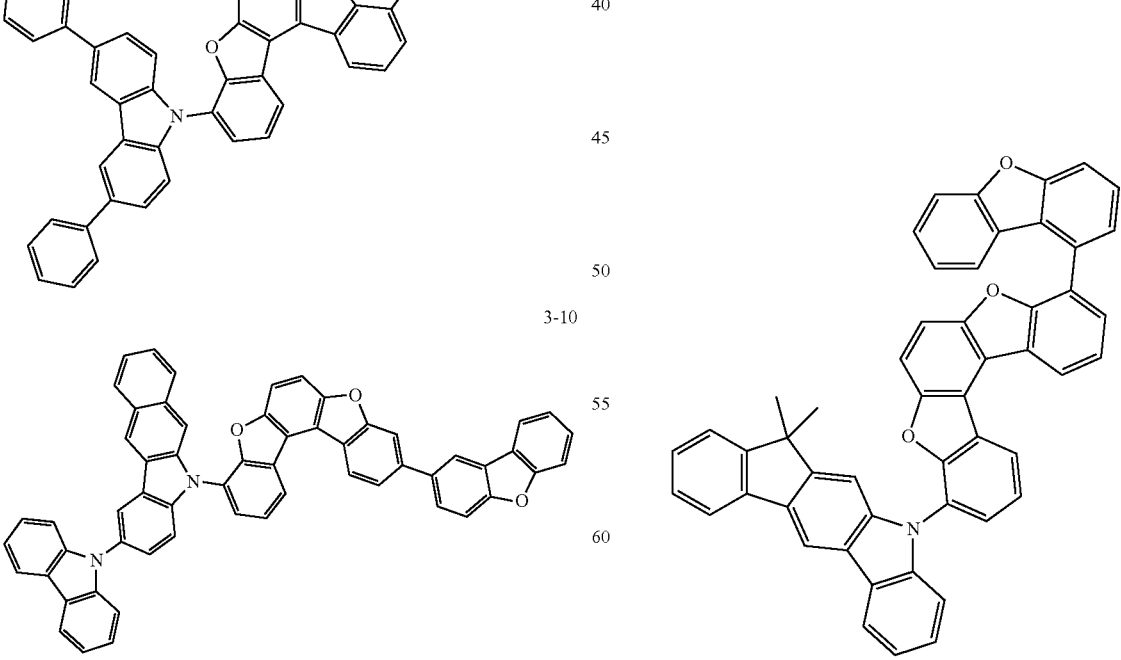
3-10
3-11
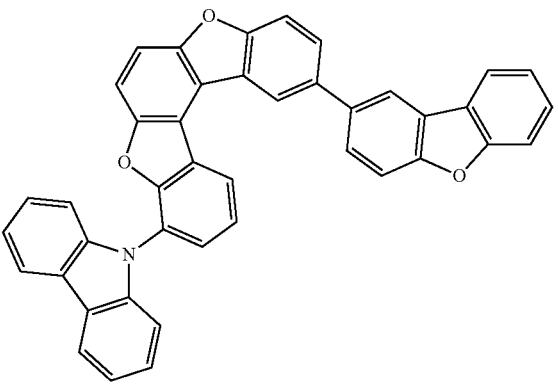
3-12
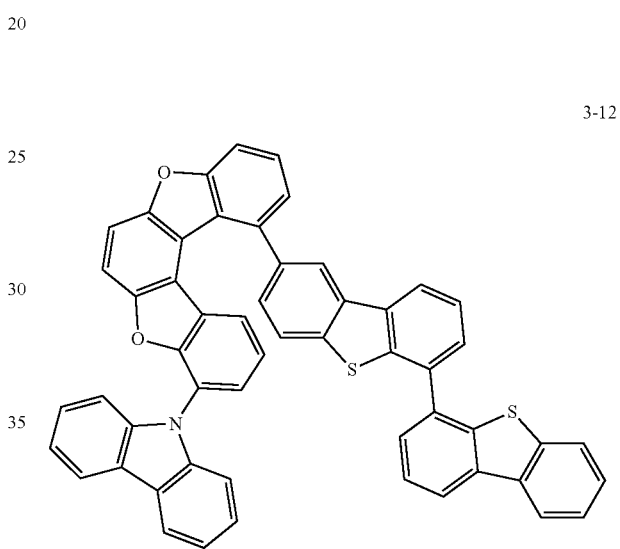
3-13

-continued
3-14
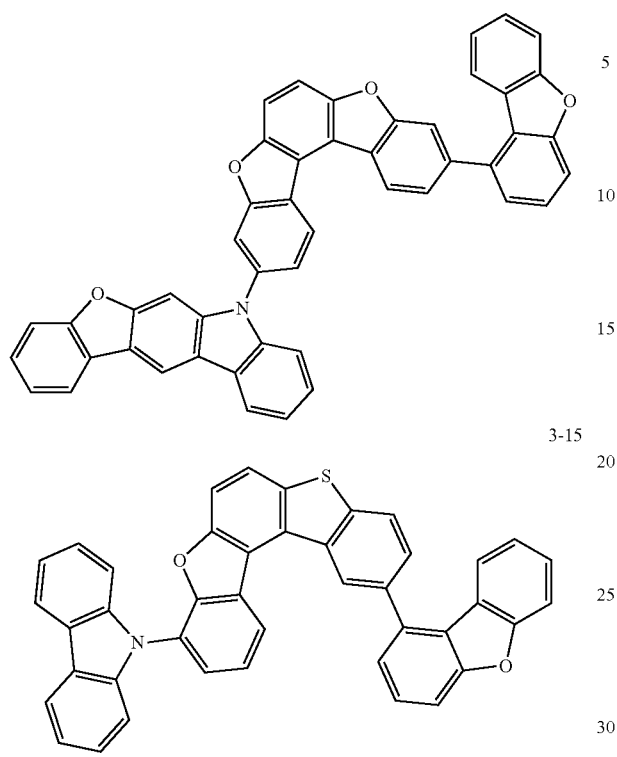
3-15
3-16
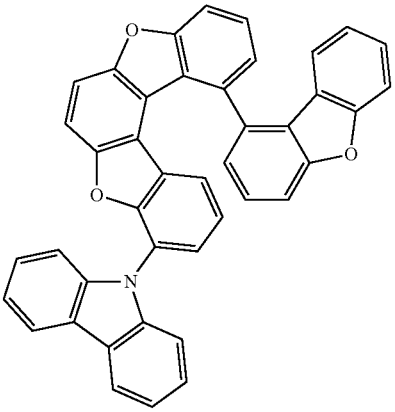
8. The organic compound of claim 1, wherein the organic compound has the following structure of Chemical Formula 8:
[Chemical Formula 8]
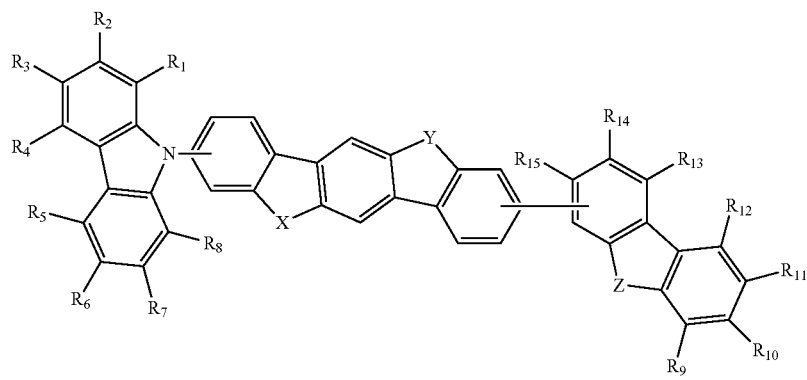
wherein each of $R_1$ to $R_{15}$, X, Y and Z is identical as defined in Chemical Formula 1.
9. The organic compound of claim 8, wherein the organic compound is selected from:
4-1
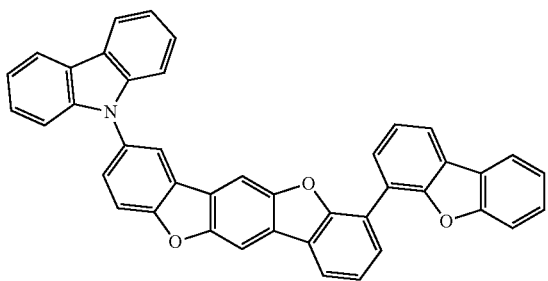
4-2
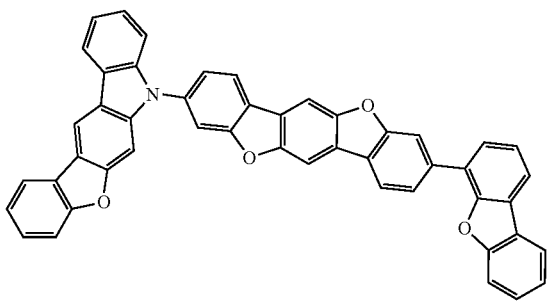

-continued
4-3
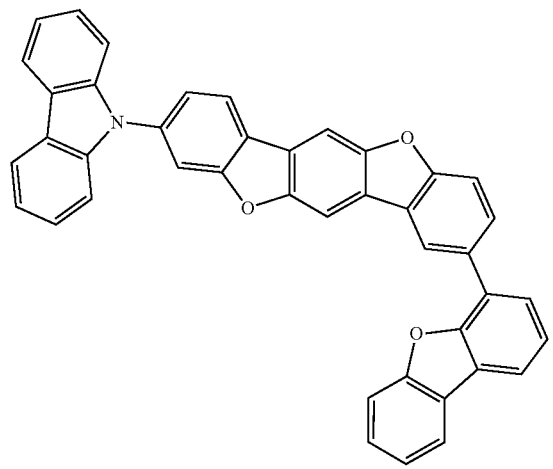
4-4
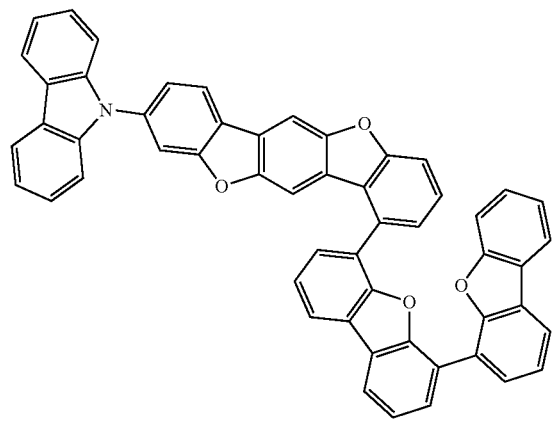
4-5
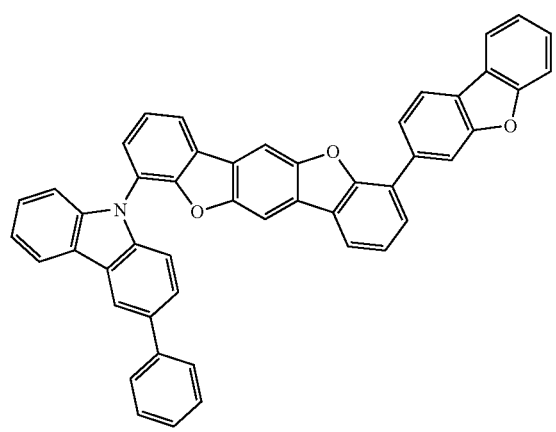
4-6
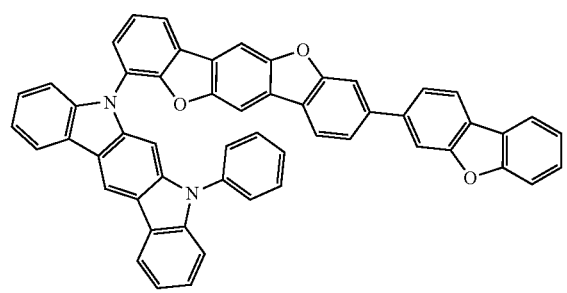
4-7
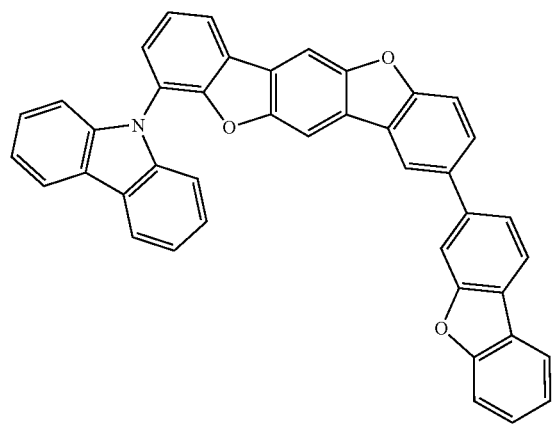
4-8
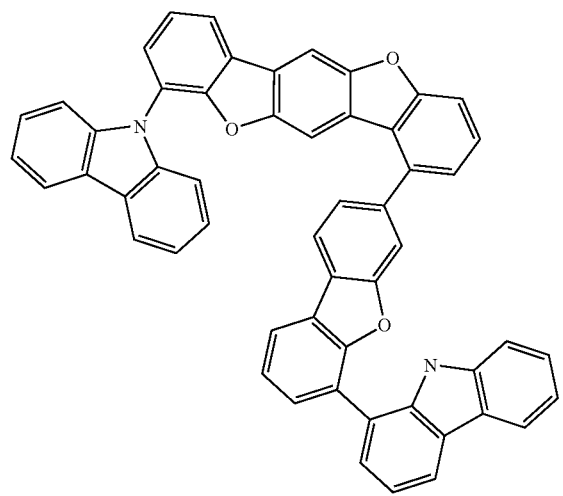

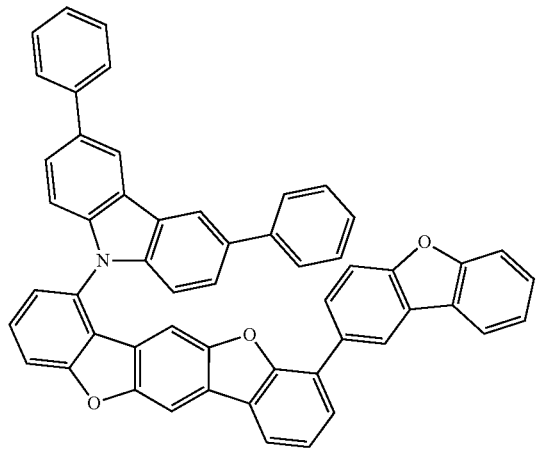
4-9
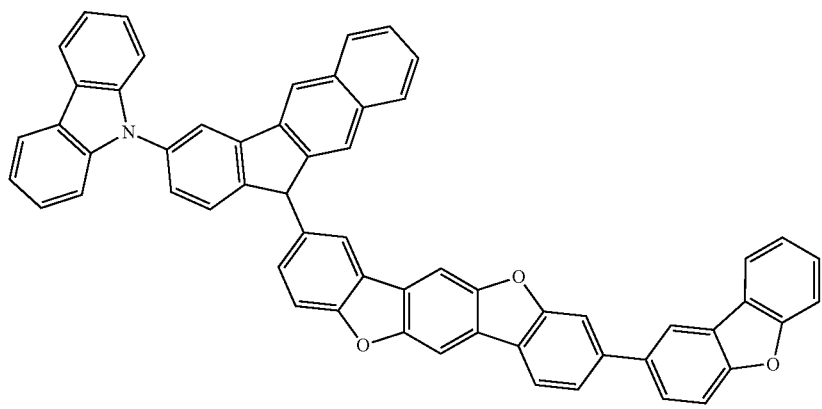
4-10
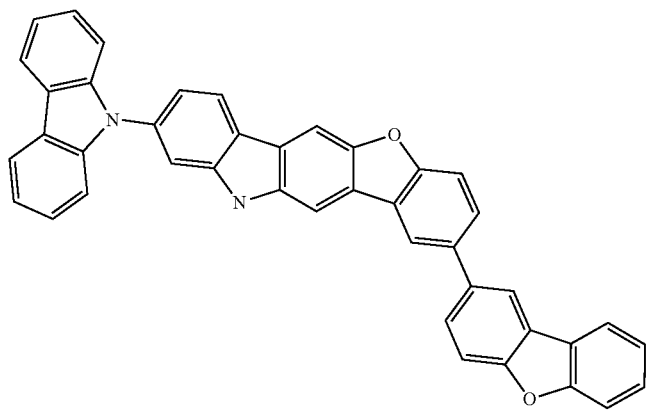
4-11

-continued
4-12
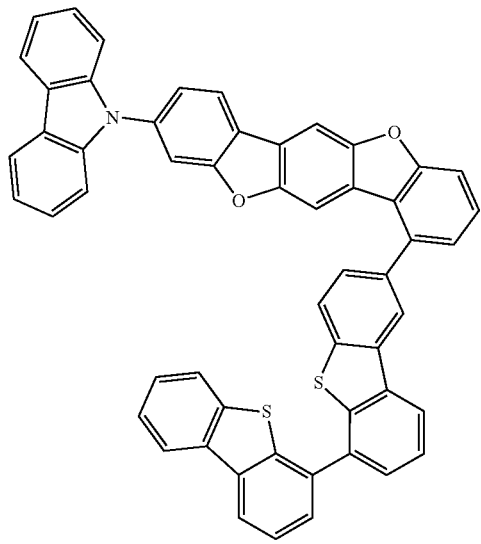
4-13
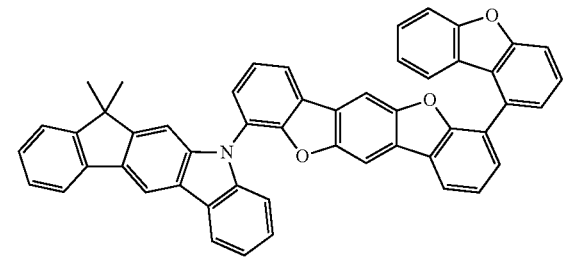
4-14
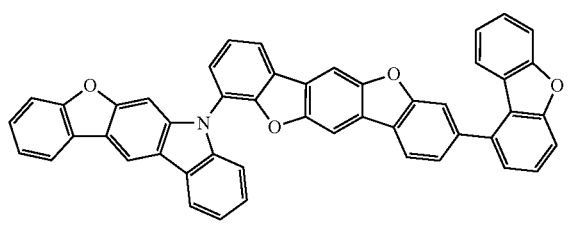
4-15
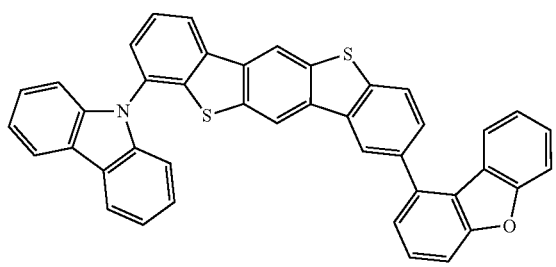
4-16
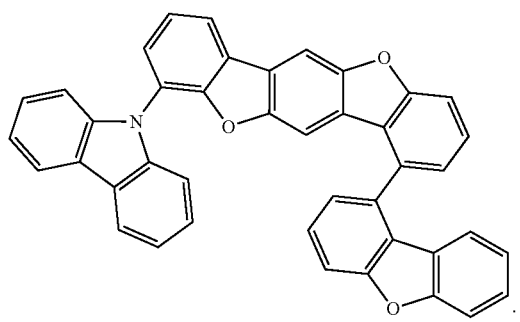
10. An organic light emitting diode, comprising:
a first electrode;
a second electrode facing the first electrode; and
an emitting material layer disposed between the first and second electrodes,
wherein the emitting material layer comprises an organic compound having the following structure of Chemical Formula 1:

[Chemical Formula 1]

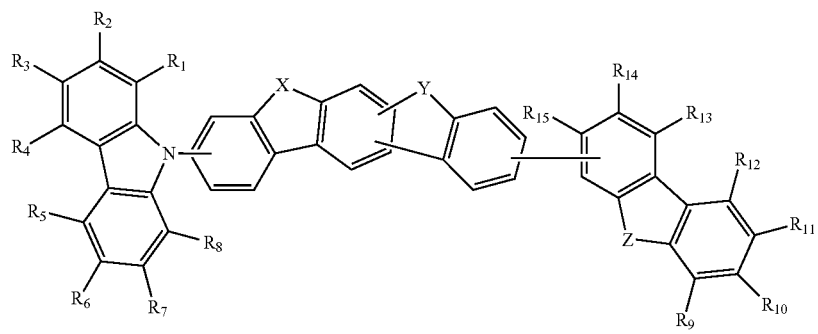

wherein each of $R_1$ to $R_{15}$ is independently selected from the group consisting of hydrogen, an unsubstituted or substituted silyl group, an unsubstituted or substituted $C_1$-$C_{20}$ alkyl group, an unsubstituted or substituted $C_1$-$C_{20}$ alkoxy group, an unsubstituted or substituted $C_1$-$C_{20}$ alkyl amino group, an unsubstituted or substituted $C_6$-$C_{30}$ aromatic group and an unsubstituted or substituted $C_3$-$C_{30}$ hetero aromatic group, or two adjacent groups among $R_1$ to $R_{15}$ form an unsubstituted or substituted $C_6$-$C_{20}$ aromatic ring or an unsubstituted or substituted $C_3$-$C_{20}$ hetero aromatic ring; each of X, Y and Z is independently oxygen (O) or sulfur (S).

11. The organic light emitting diode of claim 10, wherein the organic compound has the following structure of Chemical Formula 2:

[Chemical Formula 2]

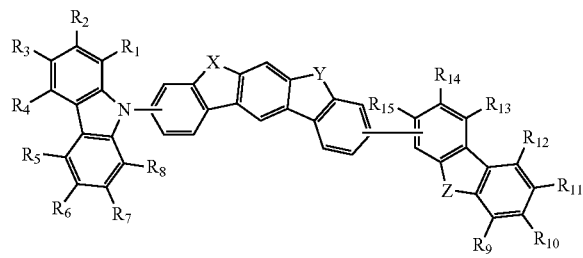

wherein each of $R_1$ to $R_{15}$, X, Y and Z is identical as defined in Chemical Formula 1.

12. The organic light emitting diode of claim 10, wherein the organic compound has the following structure of Chemical Formula 4:

[Chemical Formula 4]

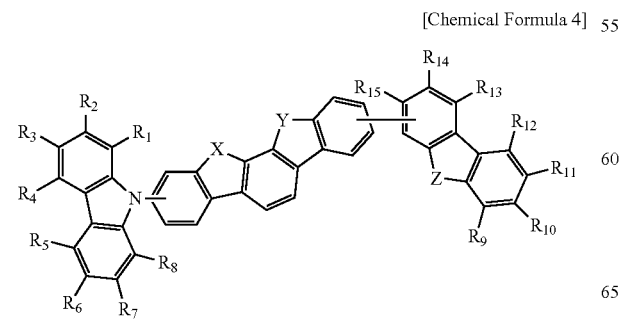

wherein each of $R_1$ to $R_{15}$, X, Y and Z is identical as defined in Chemical Formula 1.

13. The organic light emitting diode of claim 10, wherein the organic compound has the following structure of Chemical Formula 6:

[Chemical Formula 6]

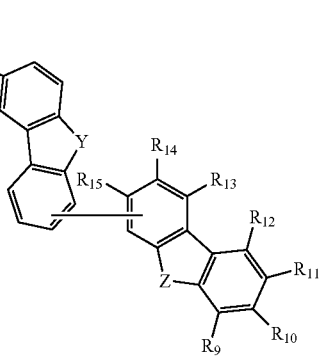

wherein each of $R_1$ to $R_{15}$, X, Y and Z is identical as defined in Chemical Formula 1.

14. The organic light emitting diode of claim 10, wherein the organic compound has the following structure of Chemical Formula 8:

[Chemical Formula 8]

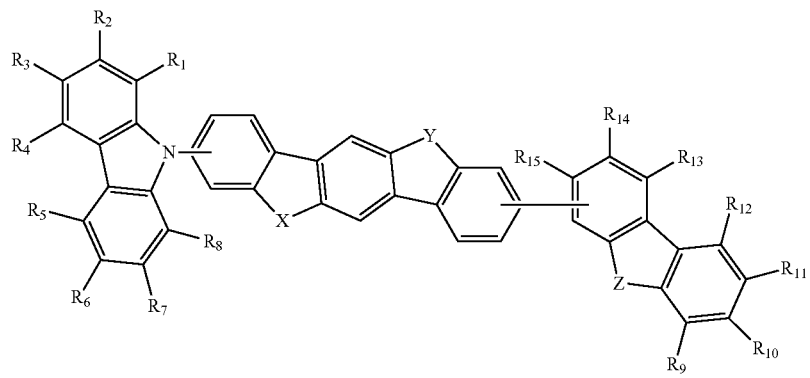

wherein each of $R_1$ to $R_{15}$, X, Y and Z is identical as defined in Chemical Formula 1.

15. The organic light emitting diode of claim 10, wherein the emitting material layer comprises a first compound and a second compound, and wherein the second compound comprises the organic compound.

16. The organic light emitting diode of claim 15, wherein an excited triplet energy level of the first compound is higher than an excited triplet energy level of the second compound.

17. The organic light emitting diode of claim 15, the emitting material layer further comprises a third compound.

18. The organic light emitting diode of claim 17, wherein an excited singlet energy level of the third compound is lower than an excited singlet energy level of the second compound.

19. The organic light emitting diode of claim 15, wherein the emitting material layer comprises:
   a first emitting material layer disposed between the first electrode and the second electrode, and
   a second emitting material layer disposed between the first electrode and the first emitting material layer or between the first emitting material layer and the second electrode,
   wherein the first emitting material layer comprises the first compound and the second compound, and
   wherein the second emitting material layer comprises a fourth compound and a fifth compound.

20. The organic light emitting diode of claim 19, wherein an excited triplet energy level of the fourth compound is higher than an excited triplet energy level of the second compound, and wherein an excited singlet energy level of the fifth compound is lower than an excited singlet energy level of the second compound.

21. The organic light emitting diode of claim 19, the emitting material layer further comprises a third emitting material layer disposed oppositely to the second emitting material layer with respect to the first emitting material layer, and wherein the third emitting material layer comprises a sixth compound and a seventh compound.

22. The organic light emitting diode of claim 21, wherein an excited triplet energy level of the sixth compound is higher than an excited triplet energy level of the second compound, and wherein an excited singlet energy level of the seventh compound is lower than an excited singlet energy level of the second compound.

23. An organic light emitting device, comprising:
   a substrate; and
   the organic light emitting diode of claim 10 over the substrate.

* * * * *